US009127076B2

(12) United States Patent
Abdullah et al.

(10) Patent No.: US 9,127,076 B2
(45) Date of Patent: Sep. 8, 2015

(54) MODIFIED PEPTIDES HAVING TOXIN-ENHANCING EFFECTS

(75) Inventors: Mohd Amir-Fursan Abdullah, Selangor (MY); Michael J. Adang, Athens, GA (US)

(73) Assignee: The University of Georgia Research Foundation, Athens, GA (US)

( * ) Notice: Subject to any disclaimer, the term of this patent is extended or adjusted under 35 U.S.C. 154(b) by 1519 days.

(21) Appl. No.: 12/672,972

(22) PCT Filed: Aug. 11, 2008

(86) PCT No.: PCT/US2008/072812
§ 371 (c)(1),
(2), (4) Date: May 8, 2012

(87) PCT Pub. No.: WO2009/023639
PCT Pub. Date: Feb. 19, 2009

(65) Prior Publication Data
US 2012/0220521 A1    Aug. 30, 2012

Related U.S. Application Data

(60) Provisional application No. 61/084,951, filed on Jul. 30, 2008, provisional application No. 60/956,618, filed on Aug. 17, 2007, provisional application No. 60/964,249, filed on Aug. 10, 2007.

(51) Int. Cl.
*C07K 14/435* (2006.01)
*A01N 37/46* (2006.01)
*C07K 14/325* (2006.01)

(52) U.S. Cl.
CPC .......... *C07K 14/43563* (2013.01); *A01N 37/46* (2013.01); *C07K 14/325* (2013.01)

(58) Field of Classification Search
None
See application file for complete search history.

(56) References Cited

U.S. PATENT DOCUMENTS 6,500,617 B1 * 12/2002 Stemmer et al. .................. 506/1
2005/0283857 A1 * 12/2005 Adang et al. .................. 800/302

OTHER PUBLICATIONS

Novotny et al, Nature 416:841-44 (2002).*
Bel & Eseriche, Gene 381:71-80 (2006).*
Guo et al., Proc. Natl. Acad. Sci. USA 101_9205 (2004).*
Argolo-Filho_Insects_5_62_2014.*

* cited by examiner

*Primary Examiner* — Medina A Ibrahim
*Assistant Examiner* — Russell Boggs
(74) *Attorney, Agent, or Firm* — Faegre Baker Daniel LLP

(57) ABSTRACT

This invention relates in part to modifying BtBooster (BtB) peptides, in part to increase their stability in insect midgut digestive juices. Some preferred embodiments of BtB have removed proteinase cleavage sites resulting in increased stability of the modified BtB in the insect gut, while retaining the ability to enhance B.t. proteins for improved insect control. In some preferred embodiments, the protease-stable BtB is used in combination with B.t. spores and/or crystals comprising a Cry protein. Also reported herein is the significant and increased enhancement of Bt toxins against relatively Bt-tolerant insects (*Helicoverpa zea, Spodoptera exigua* and *Agrotis ipsilon*), when used with BtBs. We also describe increased toxin enhancement with cadherin fragments that are stabilized against over-digestion by insect midgut proteinases. We also report enhancement of Bt Cry1F toxin by cadherin fragments.

11 Claims, 20 Drawing Sheets

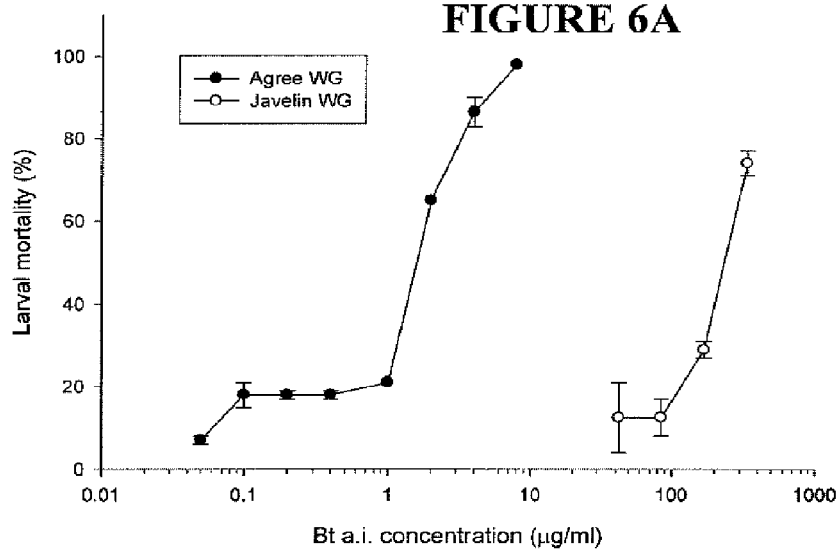
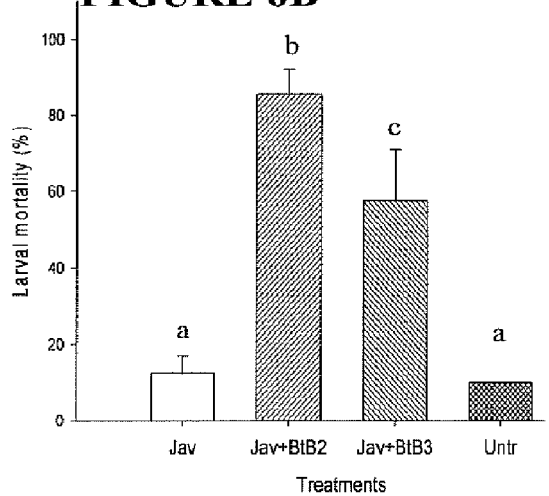
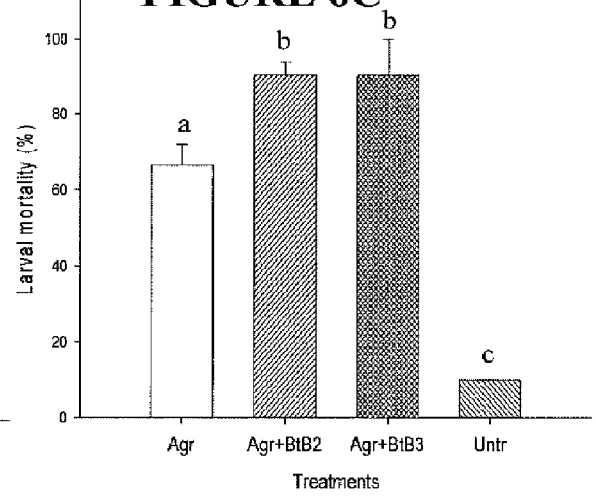

FIGURE 10A

*Statistically significant enhancement was observed for Ms-CR10-12(PS)

FIGURE 10B

*Significant enhancement was observed for spray-dried preparation of Ms-CR10-12(PS)

FIGURE 12

*Spodoptera exigua* diet bioassay
Cry1Ca alone or with
BtB4 = Ms-CR10-12

Bar chart (y-axis 0–100):
- A: Cry1Ca — ~15
- B: Cry1Ca:Ms-CR10-12 (1:1) — ~73
- C: Cry1Ca:Ms-CR10-12 (1:5) — ~67
- D: Cry1Ca:Ms-CR10-12 (1:10) — ~65
- E: Cry1Ca:Ms-CR10-12 (1:50) — ~53
- F: Cry1Ca:Ms-CR10-12 (1:100) — ~34

Cry1Ca Treatments

Diet surface treatment bioassay with neonate *H. zea*. Sample size: 32 larvae/rep x 2 rep/treatment. Bioassay was scored on Day 7.
BtB5 = Ms-CR8-10(PS)
BtB9 = Sf-CR8-10
*Addition of BtB5 and BtB9 to Cry1Ac+Cry1Fa enhanced toxicity significantly.

a. 0.025 µg/cm$^2$ Cry1Ac + 0.125 µg/cm$^2$ Cry1Fa (1:5 ratio)
b. 0.05 µg/cm$^2$ Cry1Ac + 0.25 µg/cm$^2$ Cry1Fa (1:5 ratio)
c. 0.10 µg/cm$^2$ Cry1Ac + 0.50 µg/cm$^2$ Cry1Fa (1:5 ratio)
d. 0.025 µg/cm$^2$ Cry1Ac + 0.125 µg/cm$^2$ Cry1Fa + 0.125 µg/cm$^2$ BtB5 + 0.125 µg/cm$^2$ BtB9
e. 0.05 µg/cm$^2$ Cry1Ac + 0.25 µg/cm$^2$ Cry1Fa + 0.25 µg/cm$^2$ BtB5 + 0.125 µg/cm$^2$ BtB9
f. 0.10 µg/cm$^2$ Cry1Ac + 0.50 µg/cm$^2$ Cry1Fa + 0.50 µg/cm$^2$ BtB5 + 0.125 µg/cm$^2$ BtB9

FIGURE 19
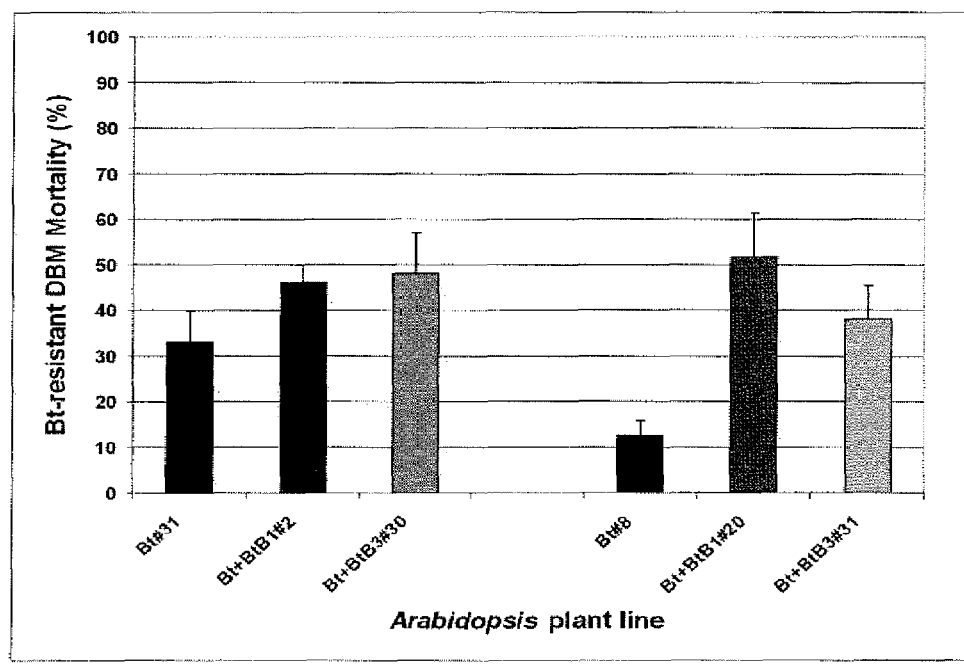
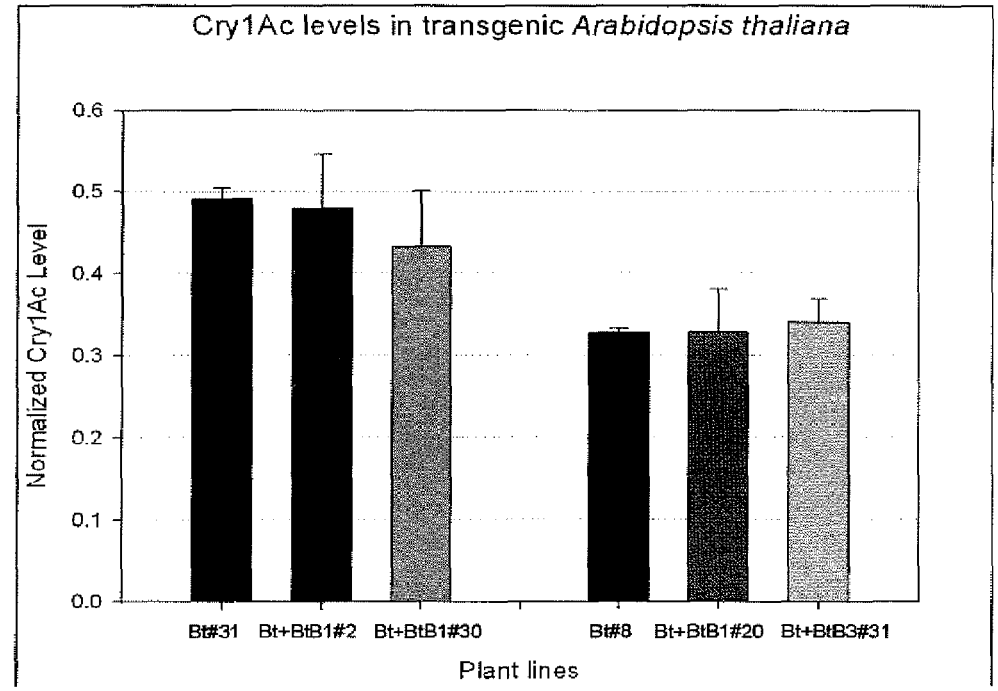

FIGURE 20

Alignment of CR12 sequences from ten lepidopteran species.

```
                        10         20         30         40         50
                         |          |          |          |          |
L.dispar        GISTSDNINRVLLTVQATHSEGAPVTYEIDHSTMIVDPTLEAVKDTAFVL
P.gossypiella   GISTSDNINRELLTVRATHSENAQLTYTIEDGSMVVDSTLEAVKDSAFHL
H.armigera      GISAGDFIERNLLTVVATHSEGLPITYTLIQESMEADPPLEAVQESAFIL
H.virescens     GISTLDTINRALLTLHATHSEGLPVTYTLIQDSMEADSTLQAVQETAFNL
C.suppressalis  GISVLDTIQRELLTVQATHSLGDNISYAIDAASMVADSSLAVVAETAFLL
O.nubilalis     VISTLDSIGRELLTVRASHTEDDIITYTIDRASMQLDSSLEAVRDSAFAL
P.xylostella    GISTMDSINRELFTVKATHTENLSIKYTIDPSSMVADTSLQSVQGSAFEL
M.sexta         GISTADSIGRELLRLHATQSEGSAITYAIDYDTMVVDPSLEAVRQSAFVL
B.mori          GISTSDSINRELLILQATHSENAPIIYTIDWSTMVTDPTLASVRETAFIL
S.frugiperda    GVLHTDSIHKELVYLAAKHSEGLPIVYSIDQETMKIDESLQTVVEDAFDI
                 :   * * :*. : *.:: .   :  * :    :*   * .*  *   ** :

60         70         80         90        100
                         |          |          |          |          |
L.dispar        NSQTGVLTLNMQPTAFMHGNFEFKVVATDPSEATDRAAVKIYLISSLNRV
P.gossypiella   NAQTGVLILRIQPTASMQGMFEFNVIATDPDEKTDTAEVKVYLISSQNRV
H.armigera      NPETGVLSLNFQPTAAMHGMFEFEVEATDSRRETARTEVKVYLISDRNRV
H.virescens     NPQTGVLTLNFQPTASMHGMFEFDVMAIDTVGETARTEVKVYLISDRNRV
C.suppressalis  HARSGVLSLNMQPTANMHGMFEFDVTATDSSGGVGRAQVKVYLISSQNRV
O.nubilalis     HATTGVFSLNMQPTASMHGMFEFDVIATDTASAIDTARVKVYLISSQNRV
P.xylostella    DADSGVLTLKIKPTASMRGMFEFVVATDTEQATDRAEVKVYIVSDNNRV
M.sexta         NAQTGVLTLNIQPTATMHGLFKFEVTATDTAGAQDRTDVTVYVVSSQNRV
B.mori          NPHTGVLTLNIQPTASMHGMFEFQVVATDPAGYSDRANVKIYLISTRNRV
S.frugiperda    NSATGVISLNFQPTSVMHGSFDFEVVASDTRGASDRAKVSIYMISTRVRV
                 . :**: *.::**: *:*  *.*.* * *.      : *.:*::*   **
```

Alignment data :
Alignment length : 100
Identity (*) : 28 is 28.00 %
Strongly similar (:) : 19 is 19.00 %
Weakly similar (.) : 11 is 11.00 %
Different : 42 is 42.00 %

SEQUENCE LISTING

```
<160> NUMBER OF SEQ ID NOS: 40

<210> SEQ ID NO 1
<211> LENGTH: 1467
<212> TYPE: DNA
<213> ORGANISM: Manduca sexta

<400> SEQUENCE: 1
atggacctca agggatattg ggggacgtac gctatacata tacgggcatt cgaccacggc      60
attccgcaaa tgtccatgaa cgagacatat gagctgatta tccatccgtt caactactac     120
gcgcctgagt tcgtcttccc gaccaacgat gccgtcatac gacttgcgag ggaacgagct     180
gtaatcaatg gagttctagc gacagtgaac ggagagttct tggagcggat atcggcgact     240
gacccggacg gactccacgc gggcgtcgtc accttccaag tggtaggcga tgaggaatca     300
caacggtact ttcaagtagt taacgatggc gcgaacctcg gctcgttgag gttactgcaa     360
gccgttccag aggagatcag ggagttccgg ataacgattc gcgctacaga ccagggaacg     420
gacccaggac cgctgtccac ggacatgacg ttcagagttg tttttgtgcc cacgcaagga     480
gaacctagat tcgcgtcctc agaacatgct gtcgctttca tagaaaagag tgccggcatg     540
gaagagtctc accaacttcc tctagcacaa gacatcaaga accatctctg tgaagacgac     600
tgtcacagca tttactatcg tattatcgat ggcaacagcg agggtcattt cggcctggat     660
cctgttcgca acaggttgtt cctgaagaaa gagctgataa gagaacaaag tgcctcccac     720
actctgcaag tggcggctag taactcgccc gatggtggca ttccacttcc tgcttccatc     780
cttactgtca ctgttaccgt gagggaggca gaccctcgtc cagtgtttat gagggaattg     840
tacaccgcag ggatatccac agcggactcc atcggcagag agctgctcag attacatgcg     900
acccagtctg aaggcgcggc cattacttat gctatagact acgatacaat ggtagtggac     960
cccagcctgg aggcagtgag acagtcggct ttcgtactga acgctcaaac cggagtgctg    1020
```

```
acgcttaata tccagcccac ggccacgatg catggactgt tcaaattcga agtcacagct    1080
actgacacgg ccggcgctca ggaccgcacc gacgtcaccg tgtacgtggt atcctcgcag    1140
aaccgcgtct acttcgtgtt cgtcaacacg ctgcaacagg tcgaagacaa cagagacttt    1200
atcgcggaca ccttcagcgc tgggttcaac atgacctgca acatcgacca agtggtgccc    1260
gccaacgacc ccgtcaccgg cgtggcgctg agcacagca cgcagatgcg cggccacttc    1320
atacgggaca acgtacccgt actcgctgat gagatagaac agatccgtag tgacctagtc    1380
ctcctgagct cgatacaaac aacgctggcg gcgcgatcgc tggtgttgca ggacttgttg    1440
accaactcca gcccggactc ggcgcct                                        1467
```

<210> SEQ ID NO 2
<211> LENGTH: 489
<212> TYPE: PRT
<213> ORGANISM: Manduca sexta

<400> SEQUENCE: 2

```
Met Asp Leu Lys Gly Tyr Trp Gly Thr Tyr Ala Ile His Ile Arg Ala
1               5                   10                  15

Phe Asp His Gly Ile Pro Gln Met Ser Met Asn Glu Thr Tyr Glu Leu
            20                  25                  30

Ile Ile His Pro Phe Asn Tyr Tyr Ala Pro Glu Phe Val Phe Pro Thr
        35                  40                  45

Asn Asp Ala Val Ile Arg Leu Ala Arg Glu Arg Ala Val Ile Asn Gly
    50                  55                  60

Val Leu Ala Thr Val Asn Gly Glu Phe Leu Arg Ile Ser Ala Thr
65                  70                  75                  80

Asp Pro Asp Gly Leu His Ala Gly Val Val Thr Phe Gln Val Val Gly
                85                  90                  95

Asp Glu Glu Ser Gln Arg Tyr Phe Gln Val Val Asn Asp Gly Ala Asn
            100                 105                 110

Leu Gly Ser Leu Arg Leu Leu Gln Ala Val Pro Glu Glu Ile Arg Glu
        115                 120                 125

Phe Arg Ile Thr Ile Arg Ala Thr Asp Gln Gly Thr Asp Pro Gly Pro
    130                 135                 140

Leu Ser Thr Asp Met Thr Phe Arg Val Val Phe Val Pro Thr Gln Gly
145                 150                 155                 160

Glu Pro Arg Phe Ala Ser Ser Glu His Ala Val Ala Phe Ile Glu Lys
                165                 170                 175

Ser Ala Gly Met Glu Glu Ser His Gln Leu Pro Leu Ala Gln Asp Ile
            180                 185                 190

Lys Asn His Leu Cys Glu Asp Cys His Ser Ile Tyr Tyr Arg Ile
        195                 200                 205

Ile Asp Gly Asn Ser Glu Gly His Phe Gly Leu Asp Pro Val Arg Asn
    210                 215                 220

Arg Leu Phe Leu Lys Lys Glu Leu Ile Arg Glu Gln Ser Ala Ser His
225                 230                 235                 240

Thr Leu Gln Val Ala Ala Ser Asn Ser Pro Asp Gly Gly Ile Pro Leu
                245                 250                 255

Pro Ala Ser Ile Leu Thr Val Thr Val Thr Val Arg Glu Ala Asp Pro
            260                 265                 270

Arg Pro Val Phe Met Arg Glu Leu Tyr Thr Ala Gly Ile Ser Thr Ala
        275                 280                 285
```

```
Asp Ser Ile Gly Arg Glu Leu Leu Arg Leu His Ala Thr Gln Ser Glu
    290                 295                 300
Gly Ala Ala Ile Thr Tyr Ala Ile Asp Tyr Asp Thr Met Val Val Asp
305                 310                 315                 320
Pro Ser Leu Glu Ala Val Arg Gln Ser Ala Phe Val Leu Asn Ala Gln
                325                 330                 335
Thr Gly Val Leu Thr Leu Asn Ile Gln Pro Thr Ala Thr Met His Gly
            340                 345                 350
Leu Phe Lys Phe Glu Val Thr Ala Thr Asp Thr Ala Gly Ala Gln Asp
        355                 360                 365
Arg Thr Asp Val Thr Val Tyr Val Val Ser Ser Gln Asn Arg Val Tyr
    370                 375                 380
Phe Val Phe Val Asn Thr Leu Gln Gln Val Glu Asp Asn Arg Asp Phe
385                 390                 395                 400
Ile Ala Asp Thr Phe Ser Ala Gly Phe Asn Met Thr Cys Asn Ile Asp
                405                 410                 415
Gln Val Val Pro Ala Asn Asp Pro Val Thr Gly Val Ala Leu Glu His
            420                 425                 430
Ser Thr Gln Met Arg Gly His Phe Ile Arg Asp Asn Val Pro Val Leu
        435                 440                 445
Ala Asp Glu Ile Glu Gln Ile Arg Ser Asp Leu Val Leu Leu Ser Ser
    450                 455                 460
Ile Gln Thr Thr Leu Ala Arg Ser Leu Val Leu Gln Asp Leu Leu
465                 470                 475                 480
Thr Asn Ser Ser Pro Asp Ser Ala Pro
            485
```

<210> SEQ ID NO 3
<211> LENGTH: 1467
<212> TYPE: DNA
<213> ORGANISM: Manduca sexta

<400> SEQUENCE: 3

```
atggaccctca agggatattg ggggacgtac gctatacata tacgggcatt cgaccacggc    60
attccgcaaa tgtccatgaa cgagacatat gagctgatta ccatccgtt caactactac    120
gcgcctgagt tcgtcttccc gaccaacgat gccgtcatac gacttgcgag ggaacgagct    180
gtaatcaatg gagttctagc gacagtgaac ggagagttct ggagcggat atcggcgact    240
gacccggacg gactccacgc gggcgtcgtc accttccaag tggtaggcga tgaggaatca    300
caacggtact tcaagtagt taacgatggc gcgaacctcg gctcgttgag gttactgcaa    360
gccgttccag aggagatcag ggagttccgg ataacgattc gcgctacaga ccagggaacg    420
gacccaggac cgctgtccac ggacatgacg ttcagagttg ttttgtgcc cacgcaagga    480
gaacctagat tcgcgtcctc agaacatgct gtcgctttca tagaaaagag tgccggcatg    540
gaagagtctc accaacttcc tctagcacaa gacatcaaga accatctctg tgaagacgac    600
tgtcacagca tttactatcg tattatcgat ggcaacagcg agggtcattt cggcctggat    660
cctgttcgca acaggttgtt cctgaagaaa gagctgataa gagaacaaag tgcctcccac    720
actctgcaag tggcggctag taactcgccc gatggtggca ttccacttcc tgcttccatc    780
cttactgtca ctgttaccgt gagggaggca gaccctcgtc cagtgtttat gagggaattg    840
tacaccgcag ggatatccac agcggactcc atcggcagag agctgctcag attacatgcg    900
acccagtctg aaggcgcggc cattacttat gctatagact acgatacaat ggtagtggac    960
```

```
cccagcctgg aggcagtgag acagtcggct tcgtactga acgctcaaac cggagtgctg    1020
acgcttaata tccagcccac ggccacgatg catggactgt tcaaattcga agtcacagct    1080
actgacacgg ccggcgctca ggaccgcacc gacgtcaccg tgtacgtggt atcctcgcag    1140
aaccgcgtct acttcgtgtt cgtcaacacg ctgcaacagg tcgaagacaa cagagacttt    1200
atcgcggaca ccttcagcgc tgggttcaac atgacctgca acatcgacca agtggtgccc    1260
gccaacgacc ccgtcaccgg cgtggcgctg agcacagca cgcagatgcg cggccacttc    1320
atacgggaca acgtacccgt actcgctgat gagatagaac agatccgtag tgacctagtc    1380
ctcctgagct cgatacaaac aacgctggcg gcgcgatcgc tggtgttgca ggacttgttg    1440
accaactcca gcccggactc ggcgcct                                       1467

<210> SEQ ID NO 4
<211> LENGTH: 339
<212> TYPE: DNA
<213> ORGANISM: Artificial sequence
<220> FEATURE:
<223> OTHER INFORMATION: BtB2

<400> SEQUENCE: 4
atggggatat ccacagcgga ctccatcggc agagagctgc tcagattaca tgcgacccag      60
tctgaaggcg cggccattac ttatgctata gactacgata caatggtagt ggaccccagc     120
ctggaggcag tgagacagtc ggctttcgta ctgaacgctc aaaccggagt gctgacgctt     180
aatatccagc ccacggccac gatgcatgga ctgttcaaat tcgaagtcac agctactgac     240
acggccggcg ctcaggaccg caccgacgtc accgtgtacg tggtatcctc gcagaaccgc     300
gtctacttcg tgctcgagca ccaccaccac caccactga                            339

<210> SEQ ID NO 5
<211> LENGTH: 112
<212> TYPE: PRT
<213> ORGANISM: Artificial sequence
<220> FEATURE:
<223> OTHER INFORMATION: BtB2

<400> SEQUENCE: 5

Met Gly Ile Ser Thr Ala Asp Ser Ile Gly Arg Glu Leu Leu Arg Leu
1               5                   10                  15

His Ala Thr Gln Ser Glu Gly Ala Ala Ile Thr Tyr Ala Ile Asp Tyr
            20                  25                  30

Asp Thr Met Val Val Asp Pro Ser Leu Glu Ala Val Arg Gln Ser Ala
        35                  40                  45

Phe Val Leu Asn Ala Gln Thr Gly Val Leu Thr Leu Asn Ile Gln Pro
    50                  55                  60

Thr Ala Thr Met His Gly Leu Phe Lys Phe Glu Val Thr Ala Thr Asp
65                  70                  75                  80

Thr Ala Gly Ala Gln Asp Arg Thr Asp Val Thr Val Tyr Val Val Ser
                85                  90                  95

Ser Gln Asn Arg Val Tyr Phe Val Leu Glu His His His His His His
            100                 105                 110

<210> SEQ ID NO 6
<211> LENGTH: 339
<212> TYPE: DNA
<213> ORGANISM: Artificial sequence
<220> FEATURE:
<223> OTHER INFORMATION: BtB2
```

<400> SEQUENCE: 6

```
atggggatat ccacagcgga ctccatcggc agagagctgc tcagattaca tgcgacccag    60
tctgaaggcg cggccattac ttatgctata gactacgata caatggtagt ggaccccagc   120
ctggaggcag tgagacagtc ggctttcgta ctgaacgctc aaaccggagt gctgacgctt   180
aatatccagc ccacggccac gatgcatgga ctgttcaaat cgaagtcac agctactgac    240 acggccggcg ctcaggaccg caccgacgtc accgtgtacg tggtatcctc gcagaaccgc   300
gtctacttcg tgctcgagca ccaccaccac caccactga                          339
```

<210> SEQ ID NO 7
<211> LENGTH: 336
<212> TYPE: DNA
<213> ORGANISM: Artificial sequence
<220> FEATURE:
<223> OTHER INFORMATION: BtB3 (protease stabilized)

<400> SEQUENCE: 7

```
atggggatat ccacagcgga ctccatcggc agtgagctgc tcagtttaca tgcgacccag    60
tctgaaggcg cggccattac ttatgctata gactacgata caatggtagt ggaccccagc   120
ctggaggcag tgagtcagtc ggctctcgta ctgaacgctc aaaccggagt gctgacgctt   180
aatatccagc ccacggccac gatgcatgga ctgatcaata tcgaagtcac agctactgac   240
acggccggcg ctcaggaccg caccgacgtc accgtgtacg tggtatcctc gcagaaccgc   300
gtctacttcg tgctcgagca ccaccaccac cactga                             336
```

<210> SEQ ID NO 8
<211> LENGTH: 111
<212> TYPE: PRT
<213> ORGANISM: Artificial sequence
<220> FEATURE:
<223> OTHER INFORMATION: BtB3 (protease stabilized)

<400> SEQUENCE: 8

```
Met Gly Ile Ser Thr Ala Asp Ser Ile Gly Ser Glu Leu Leu Ser Leu
1               5                   10                  15

His Ala Thr Gln Ser Glu Gly Ala Ala Ile Thr Tyr Ala Ile Asp Tyr
            20                  25                  30

Asp Thr Met Val Val Asp Pro Ser Leu Glu Ala Val Ser Gln Ser Ala
        35                  40                  45

Leu Val Leu Asn Ala Gln Thr Gly Val Leu Thr Leu Asn Ile Gln Pro
    50                  55                  60

Thr Ala Thr Met His Gly Leu Ile Asn Ile Glu Val Thr Ala Thr Asp
65                  70                  75                  80

Thr Ala Gly Ala Gln Asp Arg Thr Asp Val Thr Val Tyr Val Val Ser
                85                  90                  95

Ser Gln Asn Arg Val Tyr Phe Val Leu Glu His His His His His His
            100                 105                 110
```

<210> SEQ ID NO 9
<211> LENGTH: 336
<212> TYPE: DNA
<213> ORGANISM: Artificial sequence
<220> FEATURE:
<223> OTHER INFORMATION: BtB3 (protease stabilized)

<400> SEQUENCE: 9

```
atggggatat ccacagcgga ctccatcggc agtgagctgc tcagtttaca tgcgacccag    60
```

```
tctgaaggcg cggccattac ttatgctata gactacgata caatggtagt ggaccccagc    120
ctggaggcag tgagtcagtc ggctctcgta ctgaacgctc aaaccggagt gctgacgctt    180
aatatccagc ccacggccac gatgcatgga ctgatcaata tcgaagtcac agctactgac    240
acggccggcg ctcaggaccg caccgacgtc accgtgtacg tggtatcctc gcagaaccgc    300
gtctacttcg tgctcgagca ccaccaccac cactga                              336
```

<210> SEQ ID NO 10
<211> LENGTH: 960
<212> TYPE: DNA
<213> ORGANISM: Artificial sequence
<220> FEATURE:
<223> OTHER INFORMATION: BtB4

<400> SEQUENCE: 10

```
atgcacttgg agcggatatc ggcgactgac ccggacggac tccacgcggg cgtcgtcacc     60
ttccaagtgg taggcgatga ggaatcacaa cggtactttc aagtagttaa cgatggcgcg    120
aacctcggct cgttgaggtt actgcaagcc gttccagagg agatcaggga gttccggata    180
acgattcgcg ctacagacca gggaacggac ccaggaccgc tgtccacgga catgacgttc    240
agagttgttt ttgtgcccac gcaaggagaa cctagattcg cgtcctcaga acatgctgtc    300
gctttcatag aaaagagtgc cggcatggaa gagtctcacc aacttcctct agcacaagac    360
atcaagaacc atctctgtga agacgactgt cacagcattt actatcgtat tatcgatggc    420
aacagcgagg gtcatttcgg cctggatcct gttcgcaaca ggttgttcct gaagaaagag    480
ctgataagag aacaaagtgc ctcccacact ctgcaagtgg cggctagtaa ctcgcccgat    540
ggtggcattc cacttcctgc ttccatcctt actgtcactg ttaccgtgag ggaggcagac    600
cctcgtccag tgtttatgag ggaattgtac accgcaggga tatccacagc ggactccatc    660
ggcagagagc tgctcagatt acatgcgacc cagtctgaag gcgcggccat tacttatgct    720
atagactacg atacaatggt agtggacccc agcctggagg cagtgagaca gtcggctttc    780
gtactgaacg ctcaaaccgg agtgctgacg cttaatatcc agcccacggc cacgatgcat    840
ggactgttca aattcgaagt cacagctact gacacggccg cgctcagga ccgcaccgac    900 gtcaccgtgt acgtggtatc ctcgcagaac cgcctcgagc accaccacca ccactga      960
```

<210> SEQ ID NO 11
<211> LENGTH: 319
<212> TYPE: PRT
<213> ORGANISM: Artificial sequence
<220> FEATURE:
<223> OTHER INFORMATION: BtB4

<400> SEQUENCE: 11

```
Met His Leu Glu Arg Ile Ser Ala Thr Asp Pro Asp Gly Leu His Ala
1               5                   10                  15

Gly Val Val Thr Phe Gln Val Val Gly Asp Glu Glu Ser Gln Arg Tyr
            20                  25                  30

Phe Gln Val Val Asn Asp Gly Ala Asn Leu Gly Ser Leu Arg Leu Leu
        35                  40                  45

Gln Ala Val Pro Glu Glu Ile Arg Glu Phe Arg Ile Thr Ile Arg Ala
    50                  55                  60

Thr Asp Gln Gly Thr Asp Pro Gly Pro Leu Ser Thr Asp Met Thr Phe
65                  70                  75                  80

Arg Val Val Phe Val Pro Thr Gln Gly Glu Pro Arg Phe Ala Ser Ser
                85                  90                  95
```

Glu His Ala Val Ala Phe Ile Glu Lys Ser Ala Gly Met Glu Glu Ser
              100                 105                 110

His Gln Leu Pro Leu Ala Gln Asp Ile Lys Asn His Leu Cys Glu Asp
        115                 120                 125

Asp Cys His Ser Ile Tyr Tyr Arg Ile Asp Gly Asn Ser Glu Gly
    130                 135                 140

His Phe Gly Leu Asp Pro Val Arg Asn Arg Leu Phe Leu Lys Lys Glu
145                 150                 155                 160

Leu Ile Arg Glu Gln Ser Ala Ser His Thr Leu Gln Val Ala Ala Ser
                165                 170                 175

Asn Ser Pro Asp Gly Gly Ile Pro Leu Pro Ala Ser Ile Leu Thr Val
            180                 185                 190

Thr Val Thr Val Arg Glu Ala Asp Pro Arg Pro Val Phe Met Arg Glu
        195                 200                 205

Leu Tyr Thr Ala Gly Ile Ser Thr Ala Asp Ser Ile Gly Arg Glu Leu
    210                 215                 220

Leu Arg Leu His Ala Thr Gln Ser Glu Gly Ala Ala Ile Thr Tyr Ala
225                 230                 235                 240

Ile Asp Tyr Asp Thr Met Val Val Asp Pro Ser Leu Glu Ala Val Arg
                245                 250                 255

Gln Ser Ala Phe Val Leu Asn Ala Gln Thr Gly Val Leu Thr Leu Asn
            260                 265                 270

Ile Gln Pro Thr Ala Thr Met His Gly Leu Phe Lys Phe Glu Val Thr
        275                 280                 285

Ala Thr Asp Thr Ala Gly Ala Gln Asp Arg Thr Asp Val Thr Val Tyr
    290                 295                 300

Val Val Ser Ser Gln Asn Arg Leu Glu His His His His His
305                 310                 315

<210> SEQ ID NO 12
<211> LENGTH: 960
<212> TYPE: DNA
<213> ORGANISM: Artificial sequence
<220> FEATURE:
<223> OTHER INFORMATION: BtB4

<400> SEQUENCE: 12
atgcacttgg agcggatatc ggcgactgac ccggacggac tccacgcggg cgtcgtcacc     60
ttccaagtgg taggcgatga ggaatcacaa cggtactttc aagtagttaa cgatggcgcg    120
aacctcggct cgttgaggtt actgcaagcc gttccagagg agatcaggga gttccggata    180
acgattcgcg ctacagacca gggaacggac ccaggaccgc tgtccacgga catgacgttc    240
agagttgttt ttgtgcccac gcaaggagaa cctagattcg cgtcctcaga acatgctgtc    300
gctttcatag aaaagagtgc cggcatggaa gagtctcacc aacttcctct agcacaagac    360
atcaagaacc atctctgtga agacgactgt cacagcattt actatcgtat tatcgatggc    420
aacagcgagg gtcatttcgg cctggatcct gttcgcaaca ggttgttcct gaagaaagag    480
ctgataagag aacaaagtgc ctcccacact ctgcaagtgg cggctagtaa ctcgcccgat    540
ggtggcattc cacttcctgc ttccatcctt actgtcactg ttaccgtgag ggaggcagac    600
cctcgtccag tgtttatgag ggaattgtac accgcaggga tatccacagc ggactccatc    660
ggcagagagc tgctcagatt acatgcgacc cagtctgaag gcgcggccat tacttatgct    720
atagactacg ataatggt agtggacccc agcctggagg cagtgagaca gtcggctttc    780

```
gtactgaacg ctcaaaccgg agtgctgacg cttaatatcc agcccacggc cacgatgcat    840
ggactgttca aattcgaagt cacagctact gacacggccg gcgctcagga ccgcaccgac    900
gtcaccgtgt acgtggtatc ctcgcagaac cgcctcgagc accaccacca ccaccactga    960
```

<210> SEQ ID NO 13
<211> LENGTH: 960
<212> TYPE: DNA
<213> ORGANISM: Artificial sequence
<220> FEATURE:
<223> OTHER INFORMATION: BtB5 (protease stabilized)

<400> SEQUENCE: 13

```
atgcacctgg aatgtatctc tgcaaccgac ccggatggcc tgcatgctgg tgtagtaact     60
ttccaagtgg ttggtgacga agaaagccag gcttatttcc aggttgttaa cgacggtgca    120
aacctgggct cccttttccct gctgcaggcc gtgccag

```
His Gln Leu Pro Leu Ala Gln Asp Ile Ala Asn His Leu Cys Glu Asp
            115                 120                 125

Asp Cys His Ser Ile Tyr Tyr Ala Ile Ile Asp Gly Asn Ser Glu Gly
        130                 135                 140

His Phe Gly Leu Asp Pro Val Ala Asn Ala Leu Phe Leu Ser Ala Glu
145                 150                 155                 160

Leu Ile Ala Glu Gln Ser Ala Ser His Thr Leu Gln Val Ala Ala Ser
                165                 170                 175

Asn Ser Pro Asp Gly Gly Ile Pro Leu Pro Ala Ser Ile Leu Thr Val
            180                 185                 190

Thr Val Thr Val Ala Glu Ala Asp Pro Ala Pro Val Phe Met Ala Glu
            195                 200                 205

Leu Tyr Thr Ala Gly Ile Ser Thr Ala Asp Ser Ile Gly Cys Glu Leu
        210                 215                 220

Leu Ala Leu His Ala Thr Gln Ser Glu Gly Ala Ala Ile Thr Tyr Ala
225                 230                 235                 240

Ile Asp Tyr Asp Thr Met Val Val Asp Pro Ser Leu Glu Ala Val Cys
                245                 250                 255

Gln Ser Ala Phe Val Leu Asn Ala Gln Thr Gly Val Leu Thr Leu Asn
            260                 265                 270

Ile Gln Pro Thr Ala Thr Met His Gly Leu Phe Asn Phe Glu Val Thr
        275                 280                 285

Ala Thr Asp Thr Ala Gly Ala Gln Asp Arg Thr Asp Val Thr Val Tyr
290                 295                 300

Val Val Ser Ser Gln Asn Arg Leu Glu His His His His His
305                 310                 315

<210> SEQ ID NO 15
<211> LENGTH: 960
<212> TYPE: DNA
<213> ORGANISM: Artificial sequence
<220> FEATURE:
<223> OTHER INFORMATION: BtB5 (protease stabilized)

<400> SEQUENCE: 15
atgcacctgg aatgtatctc tgcaaccgac ccggatggcc tgcatgctgg tgtagtaact    60
ttccaagtgg ttggtgacga agaaagccag gcttatttcc aggttgttaa cgacggtgca   120
aacctgggct ccctttccct gctgcaggcc gtgccagaag aaatcgcaga gttcagcatt   180
accatctgcg ctaccgacca aggtaccgac ccgggcccgc tgagcaccga catgaccttc   240
gctgttgtat tcgttcctac tcagggtgaa ccagctttcg cttcctctga gcacgcagta   300
gcattcatcg aagcctccgc gggtatggaa gaatctcatc agctcccact ggctcaagat   360
atcgcgaacc atctgtgtga agacgactgc cactctatct actacgctat catcgacggt   420
aacagcgaag gtcacttcgg tctggacccg gtagctaacg cgctgttcct gtctgctgaa   480
ctgatcgcgg aacagagcgc ttctcacact ttacaagttg ctgcgtccaa cagcccggac   540
ggtggcatcc ctctgcctgc atctatcctt accgttaccg taaccgtcgc tgaagcagat   600
ccagcaccgg tattcatggc tgagctgtac acggctggca tcagcactgc cgactccatt   660
ggctgcgaac ttctggctct gcatgcgact cagtcagaag cgcggccat cacctatgct   720 atcgactatg ataccatggt agttgatccg tctctggaag cagtttgcca gtctgctttc   780
gttctgaacg cacagactgg tgttctgact ctgaacatcc agccgactgc aacgatgcat   840
ggtctgttca acttcgaagt tactgcgacc gacactgcgg gcgctcagga ccgtactgac   900
```

```
gttaccgtct acgtagtgtc ttctcagaac cgtctggaac accaccacca ccaccactaa    960
```

<210> SEQ ID NO 16
<211> LENGTH: 1824
<212> TYPE: DNA
<213> ORGANISM: Manduca sexta

<400> SEQUENCE: 16

```
gaattcgaag gaaatatcac aatccacatc accgacacga acaacaaggt cccgcaggcg     60
gaaacgacta agttcgatac cgtcgtgtat atttacgaga acgcaaccca cttggacgag    120
gtggtcactc tgatagccag tgatcttgac agagacgaaa tataccacac ggtgagctac    180
gtcatcaatt acgcagtgaa ccctcgactg atgaacttct tctccgtgaa ccgggagacc    240
ggcctggtgt acgtagacta tgagaccag gggagtggcg aggtgctgga ccgtgatggt    300
gatgaaccaa cgcaccgtat cttcttcaac ctcatcgaca acttcatggg ggaaggagaa    360
ggtaacagaa atcagaacga cacagaagtt ctcgttatct tgttggatgt aatgacaat    420
gctcctgaat tgccaccgcc gagcgaactc tcttggacta tatctgagaa ccttaagcag    480
ggcgtccgtc ttgaaccgca tatcttcgcc ccggaccgcg acgagcccga cacggacaac    540
tccagggtcg gttacgagat cctgaacctc agcacggagc gggacatcga agtgccggag    600
ctgtttgtaa tgatacagat cgcgaacgtc acgggagagc tggagaccgc catggacctc    660
aagggatatt gggggacgta cgctatacat atacgggcat cgaccacgg cattccgcaa    720
atgtccatga acgagacata tgagctgatt atccatccgt tcaactacta cgcgcctgag    780
ttcgtcttcc cgaccaacga tgccgtcata cgacttgcga gggaacgagc tgtaatcaat    840
ggagttctag cgacagtgaa cggagagttc ttggagcgga tatcggcgac tgacccggac    900
ggactccacg cgggcgtcgt caccttccaa gtggtaggcg atgaggaatc acaacggtac    960
tttcaagtag ttaacgatgg cgcgaacctc ggctcgttga ggttactgca agccgttcca   1020
gaggagatca gggagttccg gataacgatt cgcgctacag accagggaac ggacccagga   1080
ccgctgtcca cggacatgac gttcagagtt gttttttgtgc ccacgcaagg agaacctaga   1140
ttcgcgtcct cagaacatgc tgtcgctttc atagaaaaga gtgccggcat ggaagagtct   1200
caccaacttc ctctagcaca agacatcaag aaccatctct gtgaagacga ctgtcacagc   1260
atttactatc gtattatcga tggcaacagc gagggtcatt tcggcctgga tcctgttcgc   1320
aacaggttgt tcctgaagaa agagctgata agagaacaaa gtgcctccca cactctgcaa   1380
gtggcggcta gtaactcgcc cgatggtggc attccacttc ctgcttccat ccttactgtc   1440
actgttaccg tgagggaggc agaccctcgt ccagtgttta tgagggaatt gtacaccgca   1500
gggatatcca cagcggactc catcggcaga gagctgctca gattacatgc gacccagtct   1560
gaaggcgcgg ccattactta tgctatagac tacgatacaa tggtagtgga ccccagcctg   1620
gaggcagtga gacagtcggc tttcgtactg aacgctcaaa ccggagtgct gacgcttaat   1680
atccagccca cggccacgat gcatggactg ttcaaattcg aagtcacagc tactgacacg   1740
gccggcgctc aggaccgcac cgacgtcacc gtgtacgtgg tatcctcgca gaaccgcctc   1800
gagcaccacc accaccacca ctga                                          1824
```

<210> SEQ ID NO 17
<211> LENGTH: 607
<212> TYPE: PRT
<213> ORGANISM: Manduca sexta

<400> SEQUENCE: 17

```
Glu Phe Glu Gly Asn Ile Thr Ile His Ile Thr Asp Thr Asn Asn Lys
1               5                   10                  15
Val Pro Gln Ala Glu Thr Thr Lys Phe Asp Thr Val Val Tyr Ile Tyr
                20                  25                  30
Glu Asn Ala Thr His Leu Asp Glu Val Val Thr Leu Ile Ala Ser Asp
                35                  40                  45
Leu Asp Arg Asp Glu Ile Tyr His Thr Val Ser Tyr Val Ile Asn Tyr
50                  55                  60
Ala Val Asn Pro Arg Leu Met Asn Phe Phe Ser Val Asn Arg Glu Thr
65                  70                  75                  80
Gly Leu Val Tyr Val Asp Tyr Glu Thr Gln Gly Ser Gly Glu Val Leu
                85                  90                  95
Asp Arg Asp Gly Asp Glu Pro Thr His Arg Ile Phe Phe Asn Leu Ile
                100                 105                 110
Asp Asn Phe Met Gly Glu Gly Glu Gly Asn Arg Asn Gln Asn Asp Thr
                115                 120                 125
Glu Val Leu Val Ile Leu Leu Asp Val Asn Asp Asn Ala Pro Glu Leu
                130                 135                 140
Pro Pro Pro Ser Glu Leu Ser Trp Thr Ile Ser Glu Asn Leu Lys Gln
145                 150                 155                 160
Gly Val Arg Leu Glu Pro His Ile Phe Ala Pro Asp Arg Asp Glu Pro
                165                 170                 175
Asp Thr Asp Asn Ser Arg Val Gly Tyr Glu Ile Leu Asn Leu Ser Thr
                180                 185                 190
Glu Arg Asp Ile Glu Val Pro Glu Leu Phe Val Met Ile Gln Ile Ala
                195                 200                 205
Asn Val Thr Gly Glu Leu Glu Thr Ala Met Asp Leu Lys Gly Tyr Trp
210                 215                 220
Gly Thr Tyr Ala Ile His Ile Arg Ala Phe Asp His Gly Ile Pro Gln
225                 230                 235                 240
Met Ser Met Asn Glu Thr Tyr Glu Leu Ile Ile His Pro Phe Asn Tyr
                245                 250                 255
Tyr Ala Pro Glu Phe Val Phe Pro Thr Asn Asp Ala Val Ile Arg Leu
                260                 265                 270
Ala Arg Glu Arg Ala Val Ile Asn Gly Val Leu Ala Thr Val Asn Gly
                275                 280                 285
Glu Phe Leu Glu Arg Ile Ser Ala Thr Asp Pro Asp Gly Leu His Ala
                290                 295                 300
Gly Val Val Thr Phe Gln Val Val Gly Asp Glu Ser Gln Arg Tyr
305                 310                 315                 320
Phe Gln Val Val Asn Asp Gly Ala Asn Leu Gly Ser Leu Arg Leu Leu
                325                 330                 335
Gln Ala Val Pro Glu Glu Ile Arg Glu Phe Arg Ile Thr Ile Arg Ala
                340                 345                 350
Thr Asp Gln Gly Thr Asp Pro Gly Pro Leu Ser Thr Asp Met Thr Phe
                355                 360                 365
Arg Val Val Phe Val Pro Thr Gln Gly Glu Pro Arg Phe Ala Ser Ser
370                 375                 380
Glu His Ala Val Ala Phe Ile Glu Lys Ser Ala Gly Met Glu Glu Ser
385                 390                 395                 400
His Gln Leu Pro Leu Ala Gln Asp Ile Lys Asn His Leu Cys Glu Asp
                405                 410                 415
```

```
Asp Cys His Ser Ile Tyr Tyr Arg Ile Ile Asp Gly Asn Ser Glu Gly
                420                 425                 430

His Phe Gly Leu Asp Pro Val Arg Asn Arg Leu Phe Leu Lys Lys Glu
            435                 440                 445

Leu Ile Arg Glu Gln Ser Ala Ser His Thr Leu Gln Val Ala Ala Ser
450                 455                 460

Asn Ser Pro Asp Gly Gly Ile Pro Leu Pro Ala Ser Ile Leu Thr Val
465                 470                 475                 480

Thr Val Thr Val Arg Glu Ala Asp Pro Arg Pro Val Phe Met Arg Glu
                485                 490                 495

Leu Tyr Thr Ala Gly Ile Ser Thr Ala Asp Ser Ile Gly Arg Glu Leu
            500                 505                 510

Leu Arg Leu His Ala Thr Gln Ser Glu Gly Ala Ala Ile Thr Tyr Ala
        515                 520                 525

Ile Asp Tyr Asp Thr Met Val Val Asp Pro Ser Leu Glu Ala Val Arg
    530                 535                 540

Gln Ser Ala Phe Val Leu Asn Ala Gln Thr Gly Val Leu Thr Leu Asn
545                 550                 555                 560

Ile Gln Pro Thr Ala Thr Met His Gly Leu Phe Lys Phe Glu Val Thr
                565                 570                 575

Ala Thr Asp Thr Ala Gly Ala Gln Asp Arg Thr Asp Val Thr Val Tyr
            580                 585                 590

Val Val Ser Ser Gln Asn Arg Leu Glu His His His His His His
        595                 600                 605

<210> SEQ ID NO 18
<211> LENGTH: 1824
<212> TYPE: DNA
<213> ORGANISM: Manduca sexta

<400> SEQUENCE: 18
gaattcgaag gaaatatcac aatccacatc accgacacga acaacaaggt cccgcaggcg      60
gaaacgacta agttcgatac cgtcgtgtat atttacgaga acgaacccca cttggacgag     120
gtggtcactc tgatagccag tgatcttgac agagacgaaa tataccacac ggtgagctac     180
gtcatcaatt acgcagtgaa ccctcgactg atgaacttct tctccgtgaa ccgggagacc     240
ggcctggtgt acgtagacta tgagacccag gggagtggcg aggtgctgga ccgtgatggt     300
gatgaaccaa cgcaccgtat cttcttcaac ctcatcgaca cttcatgggg gaaggagaa      360 ggtaacagaa atcagaacga cacagaagtt ctcgttatct tgttggatgt gaatgacaat     420
gctcctgaat tgccaccgcc gagcgaactc tcttggacta tatctgagaa ccttaagcag     480
ggcgtccgtc ttgaaccgca tatcttcgcc ccggaccgcg acgagcccga cacgacaaac     540
tccagggtcg gttacgagat cctgaacctc agcacggagc gggacatcga agtgccggag     600
ctgtttgtaa tgatacagat cgcgaacgtc acgggagagc tggagaccgc catggacctc     660
aagggatatt gggggacgta cgctatacat atacgggcat cgaccacgg cattccgcaa     720 atgtccatga acgagacata tgagctgatt atccatccgt tcaactacta cgcgcctgag     780
ttcgtcttcc cgaccaacga tgccgtcata cgacttgcga gggaacgagc tgtaatcaat     840
ggagttctag cgacagtgaa cggagagttc ttggagcgga tatcggcgac tgacccggac     900
ggactccacg cgggcgtcgt caccttccaa gtggtaggcg atgaggaatc acaacggtac     960
tttcaagtag ttaacgatgg cgcgaacctc ggctcgttga ggttactgca agccgttcca    1020
gaggagatca gggagttccg gataacgatt cgcgctacag accagggaac ggacccagga    1080
```

```
ccgctgtcca cggacatgac gttcagagtt gtttttgtgc ccacgcaagg agaacctaga   1140
ttcgcgtcct cagaacatgc tgtcgctttc atagaaaaga gtgccggcat ggaagagtct   1200
caccaacttc ctctagcaca agacatcaag aaccatctct gtgaagacga ctgtcacagc   1260
atttactatc gtattatcga tggcaacagc gagggtcatt tcggcctgga tcctgttcgc   1320
aacaggttgt tcctgaagaa agagctgata agagaacaaa gtgcctccca cactctgcaa   1380
gtggcggcta gtaactcgcc cgatggtggc attccacttc ctgcttccat ccttactgtc   1440
actgttaccg tgagggaggc agaccctcgt ccagtgttta tgagggaatt gtacaccgca   1500
gggatatcca gcggactc catcggcaga gagctgctca gattacatgc gacccagtct    1560
gaaggcgcgg ccattactta tgctatagac tacgatacaa tggtagtgga ccccagcctg   1620
gaggcagtga cagtcggc tttcgtactg aacgctcaaa ccggagtgct gacgcttaat    1680
atccagccca cggccacgat gcatggactg ttcaaattcg aagtcacagc tactgacacg   1740
gccggcgctc aggaccgcac cgacgtcacc gtgtacgtgg tatcctcgca gaaccgcctc   1800
gagcaccacc accaccacca ctga                                          1824
```

```
<210> SEQ ID NO 19
<211> LENGTH: 1173
<212> TYPE: DNA
<213> ORGANISM: Manduca sexta

<400> SEQUENCE: 19
```

```
atggacctca agggatattg ggggacgtac gctatacata tacgggcatt cgaccacggc     60
attccgcaaa tgtccatgaa cgagacatat gagctgatta tccatccgtt caactactac   120
gcgcctgagt tcgtcttccc gaccaacgat gccgtcatac gacttgcgag ggaacgagct   180
gtaatcaatg gagttctagc gacagtgaac ggagagttct ggagcggat atcggcgact    240 gacccggacg gactccacgc gggcgtcgtc accttccaag tggtaggcga tgaggaatca   300
caacggtact ttcaagtagt taacgatggc gcgaacctcg gctcgttgag gttactgcaa   360
gccgttccag aggagatcag ggagttccgg ataacgattc gcgctacaga ccagggaacg   420
gacccaggac cgctgtccac ggacatgacg ttcagagttg tttttgtgcc cacgcaagga   480
gaacctagat cgcgtcctc agaacatgct gtcgctttca tagaaaagag tgccggcatg   540
gaagagtctc accaacttcc tctagcacaa gacatcaaga accatctctg tgaagacgac   600
tgtcacagca tttactatcg tattatcgat ggcaacagcg agggtcattt cggcctggat   660
cctgttcgca acaggttgtt cctgaagaaa gagctgataa gagaacaaag tgcctcccac   720
actctgcaag tggcggctag taactcgccc gatggtggca ttccacttcc tgcttccatc   780
cttactgtca ctgttaccgt gagggaggca gaccctcgtc cagtgtttat gagggaattg   840
tacaccgcag ggatatccac agcggactcc atcggcagag agctgctcag attacatgcg   900
acccagtctg aaggcgcggc cattacttat gctatagact acgatacaat ggtagtggac   960
cccagcctgg aggcagtgag acagtcggct ttcgtactga acgctcaaac cggagtgctg  1020
acgcttaata tccagcccac ggccacgatg catggactgt tcaaattcga agtcacagct  1080
actgacacgg ccggcgctca ggaccgcacc gacgtcaccg tgtacgtggt atcctcgcag  1140
aaccgcctcg agcaccacca ccaccaccac tga                                1173
```

```
<210> SEQ ID NO 20
<211> LENGTH: 390
<212> TYPE: PRT
```

<213> ORGANISM: Manduca sexta

<400> SEQUENCE: 20

```
Met Asp Leu Lys Gly Tyr Trp Gly Thr Tyr Ala Ile His Ile Arg Ala
1               5                   10                  15
Phe Asp His Gly Ile Pro Gln Met Ser Met Asn Glu Thr Tyr Glu Leu
                20                  25                  30
Ile Ile His Pro Phe Asn Tyr Tyr Ala Pro Glu Phe Val Phe Pro Thr
            35                  40                  45
Asn Asp Ala Val Ile Arg Leu Ala Arg Glu Arg Ala Val Ile Asn Gly
        50                  55                  60
Val Leu Ala Thr Val Asn Gly Glu Phe Leu Glu Arg Ile Ser Ala Thr
65                  70                  75                  80
Asp Pro Asp Gly Leu His Ala Gly Val Val Thr Phe Gln Val Val Gly
                85                  90                  95
Asp Glu Glu Ser Gln Arg Tyr Phe Gln Val Val Asn Asp Gly Ala Asn
                100                 105                 110
Leu Gly Ser Leu Arg Leu Leu Gln Ala Val Pro Glu Glu Ile Arg Glu
            115                 120                 125
Phe Arg Ile Thr Ile Arg Ala Thr Asp Gln Gly Thr Asp Pro Gly Pro
    130                 135                 140
Leu Ser Thr Asp Met Thr Phe Arg Val Val Phe Val Pro Thr Gln Gly
145                 150                 155                 160
Glu Pro Arg Phe Ala Ser Ser Glu His Ala Val Ala Phe Ile Glu Lys
                165                 170                 175
Ser Ala Gly Met Glu Glu Ser His Gln Leu Pro Leu Ala Gln Asp Ile
            180                 185                 190
Lys Asn His Leu Cys Glu Asp Cys His Ser Ile Tyr Tyr Arg Ile
        195                 200                 205
Ile Asp Gly Asn Ser Glu Gly His Phe Gly Leu Asp Pro Val Arg Asn
    210                 215                 220
Arg Leu Phe Leu Lys Lys Glu Leu Ile Arg Glu Gln Ser Ala Ser His
225                 230                 235                 240
Thr Leu Gln Val Ala Ala Ser Asn Ser Pro Asp Gly Gly Ile Pro Leu
                245                 250                 255
Pro Ala Ser Ile Leu Thr Val Thr Val Thr Val Arg Glu Ala Asp Pro
            260                 265                 270
Arg Pro Val Phe Met Arg Glu Leu Tyr Thr Ala Gly Ile Ser Thr Ala
    275                 280                 285
Asp Ser Ile Gly Arg Glu Leu Leu Arg Leu His Ala Thr Gln Ser Glu
    290                 295                 300
Gly Ala Ala Ile Thr Tyr Ala Ile Asp Tyr Asp Thr Met Val Val Asp
305                 310                 315                 320
Pro Ser Leu Glu Ala Val Arg Gln Ser Ala Phe Val Leu Asn Ala Gln
                325                 330                 335
Thr Gly Val Leu Thr Leu Asn Ile Gln Pro Thr Ala Thr Met His Gly
            340                 345                 350
Leu Phe Lys Phe Glu Val Thr Ala Thr Asp Thr Ala Gly Ala Gln Asp
        355                 360                 365
Arg Thr Asp Val Thr Val Tyr Val Val Ser Ser Gln Asn Arg Leu Glu
    370                 375                 380
His His His His His His
385                 390
```

<210> SEQ ID NO 21
<211> LENGTH: 1173
<212> TYPE: DNA
<213> ORGANISM: Manduca sexta

<400> SEQUENCE: 21

| | | | | | |
|---|---|---|---|---|---|
| atggacctca | agggatattg | ggggacgtac | gctatacata | tacgggcatt | cgaccacggc | 60 |
| attccgcaaa | tgtccatgaa | cgagacatat | gagctgatta | tccatccgtt | caactactac | 120 |
| gcgcctgagt | tcgtcttccc | gaccaacgat | gccgtcatac | gacttgcgag | ggaacgagct | 180 |
| gtaatcaatg | gagttctagc | gacagtgaac | ggagagttct | ggagcggat | atcggcgact | 240 |
| gacccggacg | gactccacgc | gggcgtcgtc | accttccaag | tggtaggcga | tgaggaatca | 300 |
| caacggtact | ttcaagtagt | taacgatggc | gcgaacctcg | gctcgttgag | gttactgcaa | 360 |
| gccgttccag | aggagatcag | ggagttccgg | ataacgattc | gcgctacaga | ccagggaacg | 420 |
| gacccaggac | cgctgtccac | ggacatgacg | ttcagagttg | tttttgtgcc | cacgcaagga | 480 |
| gaacctagat | tcgcgtcctc | agaacatgct | gtcgctttca | tagaaaagag | tgccggcatg | 540 |
| gaagagtctc | accaacttcc | tctagcacaa | gacatcaaga | accatctctg | tgaagacgac | 600 |
| tgtcacagca | tttactatcg | tattatcgat | ggcaacagcg | agggtcattt | cggcctggat | 660 |
| cctgttcgca | acaggttgtt | cctgaagaaa | gagctgataa | gagaacaaag | tgcctcccac | 720 |
| actctgcaag | tggcggctag | taactcgccc | gatggtggca | ttccacttcc | tgcttccatc | 780 |
| cttactgtca | ctgttaccgt | gagggaggca | gaccctcgtc | cagtgtttat | gagggaattg | 840 |
| tacaccgcag | ggatatccac | agcggactcc | atcggcagag | agctgctcag | attacatgcg | 900 |
| acccagtctg | aaggcgcggc | cattacttat | gctatagact | acgatacaat | ggtagtggac | 960 |
| cccagcctgg | aggcagtgag | acagtcggct | ttcgtactga | acgctcaaac | cggagtgctg | 1020 |
| acgcttaata | tccagcccac | ggccacgatg | catggactgt | tcaaattcga | agtcacagct | 1080 |
| actgacacgg | ccggcgctca | ggaccgcacc | gacgtcaccg | tgtacgtggt | atcctcgcag | 1140 |
| aaccgcctcg | agcaccacca | ccaccaccac | tga | | | 1173 |

<210> SEQ ID NO 22
<211> LENGTH: 675
<212> TYPE: DNA
<213> ORGANISM: Manduca sexta

<400> SEQUENCE: 22

| | | | | | |
|---|---|---|---|---|---|
| atgcaccatg | ctgtcgcttt | catagaaaag | agtgccggca | tggaagagtc | tcaccaactt | 60 |
| cctctagcac | aagacatcaa | gaaccatctc | tgtgaagacg | actgtcacag | catttactat | 120 |
| cgtattatcg | atggcaacag | cgagggtcat | ttcggcctgg | atcctgttcg | caacaggttg | 180 |
| ttcctgaaga | aagagctgat | aagagaacaa | agtgcctccc | acactctgca | agtggcggct | 240 |
| agtaactcgc | ccgatggtgg | cattccactt | cctgcttcca | tccttactgt | cactgttacc | 300 |
| gtgagggagg | cagaccctcg | tccagtgttt | atgagggaat | gtacaccgc | agggatatcc | 360 |
| acagcggact | ccatcggcag | agagctgctc | agattacatg | cgacccagtc | tgaaggcgcg | 420 |
| gccattactt | atgctataga | ctacgataca | atggtagtgg | accccagcct | ggaggcagtg | 480 |
| agacagtcgg | ctttcgtact | gaacgctcaa | accggagtgc | tgacgcttaa | tatccagccc | 540 |
| acggccacga | tgcatggact | gttcaaattc | gaagtcacag | ctactgacac | ggccggcgct | 600 |
| caggaccgca | ccgacgtcac | cgtgtacgtg | gtatcctcgc | agaaccgcct | cgagcaccac | 660 |
| caccaccacc | actga | | | | | 675 |

<210> SEQ ID NO 23
<211> LENGTH: 224
<212> TYPE: PRT
<213> ORGANISM: Manduca sexta

<400> SEQUENCE: 23

```
Met His His Ala Val Ala Phe Ile Glu Lys Ser Ala Gly Met Glu Glu
1               5                   10                  15

Ser His Gln Leu Pro Leu Ala Gln Asp Ile Lys Asn His Leu Cys Glu
            20                  25                  30

Asp Asp Cys His Ser Ile Tyr Tyr Arg Ile Ile Asp Gly Asn Ser Glu
        35                  40                  45

Gly His Phe Gly Leu Asp Pro Val Arg Asn Arg Leu Phe Leu Lys Lys
    50                  55                  60

Glu Leu Ile Arg Glu Gln Ser Ala Ser His Thr Leu Gln Val Ala Ala
65                  70                  75                  80

Ser Asn Ser Pro Asp Gly Gly Ile Pro Leu Pro Ala Ser Ile Leu Thr
                85                  90                  95

Val Thr Val Thr Val Arg Glu Ala Asp Pro Arg Pro Val Phe Met Arg
            100                 105                 110

Glu Leu Tyr Thr Ala Gly Ile Ser Thr Ala Asp Ser Ile Gly Arg Glu
        115                 120                 125

Leu Leu Arg Leu His Ala Thr Gln Ser Glu Gly Ala Ala Ile Thr Tyr
    130                 135                 140

Ala Ile Asp Tyr Asp Thr Met Val Val Asp Pro Ser Leu Glu Ala Val
145                 150                 155                 160

Arg Gln Ser Ala Phe Val Leu Asn Ala Gln Thr Gly Val Leu Thr Leu
                165                 170                 175

Asn Ile Gln Pro Thr Ala Thr Met His Gly Leu Phe Lys Phe Glu Val
            180                 185                 190

Thr Ala Thr Asp Thr Ala Gly Ala Gln Asp Arg Thr Asp Val Thr Val
        195                 200                 205

Tyr Val Val Ser Ser Gln Asn Arg Leu Glu His His His His His
    210                 215                 220
```

<210> SEQ ID NO 24
<211> LENGTH: 675
<212> TYPE: DNA
<213> ORGANISM: Manduca sexta

<400> SEQUENCE: 24

```
atgcaccatg ctgtcgcttt catagaaaag agtgccggca tggaagagtc tcaccaactt      60
cctctagcac aagacatcaa gaaccatctc tgtgaagacg actgtcacag catttactat     120
cgtattatcg atggcaacag cgagggtcat ttcggcctgg atcctgttcg aacaggttg      180 ttcctgaaga aagagctgat aagagaacaa agtgcctccc acactctgca agtggcggct     240
agtaactcgc cgatggtgg cattccactt cctgcttcca tccttactgt cactgttacc      300
gtgagggagg cagaccctcg tccagtgttt atgagggaat tgtacaccgc agggatatcc     360
acagcggact ccatcggcag agagctgctc agattacatg cgacccagtc tgaaggcgcg     420
gccattactt atgctataga ctacgataca atggtagtgg accccagcct ggaggcagtg     480
agacagtcgg ctttcgtact gaacgctcaa accggagtgc tgacgcttaa tatccagccc     540
acggccacga tgcatggact gttcaaattc gaagtcacag ctactgacac ggccggcgct     600
```
caggaccgca ccgacgtcac cgtgtacgtg gtatcctcgc agaaccgcct cgagcaccac 660
caccaccacc actga 675

<210> SEQ ID NO 25
<211> LENGTH: 960
<212> TYPE: DNA
<213> ORGANISM: Artificial sequence
<220> FEATURE:
<223> OTHER INFORMATION: BtB9 version of Spodoptera frugiperda cadherin
repeats

<400> SEQUENCE: 25

```
atgaaattcc tggaccgtct gtccgcaact gacgaagacg gcctgcacgc gggccgtgta    60
actttctcta tcgctggcaa cgacgaggct gcagaatact tcaacgttct gaacgacggc   120
gataactccg ctatgctgac cctgaaacag gcgctgccgg ctggtgtaca gcagttcgaa   180
ctggtgattc gcgctactga cggcggtacc gaaccgggcc cgcgttctac cgactgtagc   240
gtaaccgttt ttttcgttat gacccagggt gacccggttt tcgacgataa cgcagcatct   300
gttcgctttg tagaaaagga agcaggtatg tccgaaaagt tccagctgcc acaggctgat   360
gacccgaaga actatcgttg tatggacgac tgccacacta tttactactc catcgttgac   420
ggtaacgacg gtgaccactt cgcagttgaa ccggagacca acgtaatcta cctgctgaaa   480
ccgctggacc gttctcagca ggaacagtat cgtgttgttg tagcagcatc caacaccgcca   540 ggtggcacta gtactctgtc ttcctccctg ctgaccgtta ctatcggtgt acgtgaagcg   600
aatccgcgtc cgattttcga atccgaattt tacaccgcgg gtgtactgca caccgactcc   660
atccacaaag aactggttta tctggcggca aaacacagcg aaggtctgcc aatcgtttac   720
tctattgacc aggaaaccat gaaaattgat gaatcactgc agactgttgt agaagatgcg   780
ttcgacatca actccgctac cggtgttatc tctctgaact tccagcctac cagcgttatg   840
catggcagct tcgatttcga agttgttgca tctgacaccc gcggcgctag cgaccgtgcc   900
aaagtaagca tttacatgat ctctacccgc gttcgcgtac accaccacca tcaccactaa   960
```

<210> SEQ ID NO 26
<211> LENGTH: 319
<212> TYPE: PRT
<213> ORGANISM: Artificial sequence
<220> FEATURE:
<223> OTHER INFORMATION: BtB9 version of Spodoptera frugiperda cadherin
repeats

<400> SEQUENCE: 26

```
Met Lys Phe Leu Asp Arg Leu Ser Ala Thr Asp Glu Asp Gly Leu His
 1               5                  10                  15

Ala Gly Arg Val Thr Phe Ser Ile Ala Gly Asn Asp Glu Ala Ala Glu
            20                  25                  30

Tyr Phe Asn Val Leu Asn Asp Gly Asp Asn Ser Ala Met Leu Thr Leu
        35                  40                  45

Lys Gln Ala Leu Pro Ala Gly Val Gln Gln Phe Glu Leu Val Ile Arg
    50                  55                  60

Ala Thr Asp Gly Gly Thr Glu Pro Gly Pro Arg Ser Thr Asp Cys Ser
65                  70                  75                  80

Val Thr Val Val Phe Val Met Thr Gln Gly Asp Pro Val Phe Asp Asp
                85                  90                  95

Asn Ala Ala Ser Val Arg Phe Val Glu Lys Glu Ala Gly Met Ser Glu
            100                 105                 110
```

```
Lys Phe Gln Leu Pro Gln Ala Asp Asp Pro Lys Asn Tyr Arg Cys Met
            115                 120                 125
Asp Asp Cys His Thr Ile Tyr Tyr Ser Ile Val Asp Gly Asn Asp Gly
130                 135                 140
Asp His Phe Ala Val Glu Pro Glu Thr Asn Val Ile Tyr Leu Leu Lys
145                 150                 155                 160
Pro Leu Asp Arg Ser Gln Gln Glu Gln Tyr Arg Val Val Ala Ala
                165                 170                 175
Ser Asn Thr Pro Gly Gly Thr Ser Thr Leu Ser Ser Ser Leu Leu Thr
            180                 185                 190
Val Thr Ile Gly Val Arg Glu Ala Asn Pro Arg Pro Ile Phe Glu Ser
            195                 200                 205
Glu Phe Tyr Thr Ala Gly Val Leu His Thr Asp Ser Ile His Lys Glu
            210                 215                 220
Leu Val Tyr Leu Ala Ala Lys His Ser Glu Gly Leu Pro Ile Val Tyr
225                 230                 235                 240
Ser Ile Asp Gln Glu Thr Met Lys Ile Asp Ser Leu Gln Thr Val
                245                 250                 255
Val Glu Asp Ala Phe Asp Ile Asn Ser Ala Thr Gly Val Ile Ser Leu
            260                 265                 270
Asn Phe Gln Pro Thr Ser Val Met His Gly Ser Phe Asp Phe Glu Val
            275                 280                 285
Val Ala Ser Asp Thr Arg Gly Ala Ser Asp Arg Ala Lys Val Ser Ile
            290                 295                 300
Tyr Met Ile Ser Thr Arg Val Arg Val His His His His His
305                 310                 315
```

<210> SEQ ID NO 27
<211> LENGTH: 960
<212> TYPE: DNA
<213> ORGANISM: Artificial sequence
<220> FEATURE:
<223> OTHER INFORMATION: BtB9 version of Spodoptera frugiperda cadherin
    repeats

<400> SEQUENCE: 27

```
atgaaattcc tggaccgtct gtccgcaact gacgaagacg cctgcacgc gggccgtgta    60 actttctcta tcgctggcaa cgacgaggct gcagaatact tcaacgttct gaacgacggc   120
gataactccg ctatgctgac cctgaaacag gcgctgccgg ctggtgtaca gcagttcgaa   180
ctggtgattc gcgctactga cggcggtacc gaacccgggc cgcgttctac cgactgtagc   240
gtaaccgttg ttttcgttat gacccagggt gacccggttt cgacgataa cgcagcatct   300 gttcgctttg tagaaaagga agcaggtatg tccgaaaagt tccagctgcc acaggctgat   360
gacccgaaga actatcgttg tatggacgac tgccacacta tttactactc catcgttgac   420
ggtaacgacg gtgaccactt cgcagttgaa ccggagacca cgtaatcta cctgctgaaa   480 ccgctggacc gttctcagca ggaacagtat cgtgttgttg tagcagcatc caacaccca   540 ggtggcacta gtactctgtc ttcctccctg ctgaccgtta ctatcggtgt acgtgaagcg   600
aatccgcgtc cgattttcga atccgaattt tacaccgcgg gtgtactgca caccgactcc   660
atccacaaag aactggttta tctggcggca aaacacagcg aaggtctgcc aatcgtttac   720
tctattgacc aggaaaccat gaaaattgat gaatcactgc agactgttgt agaagatgcg   780
ttcgacatca actccgctac cggtgttatc tctctgaact tccagccta cagcgttatg   840 catggcagct cgatttcga agttgttgca tctgacaccc gcggcgctag cgaccgtgcc   900
```

```
aaagtaagca tttacatgat ctctacccgc gttcgcgtac accaccacca tcaccactaa    960
```

<210> SEQ ID NO 28
<211> LENGTH: 960
<212> TYPE: DNA
<213> ORGANISM: Artificial sequence
<220> FEATURE:
<223> OTHER INFORMATION: BtB10 (protease stabilized)

<400> SEQUENCE: 28

```
atggcatttc tggattgtct gtctgcaact gatgaagatg gtctgcatgc tggttgtgtc     60
accttcagta ttgctggcaa tgatgaggca gcagaatatt ttaatgtact gaatgatggt    120
gacaactctg ctatgctgac cctgtcccag ctctgccag ctggtgttca gcagtttgag     180
ctggttatct ctgctactga tggtggtact gaaccaggcc catctagcac tgactgcagt    240
gttactgttg tatttgttat gacccagggt gacccagtat tgatgacaa cgcagcttct     300
gtttcctttg ttgaacatga agctggtatg tctgagtcct tccagctgcc acaggctgat    360
gacccatcta actatgcttg tatggatgac tgccacacta tctactactc tattgtagat    420
ggtaacgatg gtgatcattt tgctgttgaa ccagaaacca acgtaattta tctgctgagc    480
ccactggact cttctcagca ggaacagtac tctgtagttg ttgcagcttc caacacccca    540
ggtggtacat ccaccctgtc ttcttccctg ctgactgtta ctattggtgt atctgaagct    600
aacccatccc cgatctttga aagtgaattt tacactgctg gtgttctgca cactgactct    660
attcattctg aactggttta cctggcagct tctcactctg aaggtctccc aattgtatat    720
tctattgacc aggaaaactat gtcaattgat gaatctctgc agactgtggt ggaagatgct    780
ttcgacatca actctgcaac tggtgtttatc tccctgaact tccagccaac ttctgttatg    840
catggtagct ttgactttga agtagttgct tctgacactt gtggtgcatc tgactgtgct    900
tctgtttcca tctacatgat ctccacccgt gttagagttc accaccaca ccaccactaa    960
```

<210> SEQ ID NO 29
<211> LENGTH: 319
<212> TYPE: PRT
<213> ORGANISM: Artificial sequence
<220> FEATURE:
<223> OTHER INFORMATION: BtB10 (protease stabilized)

<400> SEQUENCE: 29

Met Ala Phe Leu Asp Cys Leu Ser Ala Thr Asp Glu Asp Gly Leu His
1               5                   10                  15

Ala Gly Cys Val Thr Phe Ser Ile Ala Gly Asn Asp Glu Ala Ala Glu
            20                  25                  30

Tyr Phe Asn Val Leu Asn Asp Gly Asp Asn Ser Ala Met Leu Thr Leu
        35                  40                  45

Ser Gln Ala Leu Pro Ala Gly Val Gln Gln Phe Glu Leu Val Ile Ser
    50                  55                  60

Ala Thr Asp Gly Gly Thr Glu Pro Gly Pro Ser Ser Thr Asp Cys Ser
65                  70                  75                  80

Val Thr Val Val Phe Val Met Thr Gln Gly Asp Pro Val Phe Asp Asp
                85                  90                  95

Asn Ala Ala Ser Val Ser Phe Val Glu His Glu Ala Gly Met Ser Glu
            100                 105                 110

Ser Phe Gln Leu Pro Gln Ala Asp Asp Pro Ser Asn Tyr Ala Cys Met
        115                 120                 125

```
Asp Asp Cys His Thr Ile Tyr Tyr Ser Ile Val Asp Gly Asn Asp Gly
    130                 135                 140

Asp His Phe Ala Val Glu Pro Glu Thr Asn Val Ile Tyr Leu Leu Ser
145                 150                 155                 160

Pro Leu Asp Ser Ser Gln Gln Glu Gln Tyr Ser Val Val Ala Ala
                165                 170                 175

Ser Asn Thr Pro Gly Gly Thr Ser Thr Leu Ser Ser Leu Leu Thr
            180                 185                 190

Val Thr Ile Gly Val Ser Glu Ala Asn Pro Ser Pro Ile Phe Glu Ser
        195                 200                 205

Glu Phe Tyr Thr Ala Gly Val Leu His Thr Asp Ser Ile His Ser Glu
    210                 215                 220

Leu Val Tyr Leu Ala Ala Ser His Ser Glu Gly Leu Pro Ile Val Tyr
225                 230                 235                 240

Ser Ile Asp Gln Glu Thr Met Ser Ile Asp Glu Ser Leu Gln Thr Val
                245                 250                 255

Val Glu Asp Ala Phe Asp Ile Asn Ser Ala Thr Gly Val Ile Ser Leu
        260                 265                 270

Asn Phe Gln Pro Thr Ser Val Met His Gly Ser Phe Asp Phe Glu Val
    275                 280                 285

Val Ala Ser Asp Thr Cys Gly Ala Ser Asp Cys Ala Ser Val Ser Ile
    290                 295                 300

Tyr Met Ile Ser Thr Arg Val Arg Val His His His His His
305                 310                 315
```

<210> SEQ ID NO 30
<211> LENGTH: 960
<212> TYPE: DNA
<213> ORGANISM: Artificial sequence
<220> FEATURE:
<223> OTHER INFORMATION: BtB10 (protease stabilized)

<400> SEQUENCE: 30

```
atggcatttc tggattgtct gtctgcaact gatgaagatg gtctgcatgc tggttgtgtc      60
accttcagta ttgctggcaa tgatgaggca gcagaatatt ttaatgtact gaatgatggt     120
gacaactctg ctatgctgac cctgtcccag ctctgccag ctggtgttca gcagtttgag      180
ctggttatct ctgctactga tggtggtact gaaccaggcc catctagcac tgactgcagt     240
gttactgttg tatttgttat gacccagggt gacccagtat ttgatgacaa cgcagcttct     300
gtttcctttg ttgaacatga agctggtatg tctgagtcct tccagctgcc acaggctgat     360
gacccatcta actatgcttg tatggatgac tgccacacta tctactactc tattgtagat     420
ggtaacgatg gtgatcattt tgctgttgaa ccagaaacca acgtaattta tctgctgagc     480
ccactggact cttctcagca ggaacagtac tctgtagttg ttgcagcttc aacaccccca     540
ggtggtacat ccaccctgtc ttcttccctg ctgactgtta ctattggtgt atctgaagct     600
aacccatccc cgatctttga aagtgaattt tacactgctg gtgttctgca cactgactct     660
attcattctg aactggttta cctggcagct tctcactctg aaggtctccc aattgtatat     720
tctattgacc aggaaactat gtcaattgat gaatctctgc agactgtggt ggaagatgct     780
ttcgacatca actctgcaac tggtgttatc tccctgaact tccagccaac ttctgttatg     840
catggtagct ttgactttga agtagttgct tctgacactt gtggtgcatc tgactgtgct     900
tctgtttcca tctacatgat ctccacccgt gttagagttc accaccacca ccaccactaa     960
```

-continued

```
<210> SEQ ID NO 31
<211> LENGTH: 100
<212> TYPE: PRT
<213> ORGANISM: Lymantria dispar

<400> SEQUENCE: 31

Gly Ile Ser Thr Ser Asp Asn Ile Asn Arg Val Leu Leu Thr Val Gln
1               5                   10                  15

Ala Thr His Ser Glu Gly Ala Pro Val Thr Tyr Glu Ile Asp His Ser
            20                  25                  30

Thr Met Ile Val Asp Pro Thr Leu Glu Ala Val Lys Asp Thr Ala Phe
        35                  40                  45

Val Leu Asn Ser Gln Thr Gly Val Leu Thr Leu Asn Met Gln Pro Thr
    50                  55                  60

Ala Phe Met His Gly Asn Phe Glu Phe Lys Val Val Ala Thr Asp Pro
65                  70                  75                  80

Ser Glu Ala Thr Asp Arg Ala Ala Val Lys Ile Tyr Leu Ile Ser Ser
                85                  90                  95

Leu Asn Arg Val
            100

<210> SEQ ID NO 32
<211> LENGTH: 100
<212> TYPE: PRT
<213> ORGANISM: Pectinophora gossypiella

<400> SEQUENCE: 32

Gly Ile Ser Thr Ser Asp Asn Ile Asn Arg Glu Leu Leu Thr Val Arg
1               5                   10                  15

Ala Thr His Ser Glu Asn Ala Gln Leu Thr Tyr Thr Ile Glu Asp Gly
            20                  25                  30

Ser Met Val Val Asp Ser Thr Leu Glu Ala Val Lys Asp Ser Ala Phe
        35                  40                  45

His Leu Asn Ala Gln Thr Gly Val Leu Ile Leu Arg Ile Gln Pro Thr
    50                  55                  60

Ala Ser Met Gln Gly Met Phe Glu Phe Asn Val Ile Ala Thr Asp Pro
65                  70                  75                  80

Asp Glu Lys Thr Asp Thr Ala Glu Val Lys Val Tyr Leu Ile Ser Ser
                85                  90                  95

Gln Asn Arg Val
            100

<210> SEQ ID NO 33
<211> LENGTH: 100
<212> TYPE: PRT
<213> ORGANISM: Helicoverpa armigera

<400> SEQUENCE: 33

Gly Ile Ser Ala Gly Asp Phe Ile Glu Arg Asn Leu Leu Thr Val Val
1               5                   10                  15

Ala Thr His Ser Glu Gly Leu Pro Ile Thr Tyr Thr Leu Ile Gln Glu
            20                  25                  30

Ser Met Glu Ala Asp Pro Pro Leu Glu Ala Val Gln Glu Ser Ala Phe
        35                  40                  45

Ile Leu Asn Pro Glu Thr Gly Val Leu Ser Leu Asn Phe Gln Pro Thr
    50                  55                  60

Ala Ala Met His Gly Met Phe Glu Phe Glu Val Glu Ala Thr Asp Ser
65                  70                  75                  80
```

```
Arg Arg Glu Thr Ala Arg Thr Glu Val Lys Val Tyr Leu Ile Ser Asp
                85                  90                  95

Arg Asn Arg Val
            100

<210> SEQ ID NO 34
<211> LENGTH: 100
<212> TYPE: PRT
<213> ORGANISM: Heliothis virescens

<400> SEQUENCE: 34

Gly Ile Ser Thr Leu Asp Thr Ile Asn Arg Ala Leu Leu Thr Leu His
1               5                   10                  15

Ala Thr His Ser Glu Gly Leu Pro Val Thr Tyr Thr Leu Ile Gln Asp
            20                  25                  30

Ser Met Glu Ala Asp Ser Thr Leu Gln Ala Val Gln Glu Thr Ala Phe
        35                  40                  45

Asn Leu Asn Pro Gln Thr Gly Val Leu Thr Leu Asn Phe Gln Pro Thr
    50                  55                  60

Ala Ser Met His Gly Met Phe Glu Phe Asp Val Met Ala Ile Asp Thr
65                  70                  75                  80

Val Gly Glu Thr Ala Arg Thr Glu Val Lys Val Tyr Leu Ile Ser Asp
                85                  90                  95

Arg Asn Arg Val
            100

<210> SEQ ID NO 35
<211> LENGTH: 99
<212> TYPE: PRT
<213> ORGANISM: Chilo suppressalis

<400> SEQUENCE: 35

Gly Ile Ser Val Leu Asp Thr Ile Gln Arg Glu Leu Leu Thr Val Gln
1               5                   10                  15

Ala Thr His Ser Leu Gly Asp Asn Ile Ser Tyr Ala Ile Asp Ala Ala
            20                  25                  30

Ser Met Val Ala Asp Ser Ser Leu Ala Val Val Ala Glu Thr Ala Phe
        35                  40                  45

Leu Leu His Ala Arg Ser Gly Val Leu Ser Leu Asn Met Gln Thr Ala
    50                  55                  60

Asn Met His Gly Met Phe Glu Phe Asp Val Thr Ala Thr Asp Ser Ser
65                  70                  75                  80

Gly Gly Val Gly Arg Ala Gln Val Lys Val Tyr Leu Ile Ser Ser Gln
                85                  90                  95

Asn Arg Val

<210> SEQ ID NO 36
<211> LENGTH: 99
<212> TYPE: PRT
<213> ORGANISM: Ostrinia nubilalis

<400> SEQUENCE: 36

Val Ile Ser Thr Leu Asp Ser Ile Gly Arg Glu Leu Leu Thr Val Arg
1               5                   10                  15

Ala Ser His Thr Glu Asp Asp Ile Ile Thr Tyr Thr Ile Asp Arg Ala
            20                  25                  30

Ser Met Gln Leu Asp Ser Ser Leu Glu Ala Val Arg Asp Ser Ala Phe

```
                35                  40                  45
Ala Leu His Ala Arg Ser Gly Val Leu Ser Leu Asn Met Gln Thr Ala
 50                  55                  60
Asn Met His Gly Met Phe Glu Phe Asp Val Thr Ala Thr Asp Ser Ser
 65                  70                  75                  80
Gly Gly Val Gly Arg Ala Gln Val Lys Val Tyr Leu Ile Ser Ser Gln
                 85                  90                  95
Asn Arg Val
```

<210> SEQ ID NO 37
<211> LENGTH: 100
<212> TYPE: PRT
<213> ORGANISM: Plutella xylostella

<400> SEQUENCE: 37

```
Gly Ile Ser Thr Met Asp Ser Ile Asn Arg Glu Leu Phe Thr Val Lys
 1               5                  10                  15
Ala Thr His Thr Glu Asn Leu Ser Ile Lys Tyr Thr Ile Asp Pro Ser
                20                  25                  30
Ser Met Val Ala Asp Thr Ser Leu Gln Ser Val Gln Gly Ser Ala Phe
                35                  40                  45
Glu Leu Asp Ala Asp Ser Gly Val Leu Thr Leu Lys Ile Lys Pro Thr
 50                  55                  60
Ala Ser Met Arg Gly Met Phe Glu Phe Glu Val Val Ala Thr Asp Thr
 65                  70                  75                  80
Glu Gln Ala Thr Asp Arg Ala Glu Val Lys Val Tyr Ile Val Ser Asp
                85                  90                  95
Asn Asn Arg Val
           100
```

<210> SEQ ID NO 38
<211> LENGTH: 100
<212> TYPE: PRT
<213> ORGANISM: Manduca sexta

<400> SEQUENCE: 38

```
Gly Ile Ser Thr Ala Asp Ser Ile Gly Arg Glu Leu Leu Arg Leu His
 1               5                  10                  15
Ala Thr Gln Ser Glu Gly Ser Ala Ile Thr Tyr Ala Ile Asp Tyr Asp
                20                  25                  30
Thr Met Val Val Asp Pro Ser Leu Glu Ala Val Arg Gln Ser Ala Phe
                35                  40                  45
Val Leu Asn Ala Gln Thr Gly Val Leu Thr Leu Asn Ile Gln Pro Thr
 50                  55                  60
Ala Thr Met His Gly Leu Phe Lys Phe Glu Val Thr Ala Thr Asp Thr
 65                  70                  75                  80
Ala Gly Ala Gln Asp Arg Thr Asp Val Thr Val Tyr Val Val Ser Ser
                85                  90                  95
Gln Asn Arg Val
           100
```

<210> SEQ ID NO 39
<211> LENGTH: 100
<212> TYPE: PRT
<213> ORGANISM: Bombyx mori

<400> SEQUENCE: 39

```
Gly Ile Ser Thr Ser Asp Ser Ile Asn Arg Glu Leu Leu Ile Leu Gln
1               5                   10                  15

Ala Thr His Ser Glu Asn Ala Pro Ile Ile Tyr Thr Ile Asp Trp Ser
                20                  25                  30

Thr Met Val Thr Asp Pro Thr Leu Ala Ser Val Arg Glu Thr Ala Phe
            35                  40                  45

Ile Leu Asn Pro His Thr Gly Val Leu Thr Ile Asn Ile Gln Pro Thr
        50                  55                  60

Ala Ser Met His Gly Met Phe Glu Phe Gln Val Val Ala Thr Asp Pro
65                  70                  75                  80

Ala Gly Tyr Ser Asp Arg Ala Asn Val Lys Ile Tyr Leu Ile Ser Thr
                85                  90                  95

Arg Asn Arg Val
            100

<210> SEQ ID NO 40
<211> LENGTH: 100
<212> TYPE: PRT
<213> ORGANISM: Spodoptera frugiperda

<400> SEQUENCE: 40

Gly Val Leu His Thr Asp Ser Ile His Lys Glu Leu Val Tyr Leu Ala
1               5                   10                  15

Ala Lys His Ser Glu Gly Leu Pro Ile Val Tyr Ser Ile Asp Gln Glu
                20                  25                  30

Thr Met Lys Ile Asp Glu Ser Leu Gln Thr Val Val Glu Asp Ala Phe
            35                  40                  45

Asp Ile Asn Ser Ala Thr Gly Val Ile Ser Leu Asn Phe Gln Pro Thr
        50                  55                  60

Ser Val Met His Gly Ser Phe Asp Phe Glu Val Val Ala Ser Asp Thr
65                  70                  75                  80

Arg Gly Ala Ser Asp Arg Ala Lys Val Ser Ile Tyr Met Ile Ser Thr
                85                  90                  95

Arg Val Arg Val
            100
```

MODIFIED PEPTIDES HAVING TOXIN-ENHANCING EFFECTS

CROSS-REFERENCE TO RELATED APPLICATION

This application is a National Stage filing of PCT International Application Serial No. PCT/US2008/072812, filed 11 Aug. 2008, which claims the benefit of U.S. Provisional Application Ser. No. 60/964,249, filed Aug. 10, 2007, U.S. Provisional Application Ser. No. 60/956,618 filed Aug. 17, 2007, and U.S. Provisional Application Ser. No. 61/084,951, filed Jul. 30, 2008, the disclosures each of which are hereby incorporated by reference in their entirety, including all figures, tables and amino acid or nucleic acid sequences.

BACKGROUND OF THE INVENTION

The use of microbial insecticide in agriculture can be part of a larger integrated pest management program. *Bacillus thuringiensis* (Bt) based biopesticide has been proven after decades of use as a safe alternative to chemical insecticides. The insecticidal crystal proteins produced by *Bacillus thuringiensis* are broadly used to control insect pests with agricultural importance. Bt proteins can be used in agriculture via microbial pesticides and genetically modified crop plants.

Bt is a spore-forming, Gram-positive bacterium, that can be isolated from many environments (Chaufaux et al., 1997; Martin and Travers, 1989) and new Bt strains have been isolated from soil (Carozzi et al., 1991a; DeLucca et al., 1979; Martin and Travers, 1989; Smith and Couche, 1991), leaves (Kaelin et al., 1994; Smith and Couche, 1991), and insects (Carozzi et al., 1991b) worldwide. Bt produces one or more delta-endotoxins or Cry proteins, which form insoluble inclusions known as insecticidal crystal proteins (ICPs). Although a specific Bt toxin has a narrow spectrum of activity, many different types of Bt toxins have been characterized that have selective toxicity to different orders of insects (Schnepf et al., 1998). Bt is also the main source of genes for transgenic expression in crops to provide pest control with few or no chemical pesticide applications. However, the narrow spectrum of activity for specific Bt toxins also limits efficacy, resulting in additional chemical pesticide applications for adequate pest control.

A generally accepted mode of action for Cry toxins describes the sequential steps of protoxin activation, specific-binding, and cell toxicity (Schnepf et al., 1998). Ingested ICPs are solubilized and activated to a toxic form by the insect's digestive fluids. After crossing the peritrophic matrix, activated toxins bind to specific proteins (i.e. cadherin and aminopeptidase-N) on the midgut microvilli. A recent model (Bravo et al., 2004) proposes that monomeric toxin binds a cad glycosylphosphatidylinositolherin, facilitating further processing necessary for toxin oligomerization. Toxin oligomers have high-affinity to proteins that are attached to the cell membrane by a (GPI) anchor, such as aminopeptidase or alkaline phosphatase. This binding and the localization of GPI-anchored proteins in specific membrane regions called lipid rafts result in toxin oligomer insertion, formation of pores or ion channels, and cell death by osmotic shock. An alternative model proposes the activation of intracellular signaling pathways by toxin monomer binding to cadherin without the need of the toxin oligomerization step to cause cell death (Zhang et al., 2005). Midgut lesions caused by the toxins led to septicemia induced by midgut bacteria that eventually leads to insect death (Broderick et al., 2006).

The cadherin Bt-R1 is a receptor for Bt Cry1A toxins in midgut epithelia of tobacco hornworm (*Manduca sexta*). We previously identified the Bt-R1 region most proximal to the cell membrane (CR12-MPED) as the essential binding region required for Cry1Ab-mediated cytotoxicity. We also discovered that a peptide containing this region expressed in *Escherichia coli* functions as an enhancer of Cry1A toxicity against lepidopteran larvae (Chen et al., 2007).

US-2005-0283857-A1, U.S. Pat. No. 7,396,813, and WO 2005/07014A2 relate to the discovery and development of a Bt synergist that enhances Bt toxicity against insects that are agriculturally important pests. More specifically, these patent references relate to fragments of insect cadherins that can be used to enhance the toxicity of insecticidal crystal proteins produced by Bt some of which are commercial microbial biopesticides and some of which are expressed in transgenic plants. For ease of reference, we these peptides can be called "BtBoosters" or "BtB". BtBooster can be mixed with commercial formulations of Bt to increase the value of the formulations. BtBooster can also be co-expressed with Bt toxin in Bt transgenic plants to offer better pest protection.

United States Patent Applications 2005010188439 (McCutcheon) relates to using a lipase polypeptide having insecticidal activity together with a Bt insecticidal protein.

The use of microbial insecticide in agriculture can be part of a larger integrated pest management program. *Bacillus thuringiensis* (Bt) based biopesticide has been proven after decades of use as a safe alternative to chemical insecticides. The insecticidal crystal proteins produced by *Bacillus thuringiensis* are broadly used to control insect pests with agricultural importance. Bt proteins can be used in agriculture via microbial pesticides and genetically modified crop plants.

Bt is a spore-forming, Gram-positive bacterium, that can be isolated from many environments (Chaufaux et al., 1997; Martin and Travers, 1989) and new Bt strains have been isolated from soil (Carozzi et al., 1991a; DeLucca et al., 1979; Martin and Travers, 1989; Smith. and Couche, 1991), leaves (Kaelin et al., 1994; Smith and Couche, 1991), and insects (Carozzi et al., 1991b) worldwide. Bt produces one or more delta-endotoxins or Cry proteins, which form insoluble inclusions known as insecticidal crystal proteins (ICPs). Although a specific Bt toxin has a narrow spectrum of activity, many different types of Bt toxins have been characterized that have selective toxicity to different orders of insects (Schnepf et al., 1998). Bt is also the main source of genes for transgenic expression in crops to provide pest control with few or no chemical pesticide applications. However, the narrow spectrum of activity for specific Bt toxins also limits efficacy, resulting in additional chemical pesticide applications for adequate pest control.

A generally accepted mode of action for Cry toxins describes the sequential steps of protoxin activation, specific-binding, and cell toxicity (Schnepf et al., 1998). Ingested ICPs are solubilized and activated to a toxic form by the insect's digestive fluids. After crossing the peritrophic matrix, activated toxins bind to specific proteins (i.e. cadherin and aminopeptidase-N) on the midgut microvilli. A recent model (Bravo et al., 2004) proposes that monomeric toxin binds a cad glycosylphosphatidylinositolherin, facilitating further processing necessary for toxin oligomerization. Toxin oligomers have high-affinity to proteins that are attached to the cell membrane by a (GPI) anchor, such as aminopeptidase or alkaline phosphatase. This binding and the localization of GPI-anchored proteins in specific membrane regions called lipid rafts result in toxin oligomer insertion, formation of pores or ion channels, and cell death by osmotic shock. An alternative model proposes the activation of intracellular signaling pathways by toxin monomer binding to cadherin without the need of the toxin oligomerization step to cause cell death (Zhang et al., 2005). Midgut lesions caused by the toxins led to septicemia induced by midgut bacteria that eventually leads to insect death (Broderick et al., 2006).

The cadherin Bt-R1 is a receptor for Bt Cry1A toxins in midgut epithelia of tobacco hornworm (*Manduca sexta*). We previously identified the Bt-R1 region most proximal to the cell membrane (CR12-MPED) as the essential binding region required for Cry1Ab-mediated cytotoxicity. We also discovered that a peptide containing this region expressed in *Escherichia coli* functions as an enhancer of Cry1A toxicity against lepidopteran larvae (Chen et al., 2007).

US-2005-0283857-A1, U.S. Pat. No. 7,396,813, and WO 2005/07014A2 relate to the discovery and development of a Bt synergist that enhances Bt toxicity against insects that are agriculturally important pests. More specifically, these patent references relate to fragments of insect cadherins that can be used to enhance the toxicity of insecticidal crystal proteins produced by Bt some of which are commercial microbial biopesticides and some of which are expressed in transgenic plants. For ease of reference, these peptides can be called "BtBoosters" or "BtB". BtBooster can be mixed with commercial formulations of Bt to increase the value of the formulations. BtBooster can also be co-expressed with Bt toxin in Bt transgenic plants to offer better pest protection.

United States Patent Applications 20050101 88439 (McCutcheon) relates to using a lipase polypeptide having insecticidal activity together with a Bt insecticidal protein.

WO 03/018810 (by Syngenta) discusses some possibilities for adding Western corn rootworm (WCRW) cathepsin G favored sites (AAPF, AAPM, AVPF, PFLF) to B.t. Cry3A proteins.

BRIEF SUMMARY OF THE INVENTION

This invention relates in part to the modification of BtBoosters (BtB).

The subject invention relates in part to the discovery and demonstration that derivatives of BtBooster (BtB) have enhanced potentiating activity of various Bt products, including the commercial Bt sprayable products "Javelin®," "Dipel®," "Xentari®" and "Agree®" in plant-based bioassays and commercial Bt cotton "Bollgard I."

This invention also relates in part to the modification of BtBooster to increase its stability in insect midgut digestive juices. Some preferred embodiments of BtB have removed proteinase cleavage sites resulting in increased stability of the modified BtB in the insect gut, while retaining the ability to enhance B. t. proteins for improved insect control.

In some preferred embodiments, the protease-stable BtB is used in combination with B.t. spores and/or crystals comprising a Cry protein. In some of these embodiments, a preferred modified BtB is derived from cadherin repeat 12 (CR12) from BT-R$_{1a}$. Hua et al. (Hua et al., 2004a).

The subject invention also relates in part to the discovery that derivatives of BtB have enhanced potentiating activity of various Bt Cry proteins against important pest species including *Helicoverpa zea, Agrotis ipsilon, Spodoptera exigua* and *Spodoptera frugiperda*.

The subject invention also relates in part that derivatives of BtB have potentiating activity for Cry1Fa protein.

BRIEF DESCRIPTION OF THE FIGURES

FIG. 1 also illustrates the wild type cadherin from *Spopdoptera frugiperda* and the cadherin fragments Sf-CR10-12 (BtB9) and the protease-stabilized version Sf-CR10-12(PS) (BtB10).

FIG. 4 shows that the protease-stabilized Ms-CR12(PS) called BtB enhances to preparations of Bt spores and crystals. FIG. 4A shows that tomato leaves were dipped into a suspension of Bt strain NRD12 and Bt plus BtB1, BtB2 or BtB3. Leaves were fed to $2^{nd}$ instar *H. zea* larvae. Mortality was scored on day 2. BtB1 Ms-CR9-MPED; BtB2=Ms-CR12; BtB3=Ms-CR12 (PS). FIG. 4B shows that tomato leaves were dipped into a suspension of Bt (Javelin WG) and Bt plus BtB2 or BtB3. Leaves were fed to 2nd instar *H. zea* larvae. Mortality was scored on day 4. BtB2=Ms-CR12. BtB3=Ms-CR12 (PS).

FIG. 6A shows that a Bt-resistant strain of *P. xylostella*, based on a diet incorporation bioassay, was about 128-fold more susceptible to Agree WG than to Javelin WG. This was expected since the resistant insects were selected on Bt HD-1, which produces the same Cry toxins present in Javelin WG. Agree WG, however, contain Cry1C which has been shown to have very little cross resistance to Cry1A toxins and is highly active against *P. xylostella* (Tang et al., 1996). Both BtB2 and BtB3 inclusion bodies were able to significantly enhance Javelin WG® (Certis) (Jav) and Agree WG (Agr) against a Bt-resistant strain of *P. xylostella* (FIGS. 6B and 6C).

to increasing mass ratios of BtB to trypsin-activated Cry1Ac. Sample size: 32 larvae/replicate×3 replicates/treatment. The bioassay scored on day 7. BtB4 (CR10-12) and BtB5 were purified using Ni-column and dialysed in 10 mM Tris, 100 mM NaCl at pH 8.0. The results show that both BtB4 and BtB5 enhanced Cry1Ac toxicity to *H. zea* larvae at low Cry toxin to BtB ratios. Treatments included Cry1Ac toxin alone or Cry1Ac plus the indicated ratios of BtB4 or BtB5. Control was diluent only.

Figure 8:
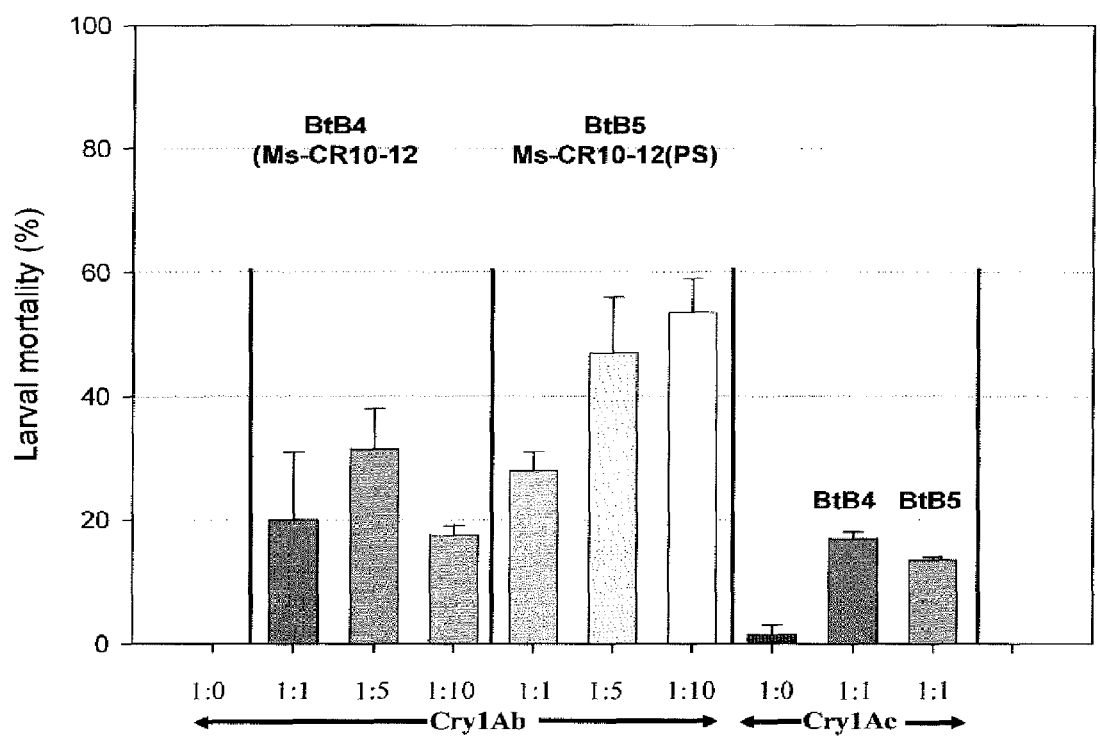

FIG. 8 shows the results of diet surface bioassays against neonate *S. exigua*. Sample size: 32 larvae/rep×2 rep/treatment. Bioassay was scored on day 7. Purified trypsin-activated Cry1Ab at 2 μg/cm², Cry1Ac at 4 μg/cm², and Ni-column purified BtBs at the indicated mass ratios were used in the bioassay. Diet surface treatment bioassay with neonate *S. exigua*. Sample size: 32 larvae/rep×2 rep/treatment. Bioassay was scored on day 7. Purified trypsin-activated Cry1Ab at 2 μg/cm2, Cry1Ac at 4 μg/cm2, and Ni-column purified BtBs at the indicated mass ratios were used in the bioassay.

Figure 9:
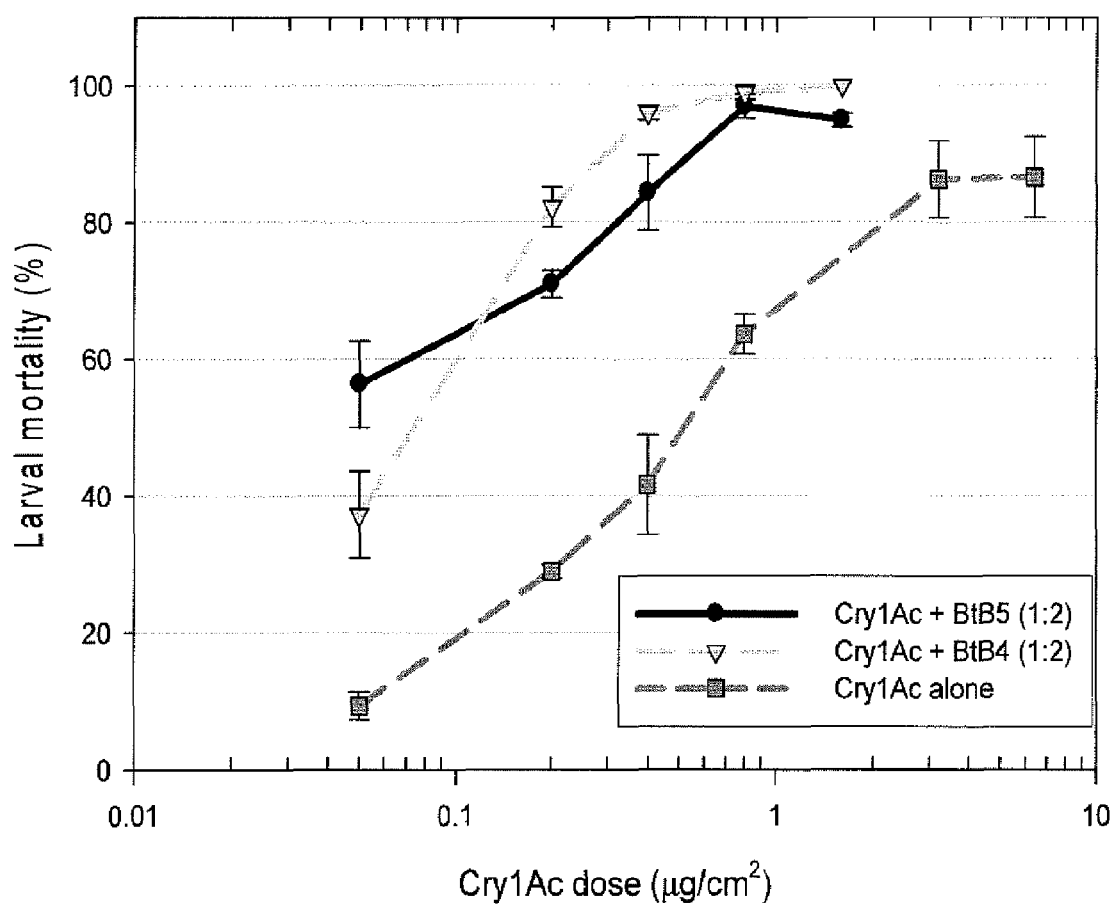

FIG. 9 shows that BtB4 (Ms-CR10-12) and BtB5 [Ms-CR10-12(PS)] at low Cry toxin to BtB mass ratios (1:2) lowered the $LC_{50}$ of Cry1Ac to *H. zea* (corn earworm, cotton bollworm). Diet surface treatment bioassay with neonate *H. zea* (corn earworm) to determine $LC_{50}$ with out and with BtB4 and BtB5. Sample size: 32 larvae/replicate×3 replicates/treatment. Bioassay scored on day 7. BtB4 (CR10-12) and BtB5 were purified using Ni-column and dialysed in 10 mM Tris, 100 mM NaCl at pH 8.0. $LC_{50}$ for: 1) Cry1Ac alone=0.54 (0.43-0.68) μg/cm² and 2) Cry1Ac+BtB4=0.07 (0.06-0.09) μg/cm² estimated (7.7-fold decrease) and 3) Cry1Ac+BtB5=0.04 (0.02-0.07) μg/cm2 estimated (13.5-fold decrease).

FIG. 10A illustrates the results of a cabbage excised-leaf bioassay with 4-day old *H. zea* showing enhancement of formulated Bt (Javelin WG® Certis) by BtB5 (Ms-CR10-12 (PS)] inclusion bodies. Sample size: 30 larvae×3 replicates/treatment. Bioassay was scored on Day 4. Bioassay was done with fixed 1:10 mass ratio of Javelin:BtB. FIG. 10B shows the results of a cabbage excised-leaf bioassay with 4-day old *H. zea* showing enhancement of formulated Bt (DiPel DF® Valent) by a spray-dried preparation of BtB5 [Ms-CR10-12 (PS)]. Sample size: 30 larvae/rep×4 rep/treatment. Bioassay was scored on day 4. Bioassay was done with fixed 1:6 mass ratio of DiPel:BtB. The amount of Ms-CR10-12(PS) in the spray-dried preparation was estimated at 22% of the dry weight by immunological detection (Western blot).

Figure 11A:
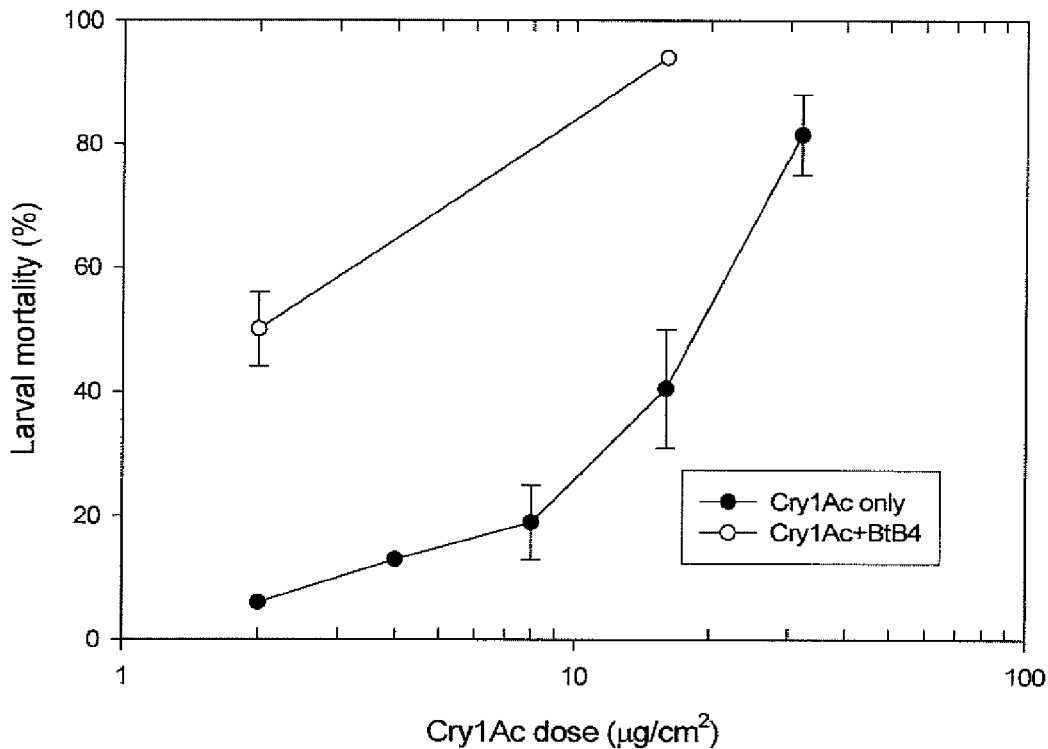
Figure 11B:
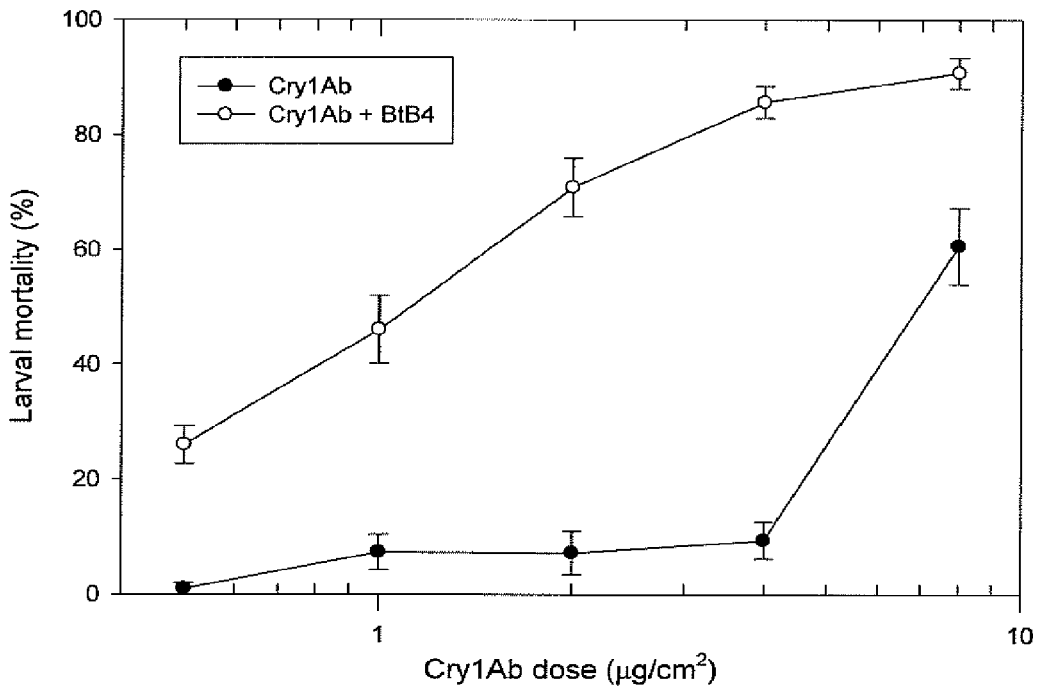

FIG. 11A shows that *M. sexta* cadherin CR10-12 (BtB4) fragment enhanced Cry1Ac in diet overlay bioassay with neonate *A. ipsilon*. Cry1Ac toxin was mixed with purified inclusion bodies of Ms-CR10-12 at a fixed toxin to synergist mass ratio of 1:10 and then overlaid on the diet surface. Control treatments with buffer and the synergist alone were not toxic to the larvae. Each data point represents data for the mean±standard errors from three replicate bioassays with 64 larvae per dose. $LC_{50}$s (μg/cm², 95% fiducial limits are provided in parentheses where applicable): (i) Cry1Ac alone=19.3 (17.9–20.9); (ii) Cry1Ac+CR10-12=~2.0 (~10-fold enhancement). FIG. 11B *M. sexta* cadherin Ms-CR10-12 fragment (BtB4) enhances Cry1Ab in diet overlay bioassay with neonate *S. exigua*. Cry1Ab toxin was mixed with purified inclusion bodies of Ms-CR10-12 at a fixed toxin to synergist mass ratio of 1:5 and then overlaid on the diet surface. Control treatments with buffer and the synergist alone were not toxic to the larvae. Each data point represents data for the mean±standard errors from three replicate bioassays with 64 larvae per dose. $LC_{50}$s (μg/cm², 95% fiducial limits are provided in parentheses where applicable): (i) Cry1Ab alone=~7.0; (ii) Cry1Ab+CR10-12=1.1 (0.9-1.3) (~6-fold enhancement).

FIG. 12 illustrates enhancement of Cry1C toxin by Ms-CR10-12 (BtB4) cadherin fragment in diet overlay bioassay with neonate *S. exigua*. A fixed amount of Cry1Ca toxin (0.6 μg/cm²) was mixed with purified inclusion bodies of CR10-12 at increasing toxin to synergist mass ratio of 1:1, 1:5, 1:10, 1:50, and 1:100, and then overlaid on the diet surface. Each column represents data for the mean±standard errors from four replicates with 64 larvae per treatment. Treatments: (A) Cry1Ca alone; (B) Cry1Ca+synergist (1:1 ratio); (C) Cry1Ca+synergist (1:5 ratio); (D) Cry1Ca+synergist (1:10 ratio); (E) Cry1Ca+synergist (1:50 ratio); (F) Cry1Ca+synergist (1:100 ratio).

Figure 13:
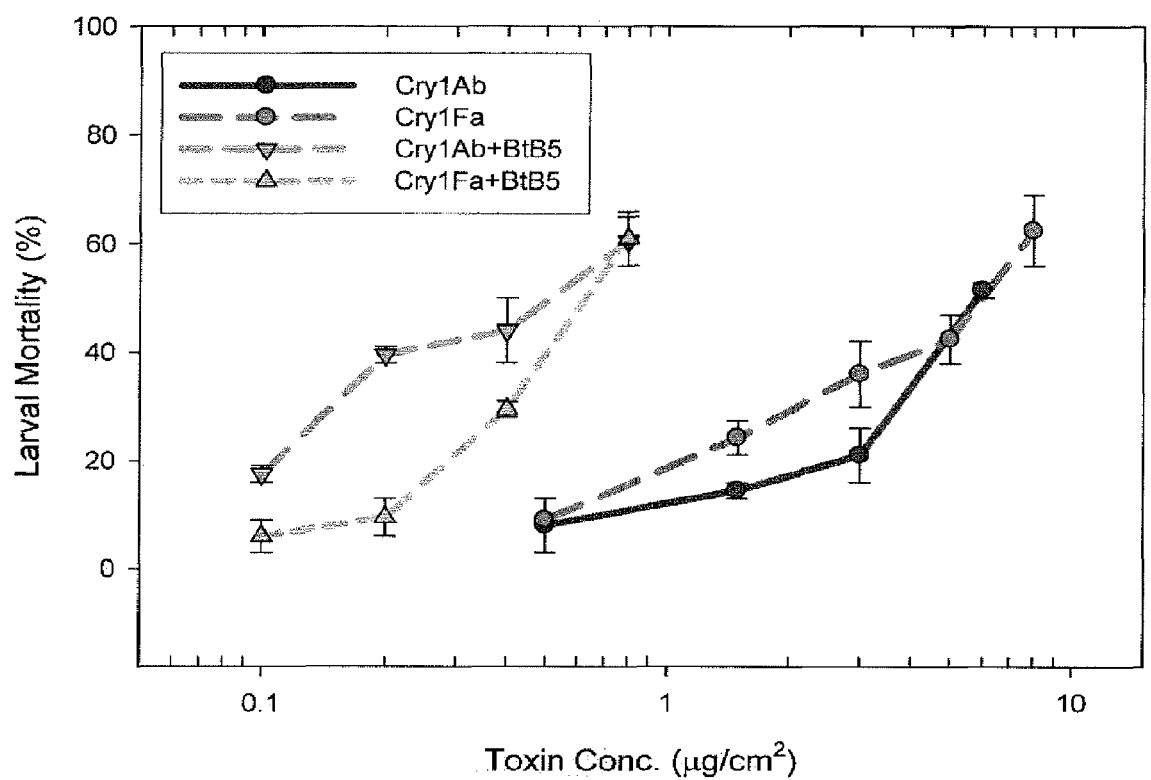

FIG. 13 shows the results of an *H. zea* diet surface bioassay. Cry1Ab or Cry1Fa toxins were applied alone or with BtB5. BtB5=Ms-CR10-12(PS). This Figure shows that BtB5 substantially shifted the Cry1Ab and Cry1Fa $LC_{50}$, for *H. zea* (corn earworm, cotton bollworm). Estimated $LC_{50}$s Cry1Ab $LC_{50}$=6.37 (5.03-9.58) μg/cm²; Cry1Ab+BtB5 $LC_{50}$=0.47 (0.31-0.89) μg/cm²; Cry1Fa $LC_{50}$=5.53 (4.26-8.74) μg/cm²; Cry1Fa+BtB5 $LC_{50}$=0.62 (0.52-0.79) μg/cm².

Figure 14:
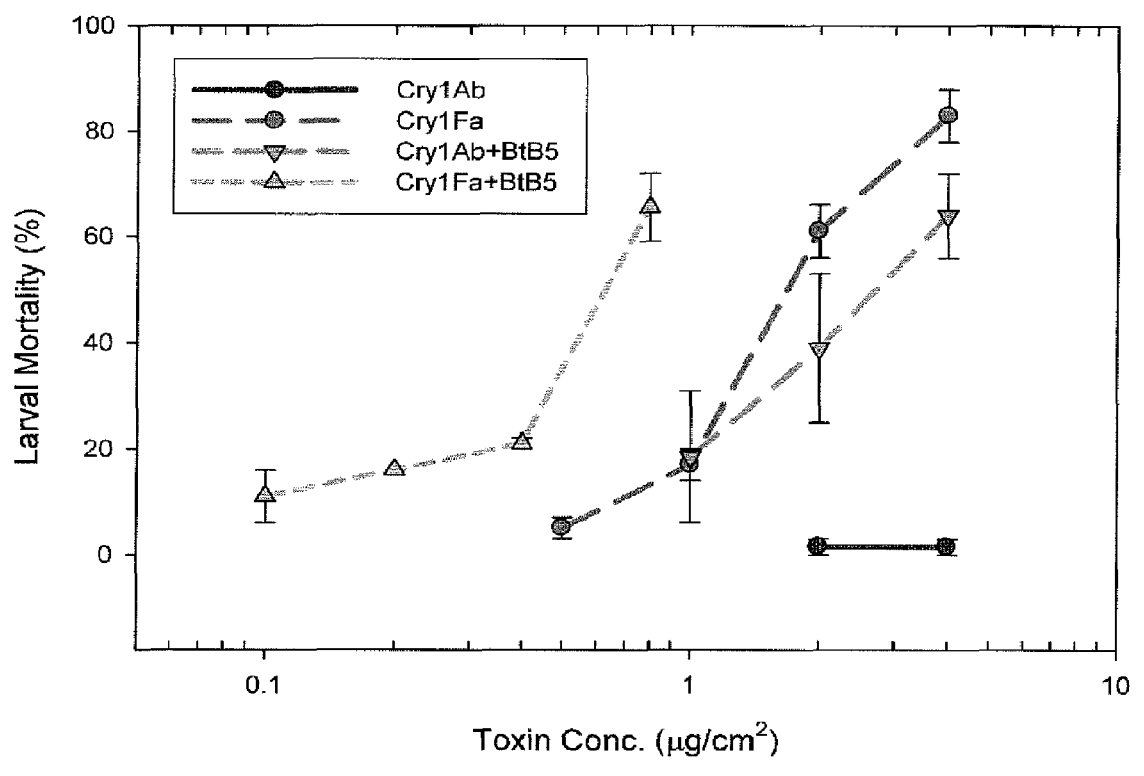

FIG. 14 shows the results of an *S. exigua* diet surface bioassay. Cry1Ab or Cry1Fa toxins were applied alone or with BtB5. BtB5=Ms-CR10-12(PS). This Figure shows that BtB5 substantially shifted the Cry1Ab and Cry1Fa $LC_{50}$s for *S. exigua*. Diet surface treatment bioassay with neonate *S. exigua*. Sample size: 32 larvae/rep×2 rep/treatment. Bioassay was scored on Day 5. The addition of BtB5 to Cry1Ab or Cry1Fa significantly shifted the dose response curve to the left. Cry1Ab $LC_{50}$=not determined. Cry1Ab+BtB5 $LC_{50}$=2.71 (2.30-3.35) μg/cm²; Cry1Fa $LC_{50}$=1.82 (1.63-2.04) μg/cm²; Cry1 Fa⁺ BtB5 $LC_{50}$=0.66 (0.60-0.72) μg/cm².

Figure 15:
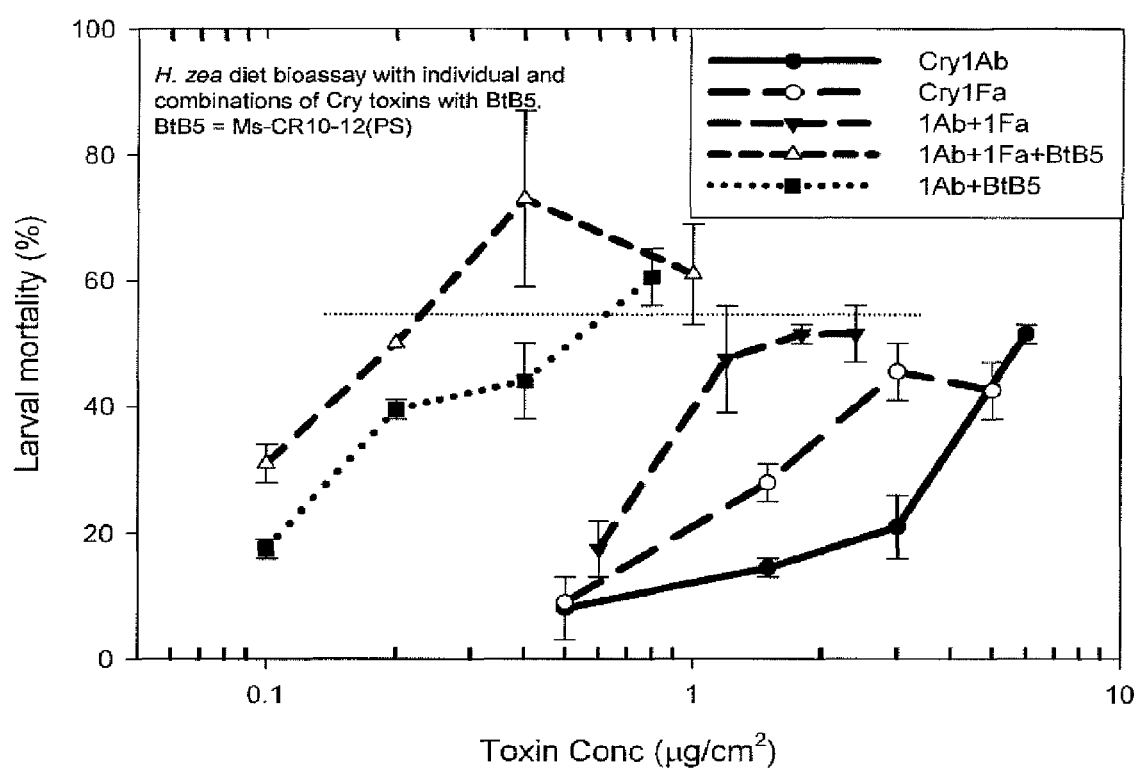

FIG. 15. BtB5 [Ms-CR10-12(PS)] enhanced a mixture of Cry1Ab and Cry1Fa against neonate corn earworms in a diet surface treatment bioassay with neonate *H. zea*. Sample size: 32 larvae/rep×2 rep/treatment. Bioassay was scored on Day 5. Addition of BtB5 to Cry1Ab or mixture of Cry1Ab and Cry1Fa shifted the dose response curve to the left. Cry1Ab estimated $LC_{50}$=5.30 (4.59-6.30) μg/cm²; Cry1Fa estimated $LC_{50}$=5.40 (3.65-11.58) μg/cm². Cry1Ab+BtB5 estimated $LC_{50}$=0.48 (0.35-0.78) μg/cm²; Cry1Fa+BtB5 was not tested. Mixture of Cry1Ab+Cry1Fa estimated $LC_{50}$=1.80 μg/cm². Cry1Ab Cry1Fa+BtB5 estimated $LC_{50}$=0.19 μg/cm².

FIG. 16. A combination of BtBs enhanced a mixture of Cry1Ac and Cry1Fa against neonate corn earworms. Diet surface treatment bioassay with neonate *H. zea*. Sample size: 32 larvae/rep×2 rep/treatment. Bioassay was scored on Day 7. *Addition of BtB5 and BtB9 to Cry1Ac+Cry1Fa enhanced toxicity significantly. Legend for treatments: (a). 0.025 μg/cm² Cry1Ac+0.125 μg/cm² Cry1Fa (1:5 ratio). (b). 0.05 μg/cm² Cry1Ac+0.25 μg/cm2 Cry1Fa (1:5 ratio). (c). 0.10 mg/cm2 Cry1Ac+0.50 μg/cm2 Cry1Fa (1:5 ratio). (d). 0.025 μg/cm² Cry1Ac+0.125 μg/cm² Cry1Fa+0.125 μg/cm² BtB5+ 0.125 μg/cm² BtB9. (e). 0M5 μg/cm² Cry1Ac+0.25 μg/cm²Cry1Fa+0.25 μg/cm²BtB5+0.125 μg/cm² BtB9. (f). 0.10 μg/cm²Cry1Ac+0.50 μg/cm² Cry1Fa+0.50 μm/cm² BtB5+0.125 μg/cm² BtB9.

Figures 17A, 17B:
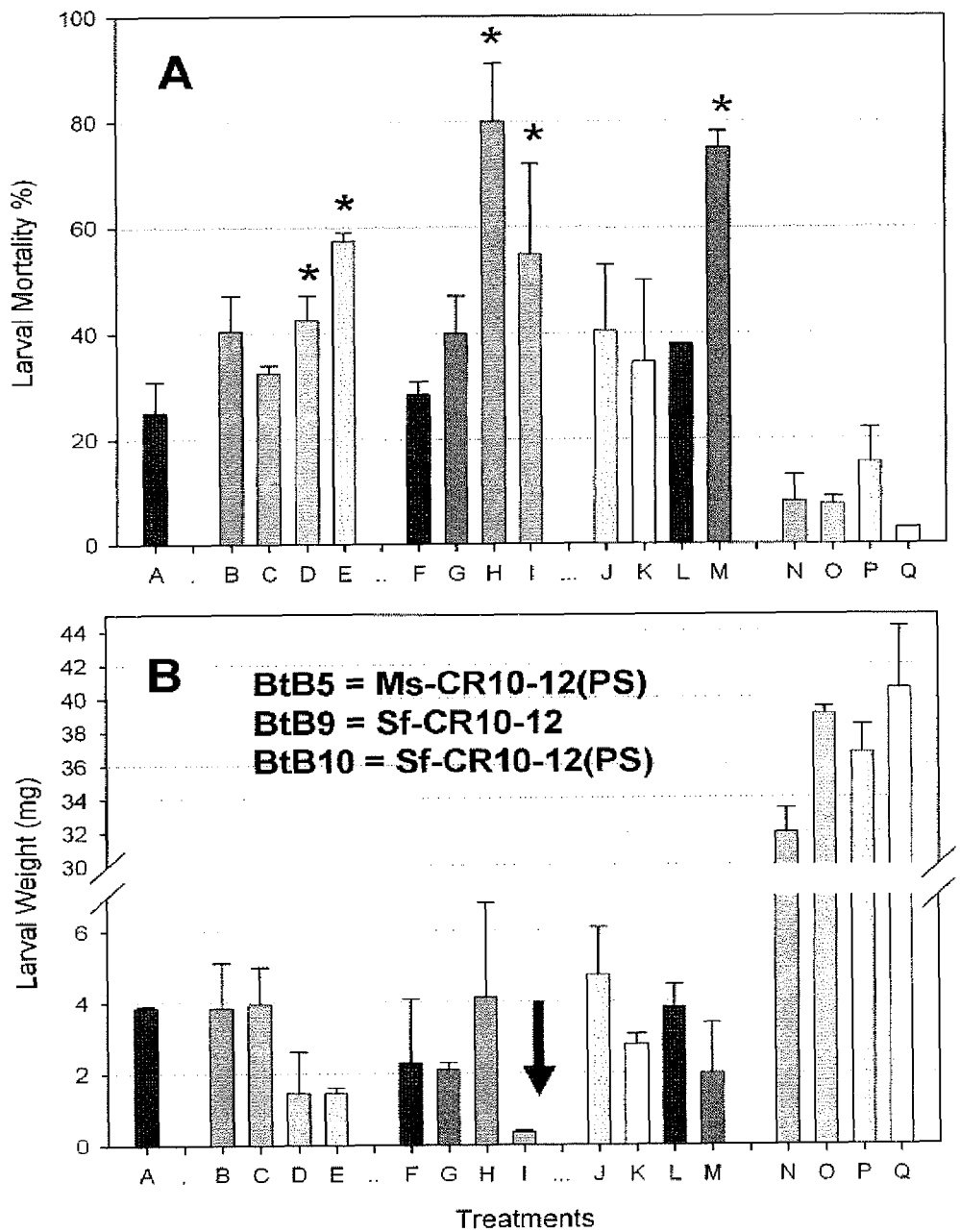

FIGS. 17A and 17B. In diet surface treatment bioassay with neonate *S. frugiperda* data provide evidence that protease-stabilization made BtB10 [S f-CR10-12(PS)] an improved enhancer relative to BtB9 (Sf10-12) or BtB5 [(Ms-CR10-12(PS)]. A 10-fold mass ratio of BtB10 was the best enhancer (~4-fold enhancement) compared to BtB9 (~2-fold enhancement) and BtB5 (<2-fold enhancement, not significant). Diet surface treatment bioassay with neonate *S. fru-*

Figure 18:
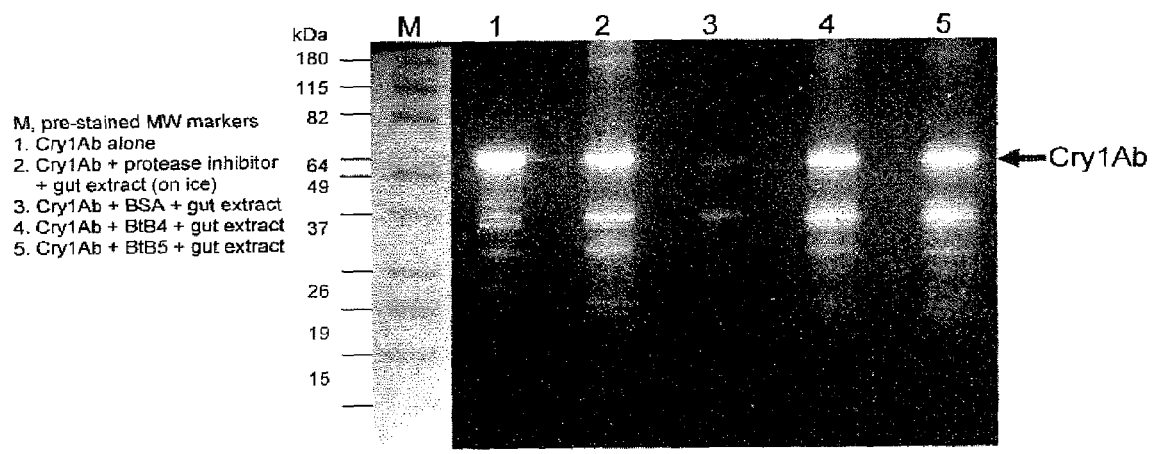

*giperda*. Sample size: 32 larvae/rep×2 rep/treatment. Bioassay was scored on Day 5. Total larval weight of survivors per replicate for each treatment was measured and then averaged. FIG. 17A shows the mortality data and FIG. 17B the larval weight data. *Significant enhancement compared to Cry1Fa (treatment A) (P<0.05). BtB10 (stabilized version of SfCR10-12) has better enhancement at 1:10 mass ratio compared to Sf10-12 or BtB5. The arrow in FIG. 17B designates the very significant growth inhibition enhancement by BtB10. Legend: A, 0.1 ug/cm² Cry1Fa. B, 0.1 µg/cm² Cry1Fa+0.1 µg/cm² BtB9 (1:1). C, 0.1 µg/cm² Cry1Fa+0.5 µg/cm²BtB9 (1:5). D, 0.1 µg/cm² Cry1Fa+1.0 µg/cm² BtB9 (1:10). E, 0.1 µg/cm²Cry1Fa+5.0 µg/cm² BtB9 (1:50). F, 0.1 µg/cm² Cry1Fa+0.1 µg/cm² BtB10 (1:1). G, 0.1 µg/cm² Cry1Fa+0.5 µg/cm² BtB10 (1:5). H, 0.1 µg/cm² Cry1Fa+1.0 µg/cm² BtB10 (1:10). I , 0.1 µg/cm² Cry1Fa+5.0 µg/cm² BtB10 (1:50). J, 0.1 µg/cm² Cry1Fa+0.1 µg/cm² BtB5 (1:1). K, 0.1 µg/cm² Cry1Fa+0.5 µg/cm² BtB5 (1:5). L, 0.1 µg/cm² Cry1Fa+1.0 µg/cm² BtB5 (1:1.0). M, 0.1 µg/cm² Cry1Fa+5.0 µg/cm²BtB5 (1:50). N, 5.0 µg/cm² BtB9. O, 5.0 µg/cm²BtB10. P, 5.0 µg/cm² BtB5. Q, dH₂O FIG. 18 shows increased stability of Cry1Ab in *S. exigua* beet armyworm gut extract in the presence of BtB4 or BtB5. Cry1Ab toxin (10 µg) was preincubated with equal mass of BSA, BtB4, or BtB5 for 30 min at 30° C. (pH 10) before incubation with *S. exigua* gut extract for 1 h at 30° C. (pH 10). Preincubation with either BtB4 or BtB5 protected the toxin from further proteolytic degradation by the gut extract (lanes 4 and 5) compared to preincubation with BSA (lane 3). Samples were treated with 5.5× protease inhibitor cocktail (Roche Complete) and then heated at 95° C. for 5 min to stop the reaction. Samples were mixed with SDS loading buffer and reheated again prior to loading onto SDS-PAGE, then transferred to a membrane. Cry1Ab was detected with anti-Cry1Ac antibody. The increased stability of toxin in the gut due to BtB presence could be a significant part of the mode of action for BtB.

FIG. 19A shows the mortality of Bt-resistant *P. xylostella* larvae feeding on leaves of *Arabidopsis* plant lines containing Cry1Ac protein and Cry1Ac plus BtB I or BIB3. Plants were transformed with a T-DNA vector containing a plant expression cassette directing the expression of a toxic Bt cry1Ac protein. Some *Arabidopsis* plants were co-transformed with a T-DNA vector with a plant expression cassette for BtB3 (Ms-CR9-MPED) and BtB3 [Ms-CR12(PS)]. The *P. xylostella* larvae were from a Bt-resistant colony (Benzon Research). Replicates consisted of 20+ cups containing a single *Arabidopsis* plant (foliage only) with five 4-day onl *P. xylostalla* larvae. Mortality was determined on day 4. FIG. 19B Cry1Ac levels in assayed *Arabidopsis* lines were determined from Western blot analysis and normalized to PEP carboxylase.

FIG. 20 shows a protein sequence alignment of the CR12 region from ten different lepidopteran species (*Ostrinia nubilalis* (European Corn Borer) (SEQ NO:36), *Chilo suppressalis* (Striped Rice Borer) (SEQ ID NO:35), *M. sexta* (Tomato Hornworm) (SEQ ID NO:38), *P. xylostella* (Diamondback Moth) (SEQ ID NO:37), *Pectinophora gossypiella* (Pink Bollworm) (SEQ ID NO:32), *Lymantria dispar* (Gypsy Moth) (SEQ ID NO: 31), *Bombyx mori* (Silkworm) (SEQ ID NO:39), *Helicoverpa armigera* (Cotton Bollworm) (SEQ ID NO:33), *Heliothis virescens* (Tobacco Budworm) (SEQ ID NO:34) and *S. frugiperda* (Fall Armyworm) (SEC) ID NO:40).

SEQ ID NO: 1 is the polynucleotide sequence of Ms-CR9-MPED also called BtB1.

SEQ ID NO:2 is the amino acid sequence of Ms-CR9-MPED (BtB1).

SEQ ID NO:3 is the nucleotide sequence of Ms-CR9-MPED (BtB1).

SEQ ID NO:4 is the polynucleotide sequence that encodes the amino acid sequence of Ms-CR12 also called BtB2—a 12 kDa peptide representing CR12. An N-terminal methionine and C-terminal 6× histidine residues were added for protein expression and purification.

SEQ ID NO:5 is the amino acid sequence of Ms-CR12 (BtB2).

SEQ ID NO:6 is the nucleotide sequence of Ms-CR12 (BtB2).

SEQ ID NO:7 is the polynucleotide sequence of Ms-CR12 (PS) also called BtB3—a modified Ms-CR12 with increased protease stability.

SEQ ID NO:8 is the amino acid of Ms-CR12(PS), also called BtB3—a 12 kDa peptide of modified Ms-CR12 with increased protease stability.

SEQ ID NO:9 is the nucleotide sequence of Ms-CR12(PS), also called BtB3.

SEQ ID NO:10 is the polynucleotide that encodes the amino acid sequence ofMs-CR10-12, also called BtB4. Six histidines were added to the C-terminus of the peptide for ease of protein purification.

SEQ ID NO:11 is the amino acid sequence of Ms-CR10-12, also called BtB4.

SEQ ID NO:12 is the nucleotide sequence of Ms-CR10-12, also called BtB4.

SEQ ID NO:13 is the polynucleotide sequence of Ms-CR10-12(PS), also called BtB5—a protease-stabilized version of Ms-CR10-12

SEQ ID NO:14 is the amino acid sequence of Ms-CR10-12(PS), also called BtB5—the protease stabilized version of CR10-12

SEQ ID NO:15 is the nucleotide sequence of Ms-CR10-12(PS), also called BtB5

SEQ ID NO:16 is the polynucleotide sequence of Ms-CR7-12

SEQ ID NO:17 is amino acid sequence of Ms-CR7-12

SEQ ID NO:18 is nucleotide sequence of Ms-CR7-12

SEQ ID NO:19 is the polynucleotide sequence of Ms-CR9-12

SEQ ID NO:20 is amino acid sequence of Ms-CR9-12

SEQ ID NO:21 is nucleotide sequence of Ms-CR9-12

SEQ ID NO:22 is the polynucleotide sequence of Ms-CR11-12

SEQ ID NO:23 is amino acid sequence of Ms-CR11-12

SEQ ID NO:24 is nucleotide sequence of Ms-CR11-12

SEQ ID NO:25 is the polynucleotide sequence that encodes the amino acid sequence of Sf-CR10-12, also called BtB9. Sf-CR10-12 was designed from cadherin repeats 10-12 of *S. frugiperda* cadherin. Codons were optimized for *E. coli* expression. Several CG dinucleotides were changed for plant expression. An N-terminal methionine and a lysine residue was added at amino acid position 2.

SEQ ID NO:26 is the amino acid sequence of Sf-CR10-12, also called BtB9

SEQ ID NO:27 is nucleotide sequence of Sf-CR10-12, also called BtB9

SEQ ID NO:28 is the polynucleotide sequence of Sf-CR10-12(PS), also called BtB10. A protease-stabilized version of Sf-CR10-12.

SEQ ID NO:29 is the amino acid sequence of Sf-CR10-12 (PS), also called BtB10

SEQ ID NO:30 is nucleotide sequence of Sf-CR10-12(PS), also called BtB10

DETAILED DESCRIPTION OF THE INVENTION

The subject invention relates in part to versions of BtBooster™ (BtB) that have even better enhancement properties than the originals tested. For example, BtB versions enhanced the Certis USA product Javelin® WG (contains the Bt NRD12 strain) in tomato excised-leaf bioassays against *Helicoverpa zea*. Additional excised-leaf bioassays using soybean and cabbage consistently demonstrated that BtBooster™ significantly enhanced Javelin® WG. Bioassays with Javelin® WG plus BtBooster™ against resistant *P. xylostella* larvae consistently showed that the addition of BtBooster™ to the biopesticide significantly enhanced mortality in both excised-leaf and whole plant greenhouse experiments.

The BtB version described in (Chen et al., 2007) is comprised of the CR12-MPED region of *M. sexta* cadherin BtR1a. Our analysis of diet surface bioassays against *H. zea* showed that Ms-CR10-12 (BtB4) was significantly better in enhancing trypsin-activated Cry1Ac. We discovered that although BtB4 enhanced Cry toxins, the BIB4 was rapidly degraded by midgut proteases and that a protease-stabilized version, called BtB5 had improved enhancement of BE spores and crystals.

The original BtB is a truncated cadherin peptide derived from Bt-$R_{1a}$. Three modified versions of BtB were initially generated: i) Ms-CR9-MPED, also called BtB1—a 60 kDa peptide representing cadherin repeat (CR) 9 to the membrane proximal domain, ii) Ms-CR12, also called BtB2—a 12 kDa peptide representing CR12, and iii) Ms-CR12, also called BtB3—a 12 kDa peptide of modified CR12 with increased protease stability. Additional versions of BtB, Ms-CR10-12 (also called BtB4) and the Ms-CR10-12(PS), also called BtB5 (FIG. 1) were also developed and tested successfully.

Figure 2:
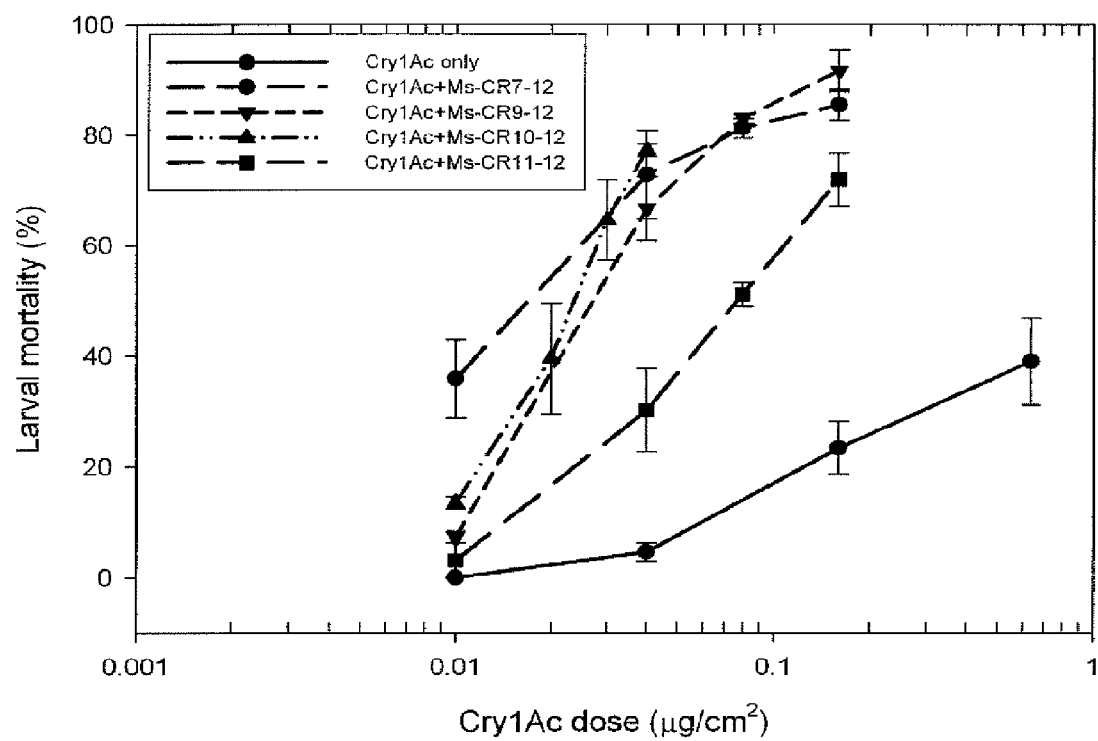
FIG. 2 shows that longer cadherin fragments (Ms-CR7-12, Ms-Cr9-12, and MsCR10-12) enhanced Cry1Ac to a greater extent than did Ms-CR11-12. More specifically, this Figure shows *M. sexta* cadherin fragments enhanced Cry1Ac in diet overlay bioassay with neonate *H. zea*. Cry1Ac toxin was mixed with purified inclusion bodies of Ms-CR7-12, Ms-CR9-12, Ms-CR10-12, or Ms-CR11-12 at a fixed toxin to synergist mass ratio of 1:20 and then overlaid on the diet surface.
Figure 3:
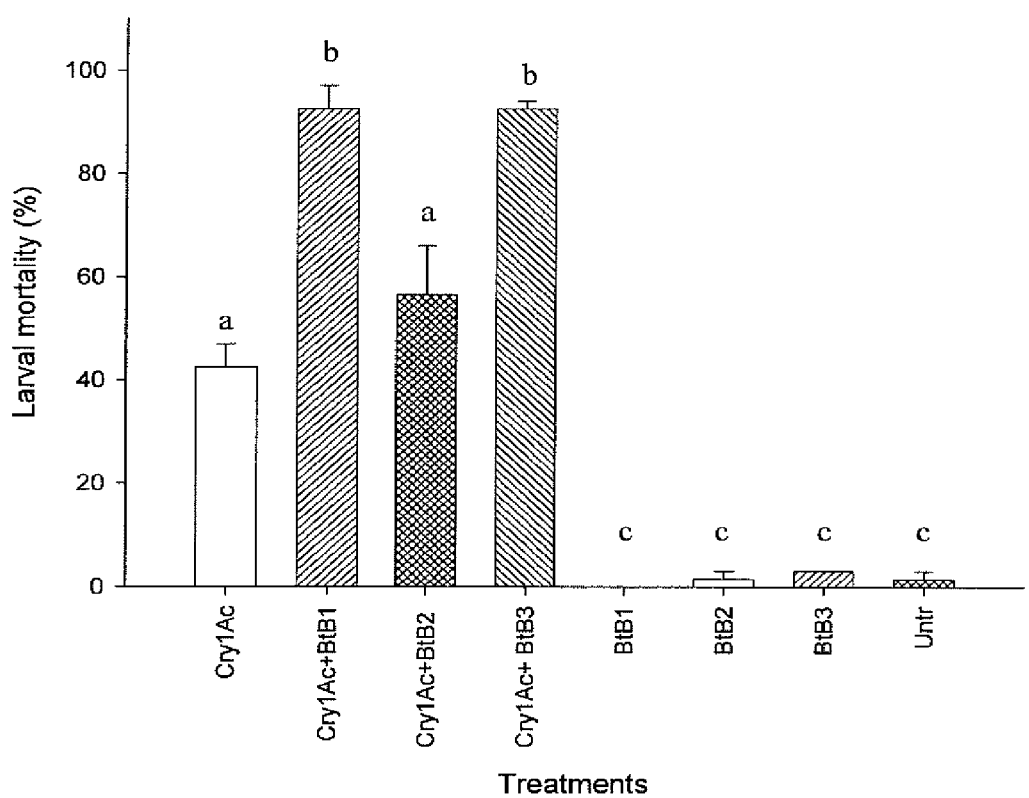
FIG. 3 demonstrates the increased Cry1Ac toxin enhancing properties of Ms-CR9-MPED and the protease-stabilized Ms-CR12(PS) relative to the Ms-CR12 cadherin fragment. This was a diet surface treatment bioassay with *H. zea* larvae. More specifically, this Figure shows diet surface contamination using purified Cry1Ac with or without soluble peptides on FL zea neonates. Mass ratio of toxin to BtB was 1:20. Mortality was scored on day 7. BtB1=Ms-CR9-MPED. BtB2=Ms-CR12. BtB3 Ms-CR12(PS).
Figure 4A:
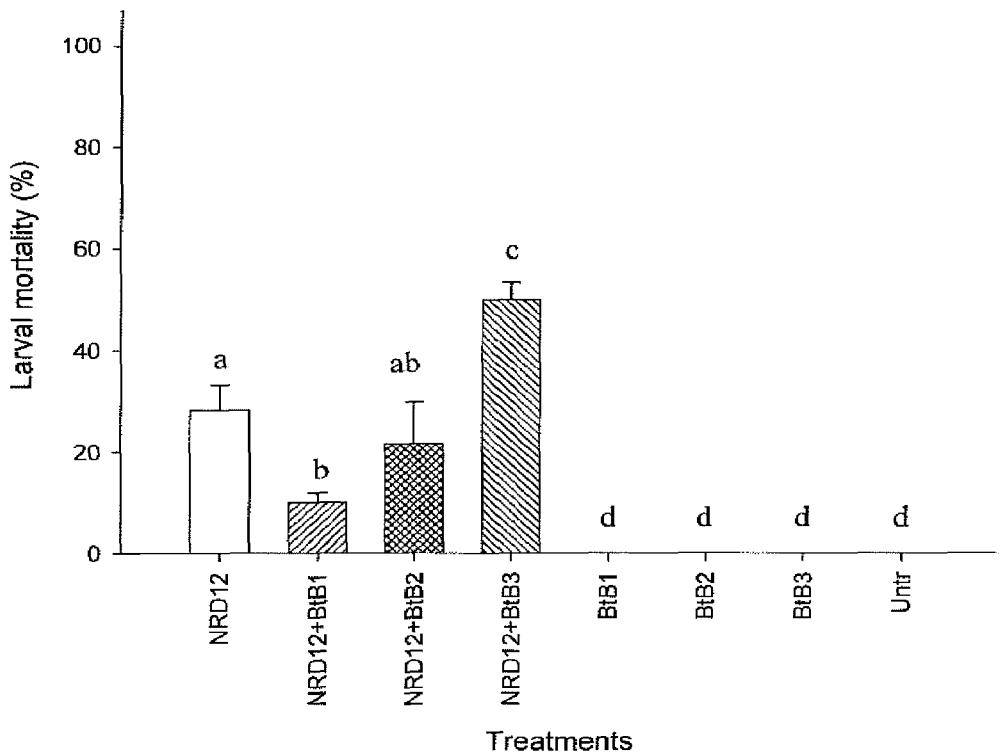
In FIG. 4A tomato leaves were dipped into suspensions of Bt NRD12 in diluent or Bt NRD12 with BtB1, BtB2 or BtB3.
Figure 4B:
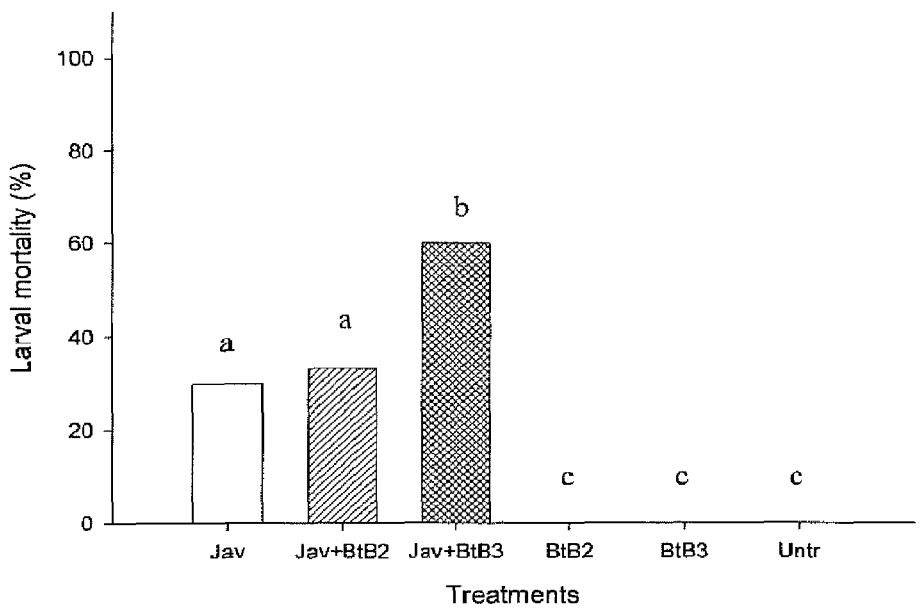
In FIG. 4B tomato leaves were dipped into a formulation of a commercial Bt called Javelin WG® (Certis) without or with BtB1, BtB2 or BtB3. The protease-stabilized Ms-CR12 cadherin fragment called Ms-CR12(PS) or BtB3 enhanced the toxicity of the Bt to *H. zea* larvae.

Our analysis of diet-surface bioassays with Ms-CR9-MPED also called BtB1 (consisted of cadherin repeats (CR) 9-MPED; 28-fold enhancement of Cry1Ac) was significantly better than the original BtBooster (CR12-MPED). Other *Manduca* cadherin peptides, including Ms-CR7-12, MsCR9-12 and MsCR10-12 had greater enhancement of Cry1Ac toxicity to *H. zea* than Ms-CR11-12 (FIG. 2) and Ms-CR12 (BtB2). A protease-stabilized Ms-CR12, called Ms-CR12 (PS) or BtB3, had improved enhancement with trypsin-activated Bt Cry1Ac toxin against *H. zea* (FIG. 3). Initial work showed the non-protease stabilized BIB versions such as BtB1 (Ms-CR9-MPED) and BtB2 (Ms-CR12) apparently did not enhance Bt spores and crystals (FIGS. 4A and 4B). Initial work demonstrated that some BtB molecules were unstable under certain conditions, thus reducing their levels of potentiation in those conditions.

Figure 5:
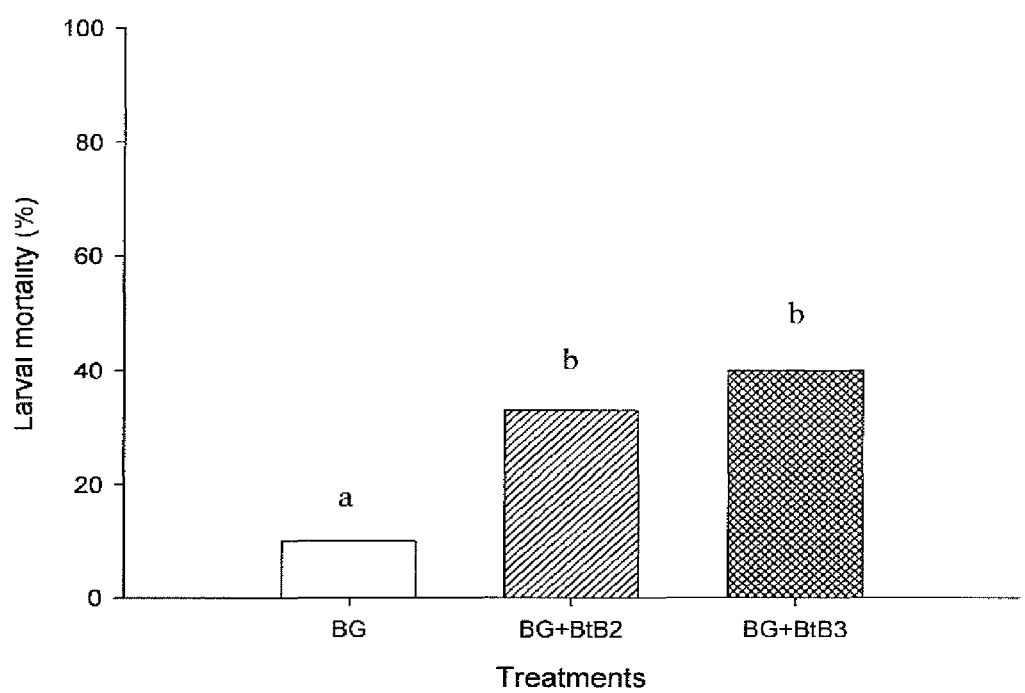
FIG. 5 illustrates the results of leaves from 4-5 weeks old B. t. cotton that were dipped in BtB inclusion bodies, air dried, and then fed to $2^{nd}$ instar *H. zea* larvae. This bioassay was scored on the fourth day. As shown, mortality was significantly increased when the leaves were treated with either BtB2 (Ms-CR12) or BtB3 Ms-CR12(PS)]. *Helicoverpa zea* larvae were allowed to feed on Bollgard I (BG) leaves or leaves dipped into BtB inclusion body suspensions. Mortality was scored after 4 days. BtB2=Ms-CR12. BtB3=Ms-CR12 (PS).
Figure 7:
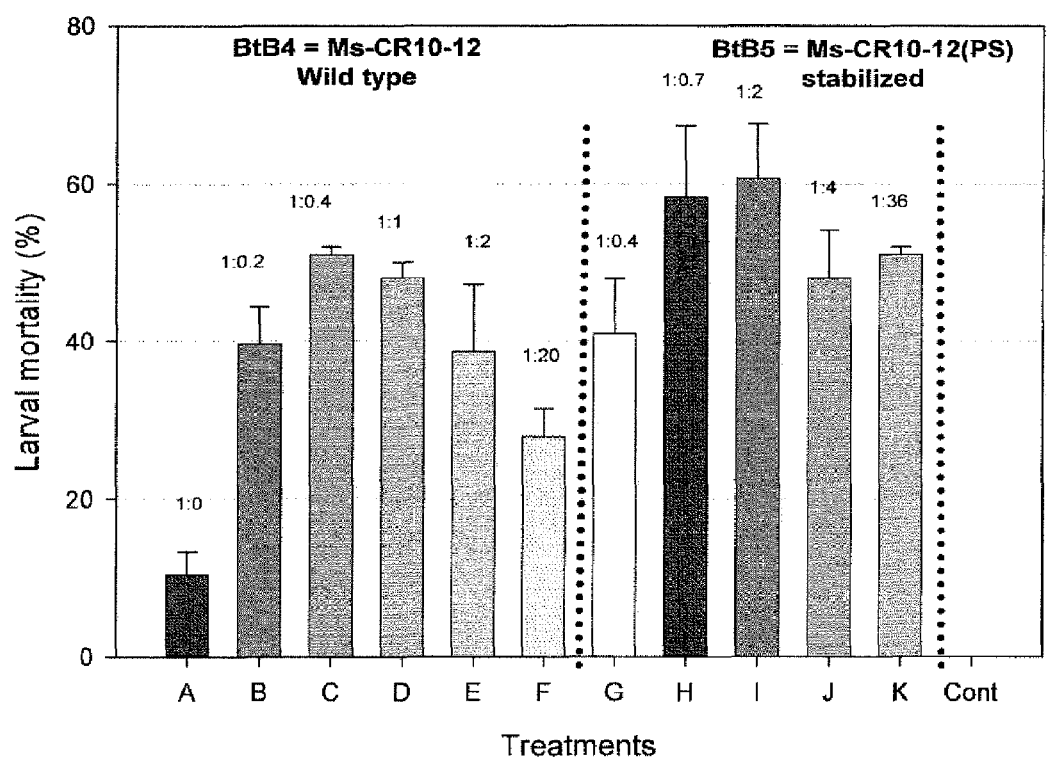
FIG. 7 shows that BtB4 (Ms-CR10-12) and BtB5 [Ms-CR10-12(PS)] enhanced Cry1Ac against *H. zea* (corn earworms) at low Bt:BtB Mass Ratios. Diet surface treatment bioassays were used to expose neonate *H. zea* (corn earworm)

BtB3 called Ms-CR12(PS), for the protease-stabilized version of pMs-CR12, was designed to have a reduced number of insect gut protease sensitive sites (specifically trypsin) without unduly increasing stability to human digestive enzymes. This version was tested in tomato excised-leaf bioassays with both a preparation of Bt NRD12 spores and crystals and a formulation of Javelin® (Certis). We found that BtB3 was able to enhance Bt spores and crystals toxicity (FIGS. 4A and 4B). We also found that BtB2 and BtB3 were able to increased mortality of *H. zea* feeding on Bt cotton (Bollgard I) (FIG. 5). BtB2 and BtB also enhanced Javelin® and Agree® in diet-incorporation bioassays against Bt-resistant *Plutella xylostalla* larvae (FIGS. 6A and 6B). Since we observed that Ms-CR10-12 had greater Cry toxin enhancing properties than Ms-CRL 2 and MsCR11-12, we designed a protease-stabilized version of Ms-CR10-12 called MsCR10-12(PS) or BtB5. Also, we demonstrated that BtB5 was able to enhance Javelin® against *H. zea* in cabbage leaf bioassays which. BtB4 did not do (FIGS. 10A and 10B). BtB4 and BtB5 also enhanced other toxins including Cry1Ab and Cry1Fa (these are important toxins because they are in Bt corn) (FIGS. 8, 13, 14, 15, 16). Also, BtB5 enhanced Cry1Fa toxicity to *S. frugiperda* (Fall armyworm) larvae (FIGS. 17A an 17B). This is a significant development since Fall armyworm is hard to control with Bt, and control of this important pest would improve its Bt's utility as an alternative to chemical control.

Since Fall armyworm is an important lepidopteran pest that is killed by only a few Bt toxins, we reasoned that a BtBooster designed from it's midgut cadherin may have useful and improved toxin-enhancing properties. We designed and expressed Sf-CR10-12 (BtB9) and a protease-stabilized version Sf-CR10-12(PS). Both Sf cadherin peptides enhanced Cry toxicity to Fall armyworm (FIGS. 17A and 17B).

In summary, our results further demonstrate the advantage of applying BtB plus Bt for controlling important agricultural insect pests (i.e. *H. zea, S. exigua, S. frugiperda* and Bt-resistant *P. xylostella*).

We also developed a modified BtB (BtB5) that works better than a previous version (BtB3) with a Bt spores and crystals formulation and extends insect control to *Spodoptera* species and Bt-resistant insects. Performance of BtB5 is being tested in field trials. We also developed other BtBs (BtB9 and BtB10) from *S. frugiperda* cadherin that have increased enhancing properties for certain Cry1 toxins.

Background on Receptor Bt-$R_1$.

The cadherin protein Bt-$R_1$ from *Manduca sexta* binds Cry1Aa, Cry1Ab and Cry1Ac toxins on ligand blots (Francis and Bulla, 1997). Purified membranes from COS cells expressing Bt-$R_1$ bound all three Cry1A toxins in binding assays and ligand blots (Keeton and Bulla, 1997). Furthermore, expression of Bt-$R_1$ on the surface of COS7 cells led to toxin-induced cell toxicity as monitored by immunofluorescence microscopy with fixed cells (Dorsch et al., 2002). The Bt-$R_1$ protein has been suggested to induce a conformational change in Cry1Ab that allows the formation of a pre-pore toxin oligomer (Gomez et al., 2002). In *Bombyx mori*, the cadherin-like protein BtR175 serves as a Cry1Aa receptor (Nagamatsu et al., 1998). Sf9 cells expressing BtR175 swell after exposure to Cry1Aa toxin, presumably due to formation of ion channels in cell membranes (Nagamatsu et al., 1999).

Another cadherin protein was cloned from *M. sexta* called Bt-$R_{1a}$ (Hua et al., 2004b). Bt-$R_{1a}$ cDNA differs from Bt-$R_1$ by 37 nucleotides that altered two amino acids.

In some examples, BtB is a truncated cadherin peptide derived from Bt-$R_{1a}$. Three versions of BtB were generated, as discussed above. "BtB1" as referred to herein is a 60 kDa peptide representing cadherin repeat (CR) 9 to the membrane proximal domain. The sequence of BtB1 is provided as SEQ ID NO:1.

Use in Spores and Crystals Formulations.

As discussed in more detail below, it is interesting to note that although BtB1 can enhance purified activated Cry1Ac toxin, it was unable to enhance Bt (NRD12) spores and crystals preparation containing Cry1Aa, Cry1Ab, Cry1Ac, Cry2A and Cry2B crystal proteins when applied to plant surfaces. Since the crystals need to be dissolved and activated in the midgut of target insects, the BtB peptides need to be stabilized from protease degradation so that sufficient BtB remains to react with the activated toxins. Site-directed mutagenesis was done sequentially to remove trypsin and chymotrypsin recognition sequence from BtB2 to create BtB3. BtB2 (SEQ ID NO:4) is a 12 kDa peptide representing CR12, and BtB3 (SEQ ID NO:7) is a 12 kDa peptide of modified CR12 with increased protease stability. Embodiments of modified BtBs according to the subject invention can have at least one trypsin and/or chymotrypsin recognition site removed (by removal or by modification to change the site so that it is no longer recognized by one or more proteases. BtB5 (SEQ ID NO:13) and BtB10 (SEQ ID NO:27) are additional examples of modified BtBs having at least one trypsin and/or chymotrypsin recognition site removed.

Overview of some Experimental Procedures.

BtB was cloned by PCR and inserted into an *Escherichia coli* expression vector and highly expressed in the cells as inclusion bodies. The inclusion bodies were highly soluble in alkaline buffer (pH 9-12). Both inclusion bodies (FIG. 2) and solubilized BtB (FIG. 3) were successful in enhancing purified Cry1Ac when tested in diet-based bioassays with neonates of *H. zea*. This is an advantage since BtB did not require further physical or chemical treatment for it to perform as a synergist.

BtB was expressed in *E. coli* as insoluble inclusion bodies. However, the inclusion bodies were highly soluble in alkaline buffers. This suggests that the inclusion bodies would be soluble in the alkaline environment of the lepidopteran larval midgut. Since the BtB was expressed at very high level in *E. coli*, the subject invention provides for cost-effective production of BtB for addition to B.t. as an adjuvant or as part of the formulation.

BtB Enhanced Purified Bt Toxin.

In some tests showing the enhancing activity of BtB, purified Cry1Ac toxin that was preactivated with trypsin, and was mixed with BtB inclusion bodies. Toxin to BtB1 mass ratio of 1:20 was maintained through serial dilution with distilled water and applied on the diet surface and allowed to air-dry. Bioassays with *H. zea* neonates were scored on the seventh day, and the percentage of larval mortality was determined (FIG. 2). The $LC_{50}$ of the toxin-only treatment and the toxin-BtB1 mixture treatment were calculated by the probit method (SoftTOX ver. 1.1). BtB1 enhanced Cry1Ac by about 28-fold.

In another bioassay, various length BtB peptides were tested for their ability to enhance purified Cry1Ac toxin. BtB inclusion bodies were mixed with purified Cry1Ac toxin and was then applied on the diet surface. Toxin to BtB was maintained at a mass ratio of 1:20. In this bioassay (FIG. 2), Cadherin fragments longer than Ms-CR11-12 enhanced Cry1Ac better than MsCR11-12. This suggests that longer-length cadherin fragments might enhance the synergistic effect. The BtB proteins did not show any toxic effect on the larvae when applied alone.

BtB Enhanced B.t. Spores and Crystals.

Most Bt-based biopesticides contain spores and crystals of the bacteria as the active ingredient. B.t. subsp. *kurstaki* (NRD12) is the active ingredient of Javelin WG (Certis). The formulation contains several different Cry toxins: Cry1Aa, Cry1Ab, Cry1Ac, Cry2Aa, and Cry2Ab. Spores and crystals suspension from this bacterium was prepared and tested with BtB inclusion bodies in tomato leaf dip bioassay. These leaves were fed to $2^{nd}$ instar *H. zea* larvae and the bioassay was scored on the second day. The bioassay results show that only BtB3 the protease-stabilized Ms-CR10-12(PS) significantly enhanced NRD12 (FIG. 4A).

In another leaf dip bioassay, Javelin WG was mixed with either BtB2 or BtB3 and applied on the leaves. These leaves were fed to $2^{nd}$ instar *H. zea* larvae, and the bioassay was scored on the fourth day. The results show that only BtB3 significantly enhanced Javelin WG against the larvae (FIG. 4B). This result is significant because it showed that BtB3 was able to enhance a commercial Bt formulation which contains inert materials that might have interfered with the synergist.

BtB Enhanced B.t. Cotton.

Transgenic Cry1Ac B.t. cotton (Bollgard™, Monsanto Co., St. Louis, Mo.) has been available commercially since 1996. Although it is highly efficient in controlling *H. virescens* and *P. gossypiella*, supplemental foliar spray is needed to control *H. zea* (Adamczyk et al., 2001). Leaves from 4-5 weeks old B.t. cotton were dipped in BtB inclusion bodies and air dried. These leaves were fed to $2^{nd}$ instar *H. zea* larvae, and the bioassay was scored on the fourth day (FIG. 5). Mortality was significantly increased when the leaves were treated with either BtB2 or BtB3 (P<0.05).

BtBooster Enhanced B.t. Against Bt-Resistant Insect.

As with conventional insecticides, resistance of target insects to B.t. may not be avoidable. Insects have been selected for resistance against Bt in the laboratory settings as well as in the field (reviewed in (Griffitts et al., 2005; McGaughey, 1985)). The diamondback moth, *P. xylostella*, is an agricultural pest of cruciferous crops including cabbage and canola. Very high resistance against Bt has developed in the field for this pest (Ferre et al., 1991; Liu et al., 1996; Tabashnik et al., 1990).

A laboratory-selected strain of Bt-resistant *P. xylostella* was tested against Agree WG (a Cry1A and Cry1C producing strain of Bt) and Javelin WG (a Cry1Aa, Cry1Ab, Cry1Ac, Cry2Aa, and Cry2Ab producing strain of Bt). From a diet incorporation bioassay, it was determined that this strain was about 128-fold more susceptible to Agree WG than to Javelin WG (FIG. 6A). This was expected since the resistant insects were selected on Bt HD-1, which produces the same Cry toxins present in Javelin WG. Agree WG, however, contain Cry1C which has been shown to have very little cross resistance to Cry1A toxins and is highly active against *P. xylostella* (Tang et al., 1996). Both BtB2 and BtB3 inclusion bodies were able to significantly enhance Javelin WG and Agree WG against a Bt-resistant strain of *P. xylostella* (FIGS. 6B and 6C). These results suggest that the addition of BtB to B.t. formulations can reduce the development of resistance in target insects. This is a very important feature that increases its value in integrated pest management program.

Sequence Alignments.

As BtB2 represents CR12, and BtB3 is a modified CR12 (see FIG. 20), alignment of the CR12 region from ten different lepidopteran species (*Ostrinia nubilalis* (European Corn Borer), *Chilo suppressalis* (Striped Rice Borer), *M. sexta* (Tomato Hornworm), *P. xylostella* (Diamondback Moth), *Pectinophora gossypiella* (Pink Bollworm), *Lymantria dispar* (Gypsy Moth), *Bombyx mori* (Silkworm), *Helicoverpa armigera* (Cotton Bollworm), and *Heliothis virescens* (Tobacco Budworm) and *Spodoptera frugiperda*) showed more than 50% similarity in sequence (see FIG. 20). This suggests that BIB can work against these insects that share a common protein. All three versions of BtB bound Cry1A toxins strongly in dot-blot assays. This is consistent with a prior report that showed that the CR12 region is required for toxin binding (Hua et al., 2004b).

Further Insights into Mechanism(s) of Action.

Cry toxins bind to BtB and high affinity binding is correlated with toxicity enhancement. For example, as measured by surface plasmon resonance analysis using a BIAcore, the original BtB (Ms-CR12-MPED) bound Cry1Ab at high (9 nM) and low (1 µM) affinity sites. BtB (CR12-MPED)-mediated Cry1A toxicity enhancement was significantly reduced when the high affinity Cry1A-binding epitope ($^{1416}$GVLTLNIQ$^{1423}$) within the peptide was altered. The BtB peptide bound brush border membrane vesicles (BBMV) with high affinity (Kd=32 nM) and insect midgut microvilli, but did not alter Cry1Ab or Cry1Ac binding localization in the midgut.

Without being bound by a specific theory, one possible explanation of the observed synergism is that BtB-type peptides bind to the microvilli and attract Cry1A molecules, increasing the probability of toxin interaction with Cry1A receptors such as Bt-R$_1$, GPI-anchored aminopeptidase N and alkaline phosphatase, or sphingoglycolipids (Griffitts et al., 2005). This hypothesis is consistent with the model proposed by Bravo whereby binding of Cry1A monomer to the cadherin Bt-R$_1$ induces structural changes in the toxin that result in further processing and formation of a toxin oligomer. As a Bt-R$_1$ truncation for Cry1A binding, the addition of CR12-MPED might promote the switch of toxin from monomer to oligomer, a form which primarily binds to GPI-anchored receptors resulting in oligomer insertion in the cell membrane.

Since the interaction between BtB and Bt toxins produced a possible novel mode of action for the toxin, the addition of BtB to Bt formulations or Bt transgenic plants might delay resistance.

Several potential advantages can be attributed to BtB: (1) It reduces the amount of Cry protein needed to kill larvae, thus also prolonging pesticidal activity by enhancing the residual activity of Cry protein; (2) It expands host range of Bt biopesticides and (3) It may overcome certain types of acquired resistance to Bt proteins. This discovery suggests that BtB can be used as an additive to Bt to increase its efficacy and potentially increase the usage of Bt biopesticide in agriculture.

We found that low mass ratios (Cry toxin:BtB) were needed for BtB4 and BtB5 to enhance Cry1Ac toxicity to *H. zea* larvae (FIG. 9). This is significant because *H. zea* is an important pest of cotton, corn and other crops. The low mass ratios of Cry toxin:BtB are desirable for producing BtB protein for use in biopesticides and transgenic plants.

FIG. 9 shows the shift in LC$_{50}$ values observed for BtB4 and BtB5 tested at 1:2 (Cry toxin:BtB) mass ratios against *H. zea* larvae. A lower LC50 value means that with BtB4 or BtB5 the insect larvae at killed at lower Bt toxin concentrations.

We found the BtB4 could enhance Cry1Ac toxicity to *A. ipsilon* (black cutworm) (FIG. 11A). The black cutworm, *A. ipsilon*, is very tolerant to most Bt toxins (de Maagd et al., 2003). It is only susceptible to BE toxins at very high doses as demonstrated by diet overlay bioassay. The LC$_{50}$ for Cry1Ac we determined was 19.3 (17.9-20.9) μg/cm$^2$ (95% fiducial limits in parenthesis). However, the LC$_{50}$ for Cry1Ac with the addition of 10-fold mass ratio of CR10-12 (BtB4) was reduced to 2 μg/cm$^2$ (~10-fold enhancement). This is important because cutworms are difficult to control crop pests with Bt Cry toxins.

We found that BtB4 and BtB5 could enhance Cry1Ab and Cry1Ac toxicity to *S. exigua* (FIG. 8). In FIG. 11B, further evidence is presented that that BtB4 could enhance Cry1Ab toxicity to *S. exigua* (beet armyworm) (FIG. 11B). The diet overlay assays confirmed that the larvae are very tolerant to Cry1Ab. The LC$_{50}$ for Cry1Ab was estimated at about 7 μg/cm$^2$ (although the fiducial limit could not be determined due to insufficient data). However, the LC$_{50}$ for Cry1Ab with the addition of 5-fold mass ratio of Ms-CR10-12 (BtB4) was reduced to 1.1 (0.9-1.3) μg/cm$^2$ (about a 6-fold enhancement).

FIG. 12 shows that low ratios of Cry1C:BtB4 (Ms-CR10-12) could enhance Cry1C toxicity to *S. exigua*.

BtB5 could also lower the amount of Cry1Ab and Cry1Fa needed to kill *H. zea* larvae. As shown in FIG. 13 the LC$_{50}$ values for Cry1Ab and Cry1Fa are substantially lower in the presence of BtB5. This is important because Cry1Ab and Cry1Fa are produced in genetically engineered plants and increased insect control is desirable. Cry1Ab and Cry1Fa may also be used in biopesticides with BtB for enhanced insect control.

In a similar manner BtB5 substantially increased Cry1Ab and Cry1Fa toxicity to *S. exigua* (beet armyworm) (FIG. 14).

BtB5 substantially increased the toxicity of Cry1Ab and Cry1Fa to *S. exigua* (beet armyworms) The beet armyworm is an important pest that is difficult to control with most Bt Cry proteins. Note in FIG. 14 how without BtB5, Cry1Ab did not cause larval mortality.

Our data presented in FIG. 15 demonstrate that BtB5 could enhance both individual and combinations of Cry toxins. BtB5 enhanced a mixture of Cry1Ab+Cry1Fa toxins when tested in bioassay against *H. zea* larvae. This is important because Cry1Ab and Cry1Fa toxins are likely to be co-expressed in Bt corn and other crops.

Figure 1:
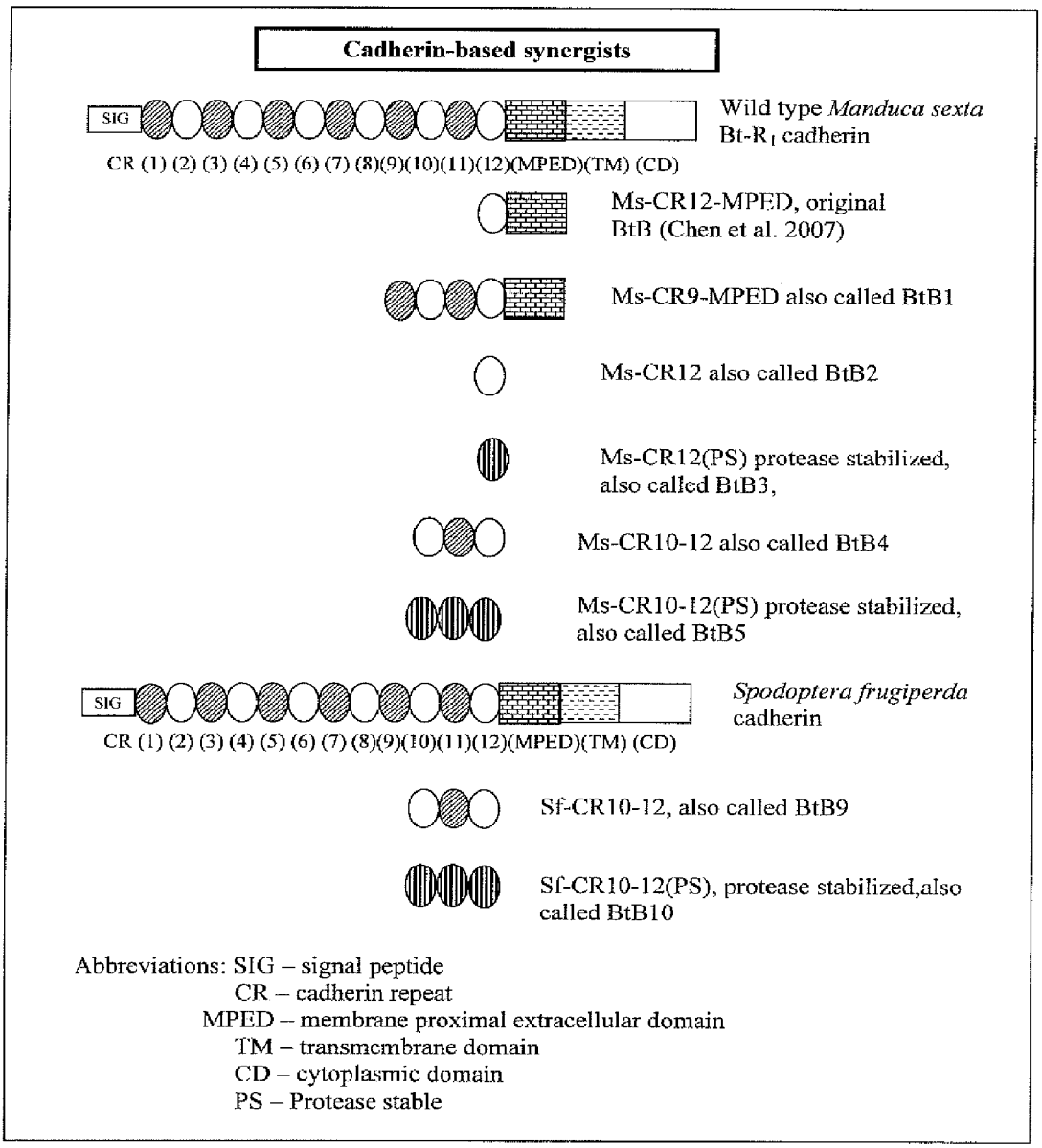
FIG. 1 illustrates the wild-type BtR1 cadherin of *M. sexta* and the cadherin fragments Ms-CR12-MPED, Ms-CR9-MPED (BtB1), Ms-CR12 (BtB2), the protease-stabilized version Ms-CR12(PS) also called BtB3, Ms-CR10-12 (BtB4) and the proteinase-stabilized Ms-CR10-12(PS) fragment called Bt135 that were tested successfully.

Two BtBs (BtB9 and BtB10 as shown in FIG. 1) were designed with the possibility that they may have increased enhancing properties for Cry toxins active against *Spodoptera* species. Data presented in FIGS. 17A and 17B are evidence that BtB9 and BtB10 increase Cry1F toxicity to *S. frugiperda*. Note, BtB5 also increased Cry1F toxicity. These results are because Cry1F is produced in Bt corn and cotton.

Our data presented in FIG. 18 suggest another mechanism that explains the synergism of BtB-type peptides. When BtB was added to Cry1Ab toxin, the toxin was stabilized against digestion by midgut digestive enzymes. This is important because over-digestion of toxin to inactive peptides is a known mechanism of insect resistance to Bt toxins.

Our data presented in FIG. 19 are evidence that BtB cadherin fragments enhance Cry1Ac toxicity to insects when co-expressed in plants. Plant expression constructs for BtB1 (SEQ ID NO: 3) and BtB3 (SEQ ID NO: 4) were co-transformed into *Arabidopsis* with a synthetic cry1Ac gene coding region using T-DNA vectors in *Agrobacterium tumefaciens*. Plants were also transformed with only the cry1Ac construct. Plants transgenic for BtB and Cry1ac genes were selected for antibiotic and/or herbicide resistance. Progeny transformed plants expressing the same levels of Cry1Ac protein were identified by quantitative Western blot analysis. The levels of BtB1 and BtB3 were also quantitified by Western blot analysis. FIG. 19 shows the mortality response of Bt-resistant *Plutella xylostella* larvae feeding on either leaves of *Arabidopsis* expressing Cry1Ac alone or Cry1Ac plus BtB1 or BtB3. In the left-hand set plant Bt-431 is compared with Bt Cry1Ac plus BtB1 (plant#2) and Bt Cry1Ac plus BtB3 (plant #30). The mortality was greater when a BtB was present with Cry1Ac. In the second set a Cry1Ac producing plant (plant#8) is compared with Cry1Ac plus BtB1 (plant#20) and Cry1Ac plus BtB3 (plant #31). In this plant set, more *P. xylostella* larvae were killed when a BtB was present.

Various *Bacillus thuringiensis* Cry proteins can be used with BtB polypeptides of the subject invention. See Crickmore et al. (1998) (world wide web website lifesci.sussex.ac-.uldhome/Neil_Crickmore/Bt/) for a list of B.t. toxins. These include, but are not limited to, polynucleotides encoding Cry1A toxins such as Cry1Aa, Cry1Ab, Cry1Ac, as well as Cry1B, Cry1C, Cry1F, Cry1E, Cry3A, and the Cry8s, as well as Cry34s+Cry 35s. Cry2 toxins are also preferred for co-administration with peptides of the subject invention.

Various insects can be targeted or otherwise inhibited/controlled by (one or more of) the subject polypeptides/proteins, including:
*Agrotis ipsilon*, black cutworm
*Agrotis orthogonia*, pale western cutworm
*Anticarsia gemmatalis*, velvetbean caterpillar
*Chilo partellus*, sorghum borer
*Diatraea grandioscl1a*, southwestern corn
*Diatraea saccharalis*, sugarcane borer
*Elasmopalpus lignosellus*, lesser cornstalk borer
*Feltia subterranea*, granulate cutworm

*Helicoverpa zea*, corn earworm/cotton bollworm
*Heliothis virescens*, tobacco budworm/cotton boll worm
*Homoeosoma electellum*, sunflower moth
*Ostrinia nubilalis*, European corn borer
*Pectinophora gossypiella*, pink bollworm borer
*Plathypena scabra*, green cloverworm
*Pseudoplusia includens*, soybean limper
*Pseudaletia unipunctata*, army worm
*Spodoptera exigua*, beet armyworm
*Spodoptera frugiperda*, fall armyworm
*Suleima helianthana*, sunflower bud moth Any genus listed above (and others), generally, can also be targeted as a part of the subject invention. Any additional insects in any of these genera (as targets) are also included within the scope of this invention.

The subject polypeptides and protein toxins can be "applied" or provided to contact the target insects in a variety of ways. For example, transgenic plants (wherein the protein is produced by and present in the plant) can be used and are well-known in the art. Expression of the toxin genes can also be achieved selectively in specific tissues of the plants, such as the roots, leaves, etc. This can be accomplished via the use of tissue-specific promoters, for example. Spray-on applications are another example and are also known in the art. The subject polypeptides/proteins can be appropriately formulated for the desired end use, and then sprayed (or otherwise applied) onto the plant and/or around the plant/to the vicinity of the plant to be protected—before an infestation is discovered, after target insects are discovered, both before and after, and the like. Bait granules, for example, can also be used and are known in the art. Various combinations of approaches are discussed in WO 2005/070214 A2, US-2005-0283857-A1, and U.S. Pat. No. 7,396,813.

The subject proteins can be used to protect practically any type of plant from damage by an insect. Examples of such plants include maize, sunflower, soybean, cotton, canola, rice, sorghum, wheat, barley, vegetables, ornamentals, peppers (including hot peppers), sugar beets, fruit, and turf, to name but a few.

In light of and having the benefit of the subject application, variants of novel BtBs of the subject invention (e.g. those derived from *Spodoptera* cadherins) can be constructed using techniques that are known in the art.

It will be recognized by those skilled in the art that the DNA sequences may vary due to the degeneracy of the genetic code and codon usage. All DNA sequences which code for exemplified and/or suggested peptides (and proteins) are included. The subject invention also includes polynucleotides having codons that are optimized for expression in plants, including any of the specific types of plants referred to herein. Various techniques for creating plant-optimized sequences are know in the art.

Additionally, it will be recognized by those skilled in the art that allelic variations may occur in the DNA sequences which will not significantly change activity of the amino acid sequences of the peptides which the DNA sequences encode. All such equivalent DNA sequences are included within the scope of this invention and the definition of the regulated promoter region. The skilled artisan will understand that exemplified sequences can be used to identify and isolate additional, non-exemplified nucleotide sequences that will encode functional equivalents to the DNA sequences, including those that encode amino acid sequences having at least 85% identity thereto and having equivalent biological activity, those having at least 90% identity, and those having at least 95% identity to a novel BtB polypeptide of the subject invention. Other numeric ranges for variant polynucleotides and amino acid sequences are provided below (e.g., 50-99%). Following the teachings herein and using knowledge and techniques well known in the art, the skilled worker will be able to make a large number of operative embodiments having equivalent DNA sequences to those listed herein without the expense of undue experimentation.

As used herein percent sequence identity of two nucleic acids is determined using the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. (1997) *Nucl. Acids. Res.* 25:3389-3402. When utilizing BLAST and Gapped BLAST programs, the default parameters of the respective programs (NBLAST and XBLAST) are used. See ncbi.nih.gov website.

Polynucleotides (and the peptides and proteins they encode) can also be defined by their hybridization characteristics (their ability to hybridize to a given probe, such as the complement of a DNA sequence exemplified herein). Various degrees of stringency of hybridization can be employed. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well known in the art, as described, for example, in Keller, G. H., M. M. Manak (1987) *DNA Probes*, Stockton Press, New York, N.Y., pp. 169-170.

As used herein "moderate to high stringency" conditions for hybridization refers to conditions that achieve the same, or about the same, degree of specificity of hybridization as the conditions "as described herein." Examples of moderate to high stringency conditions are provided herein. Specifically, hybridization of immobilized DNA on Southern blots with $^{32}P$-labeled gene-specific probes was performed using standard methods (Maniatis et al.). In general, hybridization and subsequent washes were carried out under moderate to high stringency conditions that allowed for detection of target sequences with homology to sequences exemplified herein. For double-stranded DNA gene probes, hybridization was carried out overnight at 20-25° C. below the melting temperature (Tm) of the DNA hybrid in 6×SSPE, 5×Denhardt's solution, 0.1% SDS, 0.1 mg/ml denatured DNA. The melting temperature is described by the following formula from Beltz et al. (1983).

$$Tm=81.5° C.+16.6 \text{ Log } [Na+]+0.41(\% G+C)-0.61 (\% \text{ formamide}) 600/\text{length of duplex in base pairs.}$$

Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

For oligonucleotide probes, hybridization was carried out overnight at 10-20° C. below the melting temperature (Tm) of the hybrid in 6×SSPE, 5×Denhardt's solution, 0.1% SDS, 0.1 mg/ml denatured DNA. Tm for oligonucleotide probes was determined by the following formula from Suggs et al. (1981):

$$Tm\ (° C.)=2(\text{number } T/A \text{ base pairs})+4(\text{number } G/C \text{ base pairs})$$

Washes were typically carried out as follows:
(1) Twice at room temperature for 15 minutes 1×SSPE, 0.1% SDS (low stringency wash).
(2) Once at the hybridization temperature for 15 minutes in 1×SSPE, 0.1% SDS (moderate stringency wash)

In general, salt and/or temperature can be altered to change stringency. With a labeled DNA fragment of greater than about 70 or so bases in length, the following can be used:

1 or 2×SSPE, room temperature 1 or 2×SSPE, 42° C.

0.2× or 1×SSPE, 65° C.

0.1×SSPE, 65° C.

Duplex formation and stability depend on substantial complementarity between the two strands of a hybrid, and, as noted above, a certain degree of mismatch can be tolerated. Therefore, polynucleotide sequences of the subject invention include mutations (both single and multiple), deletions, and insertions in the described sequences, and combinations thereof, wherein said mutations, insertions, and deletions permit formation of stable hybrids with a target polynucleotide of interest. Mutations, insertions, and deletions can be produced in a given polynucleotide sequence using standard methods known in the art. Other methods may become known in the future.

The mutational, insertional, and deletional variants of the polynucleotide and amino acid sequences of the invention can be used in the same manner as the exemplified sequences so long as the variants have substantial sequence similarity with the original sequence. As used herein, substantial sequence similarity refers to the extent of nucleotide similarity that is sufficient to enable the variant polynucleotide to function in the same capacity as the original sequence. Preferably, this similarity is greater than 50%; more preferably, this similarity is greater than 75%; and most preferably, this similarity is greater than 90%. The degree of similarity needed for the variant to function in its intended capacity will depend upon the intended use of the sequence. It is well within the skill of a person trained in this art to make mutational, insertional, and deletional mutations that are designed to improve the function of the sequence or otherwise provide a methodological advantage. In some embodiments, the identity and/or similarity can also be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein.

The amino acid identity/similarity and/or homology will be highest in critical regions of the protein that account for biological activity and/or are involved in the determination of three-dimensional configuration that ultimately is responsible for the biological activity. In this regard, certain amino acid substitutions are acceptable and can be expected if these substitutions are in regions that are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. The following table provides a listing of examples of amino acids belonging to each class.

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Construction of Booster Peptides Having Increased Stability to Insect Proteases

Several modifications were made to the MS-CR12 peptide to increase its stability in the proteolytic larval gut environment. This was done by replacing amino acids in putative trypsin and cyhmotrypsin cleavage sites on CR12 to remove the cleavage sites. The peptide sequences of the wild type CR12 and a protease stable mutant Ms-CR12(PS)=BtB3 are shown below. The underlined amino acids are the residues that were replaced.

a. MS-CR12 wt (BtB2)

(SEQ ID NO: 5)

MGISTADSIGRELLRLHATQSEGAAITYAIDYDTMVVDPSLEAVRQSAFV

LNAQTGVLTLNIQPTATMHGLFKFEVTATDTAGAQDRTDVTVYVVSSQNR

VYFVLEHHHHHH b. MS-CRCR12(PS) (BtB3)

(SEQ ID NO: 8)

MGISTADSIGSELLSLHATQSEGAAITYAIDYDTMVVDPSLEAVSQSALV

LNAQTGVLTLNIQPTATMHGLINIEVTATDTAGAQDRTDVTVYVVSSQNR

VYFVLEHHHHH

The Ms-CR10-12 peptide was designed from the CR10-12 region of Bt-R1a (Hua et al., 2004a). Modifications were also made to the pMS-CR10-12 peptide for expression in *E. coli* and other prokaryotic cells. Modifications included codon optimization for *E. coli* was performed using online software; see the following worldwide web site: evolvingcode.net/codon/sgd/index.php. We also changed the N-terminus for initiating protein expression and the C-terminus for ease of protein purification using an immobilized nickel column.

MS-CR10-12(13tB4):

(SEQ ID NO: 11)

MHLERISATDPDGLHAGVVTFQVVGDEESQRYFQVVNDGANLGSLRLLQA

VPEEIREFRITIRATDQGTDPGPLSTDMTFRVVFVPTQGEPRFASSEHAV

AFIEKSAGMEESHQLPLAQDIKNHLCEDDCHSIYYRIIDGNSEGHFGLDP

-continued
VRNRLFLKKELIREQSASHTLQVAASNSPDGGIPLPASILTVTVTVREAD

PRPVFMRELYTAGISTADSIGRELLRLHATQSEGAAITYAIDYDTMVVDP

SLEAVRQSAFVLNAQTGVLTLNIQPTATMHGLFKFEVTATDTAGAQDRTD

VTVYVVSSQNRLEHHHHHH

Modifications were also made to the Ms-CR10-12 to increase stability in insect midguts. This was accomplished by removing trypsin cleavage sites (R/K-S/A or R-C) in pMS-CR10-12 to yield pMS-CR10-12 (PS)=BtB5)(SEQ ID NO:14):

MHLECISATDPDGLHAGVVTFQVVGDEESQAYFQVVNDGANLGSLSLLQA

VPEEIAEFSITICATDQGTDPGPLSTDMTFAVVFVPTQGEPAFASSEHAV

AFIEASAGMEESHQLPLAQDIANHLCEDDCHSIYYAIIDGNSEGHFGLDP

VANALFLSAELIAEQSASHTLQVAASNSPDGGIPLPASILTVTVTVAEAD

PAPVFMAELYTAGISTADSIGCELLALHATQSEGAAITYAIDYDTMVVDP

SLEAVCQSAFVLNAQTGVLTLNIQPTATMHGLFNFEVTATDTAGAQDRTD

VTVYVVSSQNRLEHHHHHH

The pSf-CR10-12 peptide (SEQ ID NO:26) was designed from the *S. frugiperda* cadherin sequence and then modified for protease stabilization by the removal of trypsin recognition sites. The approach was as described above for Ms-CR-12(PS) and Ms-CR10-12(PS). Amino acid changes from Sf-CR10-12 to Sf-CR10-12(PS) (SEQ ID NO:29) are indicated the in the alignment of their amino acid sequences below. Changed residues are in bold and designated by 2 in the Prim.cons. sequence.

TABLE 1

Amino acid sequence alignment between Sf-CR10-12 (SEQ ID NO: 26) and Sf-CR10-12(PS) (SEQ ID NO: 29). Changed residues from Sf-CR10-12 (SEQ ID NO: 26) and Sf-CR10-12(PS) (SEQ ID NO: 29) are shown in bold. Prim.cons. sequence shows unchanged residues between Sf-CR10-12 (SEQ ID NO: 26) and Sf-CR10-12(PS) (SEQ ID NO: 29) alone with changed residues designated by 2.

```
                            10         20         30         40         50         60
                            |          |          |          |          |          |
Sf-CR10-12         MKFLDRLSATDEDGLHAGRVTFSIAGNDEAAEYFNVLNDGDNSAMLTLKQALPAGVQQFE
Sf-CR10-12(PS)     MAFLDCLSATDEDGLHAGCVTFSIAGNDEAAEYFNVLNDGDNSAMLTLSQALPAGVQQFE
                   * *** ************ ******************************.**********
Prim.cons.         M2FLD2LSATDEDGLHAG2VTFSIAGNDEAAEYFNVLNDGDNSAMLTL2QALPAGVQQFE 70         80         90        100        110        120
                            |          |          |          |          |          |
Sf-CR10-12         LVIRATDGGTEPGPRSTDCSVTVVFVMTQGDPVFDDNAASVRFVEKEAGMSEKFQLPQAD
Sf-CR10-12(PS)     LVISATDGGTEPGPSSTDCSVTVVFVMTQGDPVFDDNAASVSFVEHEAGMSESFQLPQAD
                   *** ********** ************************ ***.****** *******
Prim.cons.         LVI2ATDGGTEPGP2STDCSVTVVFVMTQGDPVFDDNAASV2FVE2EAGMSE2FQLPQAD 130        140        150        160        170        180
                            |          |          |          |          |          |
Sf-CR10-12         DPKNYRCMDDCHTIYYSIVDGNDGDHFAVEPETNVIYLLKPLDRSQQEQYRVVVAASNTP
Sf-CR10-12(PS)     DPSNYACMDDCHTIYYSIVDGNDGDHFAVEPETNVIYLLSPLDSSQQEQYSVVVAASNTP
                   **.** ********************************.*** ****** *********
Prim.cons.         DP2NY2CMDDCHTIYYSIVDGNDGDHFAVEPETNVIYLL2PLD2SQQEQY2VVVAASNTP 190        200        210        220        230        240
                            |          |          |          |          |          |
Sf-CR10-12         GGTSTLSSSLLTVTIGVREANPRPIFESEFYTAGVLHTDSIHKELVYLAAKHSEGLPIVY
Sf-CR10-12(PS)     GGTSTLSSSLLTVTIGVSEANPSPIFESEFYTAGVLHTDSIHSELVYLAASHSEGLPIVY
                   ***************** **** ******************.******.**********
Prim.cons.         GGTSTLSSSLLTVTIGV2EANP2PIFESEFYTAGVLHTDSIH2ELVYLAA2HSEGLPIVY 250        260        270        280        290        300
                            |          |          |          |          |          |
Sf-CR10-12         SIDQETMKIDESLQTVVEDAFDINSATGVISLNFQPTSVMHGSFDFEVVASDTRGASDRA
Sf-CR10-12(PS)     SIDQETMSIDESLQTVVEDAFDINSATGVISLNFQPTSVMHGSFDFEVVASDTCGASDCA
                   *******.********************************************  **** *
Prim.cons          SIDQETM2IDESLQTVVEDAFDINSATGVISLNFQPTSVMHGSFDFEVVASDT2GASD2A 310
                            |
Sf-CR10-12         KVSIYMISTRVRVHHHHHH
Sf-CR10-12(PS)     SVSIYMISTRVRVHHHHHH
                   .******************
Prim.cons          2VSIYMISTRVRVHHHHHH
```

EXAMPLE 2

Production of BtBooster in *E. coli* and Formulation of a Dried-Cell Powder BtBooster Product The BtBooster (MsCR10-12(PS)=BtB5) gene was synthesized with a 5' NdeI site and a 3' HindIII restriction site. The BtB5 gene was subcloned into pET30a(+) at the NdeI and HindIII restriction sites. The hexahistidine tag is located at the C-terminus of BtB5 peptide. The start codon (ATG) is located at the NdeI site. The stop codon (TAA) occurs after the his-tag codons, immediately before the HindIII site. The BtB constructs were subcloned into pET30a (Novagen) and expressed in BL21(DE3)pRIL cells. *E. coli* cells were transformed by a standard electroporation method into *E. coli* BL21(DE3) pRIL (Novagen). The Ms-CR10-12(PS)peptide was over-expressed in *E. coif* as inclusion bodies. The expression and purification protocol for the truncated cadherin fragment was as described in a previous paper (Chen et al., 2007). The inclusion body form was prepared as a suspension in sterile deionized water. Total protein was measured by Bio-Rad protein assay using bovine serum albumin (BSA) as standard (Bradford, 1976). One microgram of each cadherin peptide was analyzed by sodium dodecyl sulfate—1.5% polyacrylamide gel electrophoresis (SDS-15% PAGE) with Coomassie brilliant blue R-250 staining. Specific concentration of target protein, such as toxin or the cadherin peptide in total protein was determined from Coomassie-stained gel by gel image analyzer (Alpha Innotech, San Leandro, Calif.) using bovine serum albumin (BSA) as standard.

The following conditions illustrate a method for producing BtB for use with Bt formulations in field trials.

Growth Medium:

50 mM (NH4)2SO4, 2 mM MgSO4.7H2O, 40 mM KH2PO4, 55 mM Na2HPO4, 1% (w/v) tryptone, 0.5% (w/v) yeast extract, 30 mM sodium citrate, 1% (v/v) glycerol, 1% (w/v) glucose; Adjust pH to 7.2 with NaOH. Autoclave all components together at 121° C. for 15 min. After autoclaving, add to sterile medium: 10 mM Proline (filter sterilized), and 100 mg/ml Kanamycin (filter sterilized).

Growth and Induction Conditions:

*E. coli* cells were grown in fermentor (up to 500 L) at 37° C., pH 6.8, and 30% dissolved oxygen. The cells were induced with 1 mM IPTG when the $OD_{600}$ reached 4 or 5. The cells were grown overnight and harvested the next day ($OD_{600}$=27-43).

Cell Harvesting and Lysis:

The cells were centrifuged and resuspended in (3 ml per gram pellet ratio) 20 mM $NaH_2PO_4$, 0.1% Triton X-100, pH 4.5. The cells were homogenized/broken using a microfluidizer. The lysate was centrifuged and the pellet was resuspended (2 ml per gram pellet ratio) in 20 mM $NaH_2PO_4$, 10% (w/v) sucrose, 0.1% Triton X-100, pH 4.5.

Spray Drying Condition:

The lysed cell pellet was spray dried using a Niro Production Minor Spray Dryer (4' diameter) under standard conditions. Starting weight of material was 62.7 pounds. Material dried without difficulty. At the end of the run, drying chamber brushdown was collected separately and labeled accordingly. Dried samples are stored at 4° C. for later quality control analysis and testing in field trials.

EXAMPLE 3

Preparation of Bt Spores and Crystals-Toxin Preparation

Formulated Bts including Javelin® WG, and Agree® were provided by Certis Corporation. The formulated Bt products XenTari® DiPel® DF were purchased from a local pest control distributor.

Cry1Ac crystal protein was prepared from *Bacillus thuringiensis* HD-73 essentially as describe previously (Luo et al., 1996). Cry1Ca protein and Cry1Fa were purified from individual Bt strains producing either Cry1Ca or Cry1Fa. The cells were grown in a shaker at 30° C. until cell lysis in a sporulation medium. The spore-crystal preparation was cleaned by a series of sonication and homogenization in detergent (Triton X-100) and high molar salt (1 M NaCl), and finally the spore-crystal preparation was washed and resuspended in distilled water. The Cry1Ac crystal was solubilized in 50 mM $Na_2CO_3$ pH 10.5 and activated by trypsin digestion. The toxin was purified by Q-sepharose anion exchange chromatography. Protein concentration was determined using BSA as a standard (Luo et al., 1996). The toxin was aliquoted into 1.5-ml microcentrifuge tubes and stored at −20° C. until needed. Bt NRD12 (the active ingredient in Javelin WG) was also prepared the same way except that the process was stopped after the spore-crystal preparation was resuspended in distilled water. The spore-crystal sample was kept at 4° C. until use.

The cry1Ab gene was over-expressed in *Escherichia coli* JM103 by using the expression vector pKK223-3 (Lee et al., 1992). Toxin preparation was as described above for preparation of Cry1 toxin derived from Bt crystals.

EXAMPLE 4

Insects and Insect Bioassays

Insects.

All insect eggs were purchased from Benzon Research (Carlisle, Pa.), and emerged larvae were maintained on artificial insect diet (multiple species insect diet, Southland Products, Lake Village, Ark.). The Bt-resistant *P. xylostella* was selected with Bt *kurstaki* HD-1 spore-crystal by Benzon Research. The resistant insects were about 800-1000 fold less susceptible to the HD-1 spore-crystal compared to the susceptible (unselected) *P. xylostella* (data not shown).

Diet Incorporation Bioassay with Bt-Resistant *P. xylostella*.

Artificial diet was prepared according to the manufacturer's instruction (Southland Products, Lake Village, Ark.) and cooled to 60° C. before mixing with Javelin WG (Certis, Columbia, Md.) (with or without BtB) or Agree WG (Certis, Columbia, Md.) (with or without BtB) and pipetted into 128-well bioassay trays (C-D International) with a 30-ml plastic syringe. One or three insect neonate was placed in each well. Each treatment contained 16 or 48 larvae with two replicates. Insects were placed in an incubator at 28° C. with a photoperiod of 12:12 h (L:D). Larval mortalities were counted 7 days after treatment.

Diet Surface Overlay Bioassay with IL zea, *S. exigua*, *S. frugiperda* and *A. ipsilon*.

Artificial diet was prepared according to the manufacturer's instruction (Southland Products, Lake Village, Ark.) and pipetted into 128-well bioassay trays. Using distilled water as diluent, Cry1 toxin (with or without BtB) (50 µl) was applied uniformly on the diet surface diet and allowed to dry. A single neonate was placed in each well. Each treatment contained 32 larvae with two replicates. Insects were placed in an incubator at 28° C. with a photoperiod of 12:12 h (L:D). Larval mortalities were counted 7 days after treatment Diet overlay bioassays for *H. zea* and *S. exigua* neonates were scored at 7 days after treatment (DAT) and bioassays for *A. ipsilon* neonates were scored at 6 DAT.

Tomato Leaf Dip Bioassay with II. zea.

*H. zea* larvae were grown at 28° C. with a photoperiod of 12:12 h (L:D) for 5 days on artificial diet (Southland Products). The larvae were approximately late second instar at the start of bioassay. Tomato seeds (Better Boy Hybrid—catalog no. 5323-SD) were purchased from Park Seed Wholesale, Greenwood, S.C. The plants were maintained in a growth chamber at 28° C., 14:10 photoperiod, and about 80% relative humidity. When the plants were about 10-12 inches tall, leaves were cut at about 2×3 cm and dipped into treatment solutions. The treated leaves were then air dried and placed individually into lidded plastic cups. Each of the cups also contains a wet Whatman fitter paper. A single larva was added into each cup and mortality was scored on day 2 and 3. Fresh-cut tomato leaves were added on Day 2. Thirty larvae were used per treatment with two replicates. 0.02% Tween 20 (Sigma Aldrich, St. Louis, Mo.) was used as a diluent. Insects were placed in an incubator at 28° C. with a photoperiod of 12:12 h (L:D). Larval mortalities were determined 2 to 4 days after treatment. Larvae were considered dead when no larval movement was detected after being prodded. All insect bioassay was repeated at least once.

Cabbage Excised-Leaf Bioassay.

Copenhagen market early cabbage plants were sprayed in the greenhouse with test solution and allowed to dry. Cabbage leaves were removed and cut into ~30×55 mm pieces, placed in 30 ml clear plastic cups with 1 or more larvae (3 or 4 days old) and capped. Typically 3 replicates of 30 larvae for each dose were done. The bioassays were done at 28° C. with a photoperiod of 12:12 h (L:D). Larval mortalities were determined 4 days after treatment. Larvae were considered dead when no larval movement was detected after being prodded. All insect bioassay was repeated at least once.

Statistical Analysis.

The number of surviving and dead larvae in one treatment was compared with another treatment using a 2×2 contingency table by Chi-square analysis. Treatments are not significantly different if P>0.05.

EXAMPLE 5

Results—Longer Cadherin Fragments have Improved Toxin Enhancement Properties

Enhancement of Cry1Ac Toxicity by 'Longer' *M. sexta* Cadherin Fragments.

Previously, a small fragment of a *M. sexta* cadherin (Ms-CR12-MPED) was demonstrated as a potent enhancer of Cry1Ab and Cry1Ac toxins (Chen et al., 2007b) (Chen et al., 2007a). Mutation of the CR12 region of the CR12-MPED synergist to remove a Cry1Ab-binding region was shown to block the enhancer activity (Chen et al., 2007b), suggesting the importance of CR12 for toxin enhancement activity. Fragments of *M. sexta* cadherin longer than MS-CR12 were produced to test their synergistic activity with Cry1Ac toxin. Cadherin fragments of various lengths corresponding to CR7-12, CR9-12, CR10-12, and CR11-12, expressed in *E. coli*, formed insoluble inclusion bodies. The inclusion bodies were washed and resuspended in deionized water for use in bioassays.

Diet overlay bioassays on neonate *H. zea* were performed using trypsin-activated Cry1Ac with cadherin fragments set at a fixed toxin to cadherin mass ratio of 1:20 (FIG. 2). The $LC_{50}$ for Cry1Ac alone was estimated to be 1 µg/cm² (fiducial limits could not be determined due to insufficient data). The $LC_{50}$ of Cry1Ac in the presence of the cadherin fragments was reduced by 12- to 50-fold. Toxin enhancements by CR7-12, CR9-12, and CR10-12 have overlapping confidence limits, suggesting that the enhancement levels were not significantly different. However, enhancement by CR11-12 was significantly lower compared to the other three longer cadherin fragments. Based on our evaluation of these results, it was decided that CR10-12 will be used for further testing because it was the minimum cadherin length that provided a high enhancement level.

EXAMPLE 6

Cadherin Fragments Increase Cry Toxicity to Difficult to Control Insect Species

Other studies, combining Bt with BtBooster™, tested against *H. zea, S. exigua, S. frugiperda, Plutella xylostella* (Bt-resistant and susceptible populations), and *Agrotis ipsilon* have also demonstrated significant increases in mortality. It is important to note that BtBooster™ alone has demonstrated no effects on a wide range of insects, including these species. Artificial diet bioassays, leaf bioassays and whole plant bioassays in the laboratory and greenhouse have provided supportive data. A random selection of different bioassay results are provided below.

Enhancement of Cry1Ac Toxicity Against *A. epsilon*.

The black cutworm, *A. ipsilon*, is very tolerant to most Bt toxins (de Maagd et al., 2003). It is only susceptible to Bt toxins at very high doses as demonstrated by diet overlay bioassay (FIG. 11A). The $LC_{50}$ for Cry1Ac was determined to be 193 (17.9-20.9) µg/cm² (95% fiducial limits in parenthesis). However, the $LC_{50}$ for Cry1Ac with the addition of 10-fold mass ratio of CR10-12 was reduced to approximately 2 µg/cm² (~10-fold enhancement).

Enhancement of Cry1Ab Toxicity Against *S. exigua*.

The beet armyworm, *S. exigua*, is highly tolerant to Bt toxins, especially Cry1A type toxins (Hernandez-Martinez et al., 2008). Diet overlay bioassay on neonate *S. exigua* using trypsin-activated Cry1Ab confirmed that the larvae were very tolerant to the toxin (FIG. 11B). The $LC_{50}$ for Cry1Ab was estimated to be ~7 µg/cm². However, the $LC_{50}$ for Cry1Ab with the addition of 5-fold mass ratio of CR10-12 was reduced to 1.1 (0.9-1.3) µg/cm². (~6-fold enhancement).

Enhancement of Cry1Ca and Cry1Ab Toxicity Against *S. exigua*.

*Spodoptera* species are among the more difficult to control lepidopteran pests on cotton, corn, vegetables and cruciferous crops with Bt toxins. In a diet surface overlay bioassay (FIG. 8), the two tested cadherin fragments Ms-CR10-12 and Ms-CR10-12(PS), BtB4 and BtB5 respectively enhanced the toxicity of Cry1Ab toxin to *S. exigua* in diet surface treatment bioassays. Since Cry1Ca toxin is more toxic than Cry1Ab against *S. exigua* larvae (de Maagd et al., 2000; Luo et al., 1999) was also tested for BtB enhancement of Cry1Ca toxin. Diet overlay bioassay with neonate *S. exigua* using trypsin-activated Cry1Ca showed significant enhancement by Ms-CR10-12 over the Cry1Ca alone treatment at varying mass ratios from 1:1 to 1:100 (FIG. 12). The level of enhancement was at a maximum (~5-fold) at 1:1 toxin to Ms-CR10-12 mass ratio The results of the *S. exigua* diet overlay assay presented in FIG. 14 are evidence that Ms-CR10-12(PS), BtB5, significantly enhances both Cry1Ab and Cry1Fa toxicity to *S. exigua*. Note, that Cry1Ab alone, caused no mortality to *S. exigua* larvae.

Enhancement of Cry1Ab and Cry1Fa Toxicity to *S. frugiperda*.

The Fall armyworm, *S. frugiperda* is an occasional, yet important pest of corn and cotton (Fuxa, 1989). Since Cry1Fa has toxicity to *S. frugiperda* (Luo et al., 1999) and Cry1Fa is expressed in Bt corn and cotton, we tested 'improved' BtBs in bioassays with Cry1Fa against *S. frugiperda*. Each BtB tested [Ms-CR10-12(PS), Sf-CR10-12 and Sf-CR10-12(PS)]

caused increased larval mortality when combined with Cry1Fa toxin (FIG. 17A). The Sf-CR10-12 and Sf-CR10-12 (PS) appeared to be better Cry1Fa enhancers than Ms-CR10-12(PS).

EXAMPLE 7

Protease Stabilized BTBs have Improved Enhancement Properties with Bt Spore Crystal Preparations The use of Bt biopesticides depends in large part on the combined efficacy of Bt spores and crystals. The lack of *H. zea* larval mortality observed for combinations of Ms-CR9-MPED (BtB1) and Ms-CR12 when mixed with Bt NRD12 (FIGS. 4A and 4B) prompted us to investigate why these BtBs were not effective under these conditions. By examining the stability of BtBs in digestive juice from insect midgut lumen, we concluded that the BtBs were rapidly degraded by digestive proteases. We solved this instability problem by removing trypsin and some chymotrpsin cleavage sites. Cadherin peptides Ms-CR12(PS) (BtB3), Ms-CR10-12(PS) (BtB5), and SfCR10-12(PS) (BtB10) are examples of cadherin peptides that are modified for increased stability in the presence of insect midgut proteases. The results presented in FIGS. 4A and 4B show that Ms-CR12(PS) enhances Bt strain NRD12 toxicity to *H. zea* larvae in tomato leaf dip bioassays.

Similar results of a protease-stabilized BtB enhancing formulated Bt were observed in cabbage-excised leaf bioassays against 4-day old *H. zea* larvae. Older larvae were tested because they are more tolerant to Bt. As seen in FIGS. 10A and 10B protease-stabilized Ms-CR10-12(PS) significantly enhanced the toxicity of Javelin® and Dipel® to *H. zea* larvae. Protease-stabilized BtB fragments demonstrated improved enhancement of Bt formulations applied to plant leaves.

EXAMPLE 8

Protease Stabilized BTBs have Improved Enhancement Properties with Bt Spore Crystal Preparations A laboratory-selected strain of Bt-resistant *P. xylostella* (purchased from Benzon Research, Inc.) was tested against Agree® WG (a Cry1Aa, Cry1Ca, and Cry1D producing strain of Bt) and Javelin® WG (a Cry1Aa, Cry1Ab, Cry1Ac, Cry2Aa, and Cry2Ab producing strain of Bt). We determined that this strain was about 128-fold more resistant to Javelin® WG than to Agree® WG (FIG. 6A). This was expected since the resistant strain was selected on Bt HD-1, which produces the same Cry toxins present in Javelin® WG. Agree® WG, however, contains Cry1C, which has been shown to have a unique mechanism of action and thus has very little cross resistance to Cry1A toxins and is highly active against *P. xylostella*. Both BtB2 and BtB3 inclusion bodies significantly enhanced Javelin® WG and Agree® WG against the Bt-resistant strain of *P. xylostella* (FIGS. 6B and 6C). These results suggest that the addition of BtB to Bt formulations might overcome resistance in target insects.

REFERENCES

Adamczyk, J. J., Jr., et al., 2001. Field efficacy and seasonal expression profiles for terminal leaves of single and double *Bacillus thuringiensis* toxin cotton genotypes. J. Econom. Entomol. 94(6), 1589-93.

Bradford, M., 1976. A rapid and sensitive method for the quantitation of microgram quantities of protein utilizing the principle of protein-dye binding. Anal. Biochem. 72, 248-254.

Bravo, A., et al., 2004. Oligomerization triggers binding of a *Bacillus thuringiensis* Cry1Ab pore-forming toxin to aminopeptidase N receptor leading to insertion into membrane microdomains. Biochim. Biophys. Acta. 1667, 38-46.

Broderick, N. A., et al., 2006. Midgut bacteria required for *Bacillus thuringiensis* insecticidal activity. Proc. Natl. Acad. Sci. U.S.A. 103, 15196-9.

Carozzi, N. B., et al., 1991a. Prediction of insecticidal activity of *Bacillus thuringiensis* strains by polymerase chain-reaction product profiles. Appl. Environ. Microbial. 57, 3057-3061.

Carozzi, N. B., et al., 1991b. Prediction of insecticidal activity of *Bacillus thuringiensis* strains by polymerase chain reaction product profiles. Appl. Environ. Microbiol. 57, 3057-61.

Chaufaux, J., et al., 1997. Research on natural strains of *Bacillus thuringiensis* in different biotopes throughout the world. Canadian J. Microbiol. 43, 337-343.

Chen, J., et al., 2007. Synergism of *Bacillus thuringiensis* toxins by a fragment of a toxin-binding cadherin. Proc. Natl. Acad. Sci. U.S.A. 104, 13901-13906.

de Maagd, R. A., et al., 2003. Activity of wild-type and hybrid *Bacillus thuringiensis* delta-endotoxins against *Agrotis ipsilon*. Archly. Microbiol. 179, 363-367.

de Maagd, R. A., et al., 2000. *Bacillus thuringiensis* delta-endotoxin Cry1C domain III can function as a specificity determinant for *Spodoptera exigua* in different, but not all, Cry1-Cry1C hybrids. Appl. Environ. Microbiol. 66(4), 1559-63.

DeLucca, A. J., et al., 1979. Two new serovars of *Bacillus thuringinesis*: Serovars dakota and indiana (Serovars 15 and 16). J. Invertbr. Pathol. 34, 323-324.

Dorsch, J. A., et al., 2002. Cry1A toxins of *Bacillus thuringiensis* bind specifically to a region adjacent to the membrane-proximal extracellular domain of BT-$R_1$ in *Manduca sexta*: involvement of a cadherin in the entomopathogenicity of *Bacillus thuringiensis*. Insect Biochem. Molec. Biol. 32, 1025-36.

Ferre, J., et al., 1991. Resistance to the *Bacillus thuringiensis* bioinsecticide in a field population of *Plutella xylostella* is due to a change in a midgut membrane receptor. Proc. Natl. Acad. Sci. USA. 88, 5119-5123.

Francis, B. R., Bulla, L. A., Jr, 1997. Further characterization of BT-R1, the cadherin-like receptor for Cry1Ab toxin in tobacco hornworm (*Manduca sexta*) midguts. Insect Biochem. Molec Biol. 27, 541-550.

Fuxa, J. R., 1989. Seasonal occurrence of *Spodoptera frugiperda* larvae on certain host plants. I Entomol. Sci. 24, 277-289.

Gomez, I., et al., 2002. Cadherin-like receptor binding facilitates proteolytic cleavage of helix $\alpha$-1 in domain I and oligomer pre-pore formation of *Bacillus thuringiensis* Cry1Ab toxin. FEBS Lett. 513, 242-246.

Griffins, J. S., et al., 2005. Glycolipids as receptors for *Bacillus thuringiensis* crystal toxin. Science. 307, 922-925.

Hernandez-Martinez, P., et al., 2008. Susceptibility of *Spodoptera exigua* to 9 toxins from *Bacillus thuringiensis*. J. Invertebr. Pathol. 97, 245-50.

Hua, G., et al., 2004a. Bt-R1a extracellular cadherin repeat 12 mediates *Bacillus thuringiensis* Cry1Ab binding and toxicity. J. Biol. Chem. 279, 28051-28056.

Hua, G., et al., 2004b. Fluorescent-based assays establish *Manduca sexta* Bt-$R_{1a}$ cadherin as a receptor for multiple Bacillus thuringiensis Cry1A toxins in Drosophila S2 cells. Insect Biochem. Molec. Biol. 34, 193-202.

Kaelin, P., et al., 1994. Isolation of Bacillus-Thuringiensis from Stored Tobacco and Lasioderma-Serricorne (F). Appl. Environ. Microbiol. 60, 19-25.

Keeton, T. P., Bulla, L. A., Jr, 1997. Ligand specificity and affinity of BT-R1, the Bacillus thuringiensis Cry1A toxin receptor from Manduca sexta, expressed in mammalian and insect cell cultures. Appl. Environ. Microbiol. 63, 3419-3425.

Lee, M., et al., 1992. Location of a Bombyx mori receptor binding region on a Bacillus thuringiensis delta-endotoxin. J. Biol. Chem. 267, 3115-3121.

Liu, Y. B., et al., 1996. Field-evolved resistance to Bacillus thuringiensis toxin Cry1C in diamondback moth (Lepidoptera: Plutellidae). J. Econ. Entomol. 89, 798-804.

Luo, K., et al., 1999. Toxicity, binding and permeability analyses of four Bacillus thuringiensis Cry1 δ-endotoxins by use of brush border membrane vesicles of Spodoptera exigua and Spodoptera frugiperda. Appl. Environ. Microbiol. 65, 457-464.

Luo, K., et al., 1996. A 106-kDa form of aminopeptidase is a receptor for Bacillus thuringiensis Cry1C δ-endotoxin in the brush border membrane of Manduca sexta. Insect Biochem. Molec. Biol. 26, 33-40.

Martin, P. A. W., Travers, R. S., 1989. Worldwide abundance and distribution of Bacillus thuringiensis isolates. Appl. Environ. Microbiol. 55, 2437-2442.

McGaughey, W. H., 1985. Insect resistance to the biological insecticide Bacillus thuringiensis. Science. 229, 193-195.

Nagamatsu, Y., et al., 1999. The cadherin-like protein is essential to specificity determination and cytotoxic action of the Bacillus thuringiensis insecticidal Cry1Aa toxin. FEBS Lett. 460, 385-390.

Nagamatsu, Y., et al., 1998. Cloning, sequencing, and expression of the Bombyx mori receptor for Bacillus thuringiensis insecticidal Cry1A(a) toxin. Biosci. Biotechnol. Biochem. 62, 727-734.

Schnepf, E., et al., 1998. Bacillus thuringiensis and its pesticidal proteins. Microbiol. Mol. Biol. Rev. 62, 775-806.

Smith, R. A., Couche, G. A., 1991. The phylloplane as a source of Bacillus thuringiensis variants. Appl. Environ. Microbiol. 57, 311-315.

Soberon, M., et al., 2007. Engineering modified Bt toxins to counter insect resistance. Science. 318, 1640-1642.

Tabashnik, B. E., et al., 1990. Field development of resistance to Bacillus thuringiensis in diamondback moth (Lepidoptera: Plutellidae). J. Econ. Entomol. 83, 1671-1676.

Tang, J. D., et al., 1996. Toxicity of Bacillus thuringiensis spore and crystal protein to resistant diamondback moth (Plutella xylostella). Appl. Environ. Microbiol. 62, 564-569.

Zhang, X., et al., 2005. Cytotoxicity of Bacillus thuringiensis Cry1Ab toxin depends on specific binding of the toxin to the cadherin receptor BT-R1 expressed in insect cells. Cell Death Differ. 12, 1407-16.

The invention claimed is:

1. A composition for inhibiting lepidopteran insects, wherein said composition comprises a Cry 1 protein and at least one polypeptide that enhances inhibitory effects of said Cry 1 protein against said lepidopteran insect said polypeptide comprising a Cry binding domain and wherein said modified fragment resists degradation by a protease and said polypeptide differs from a wild-type fragment of an insect cadherin ectodomain comprising said binding domain by one or more amino acid deletions or substitutions that make said polypeptide more resistant to protease degradation than said fragment, wherein said polypeptide is at least 95% identical with SEQ ID NO:14, and wherein said lepidopteran insects are selected from the group consisting of *Heliothis virescens, Helicoverpa zea, Spodoptera fruqiperda,* and *Spodoptera exiqua*.

2. The composition of claim 1 wherein said composition further comprises B.t. spores and/or crystals that comprise said Cry.

3. The composition of claim 1 wherein said polypeptide is modified to remove at least one protease cleavage site present in said wild type fragment, and said cleavage site is a cleavage site for a protease selected from the group consisting of trypsin and chymotrypsin.

4. A method of inhibiting a lepidopteran insect, said method comprising providing a composition of claim 1 to said insect for ingestion, and wherein said lepidopteran insects are selected from the group consisting of *Heliothis virescens, Helicoverpa zea, Spodoptera fruqiperda,* and *Spodoptera exiqua*.

5. The method of claim 4, wherein said Cry protein is present in spores and/or crystals.

6. A method of making a composition of claim 1, said method comprises producing said polypeptide, wherein said polypeptide lacks one or more protease recognition sites present in said wild-type fragment.

7. The method of claim 6, wherein said method comprises obtaining a DNA sequence that encodes said wild-type fragment, and modifying said DNA sequence to remove at least one codon for an amino acid that is part of a protease recognition sequence.

8. The composition of claim 1, wherein said Cry1 protein is selected from the group consisting of Cry1Aa, Cry1Ab, and Cry1Ac.

9. The method of claim 4, wherein said Cry is produced by and is present in a transgenic plant, and said method comprises spraying a composition onto said transgenic plant wherein said composition comprises said polypeptide.

10. The method of claim 4 wherein said insect is a *Spodoptera frugiperda*.

11. The composition of claim 1 wherein said Cry protein is selected from the group consisting of Cry1A, Cry1B, Cry1C, Cry1F, and Cry1E.

* * * * *